United States Patent
Bonny et al.

(10) Patent No.: US 9,688,723 B2
(45) Date of Patent: Jun. 27, 2017

(54) C4S PROTEOGLYCAN SPECIFIC TRANSPORTER MOLECULES

(71) Applicant: PHI PHARMA SA, Sion (CH)

(72) Inventors: Christophe Bonny, Avenches (CH); Fabrice Chenaux, Montmollin (CH)

(73) Assignee: PHI PHARMA SA, Sion (CH)

( * ) Notice: Subject to any disclaimer, the term of this patent is extended or adjusted under 35 U.S.C. 154(b) by 0 days.

(21) Appl. No.: 14/440,949

(22) PCT Filed: Nov. 7, 2013

(86) PCT No.: PCT/EP2013/073279
§ 371 (c)(1),
(2) Date: May 6, 2015

(87) PCT Pub. No.: WO2014/072411
PCT Pub. Date: May 15, 2014

(65) Prior Publication Data
US 2015/0299253 A1    Oct. 22, 2015

Related U.S. Application Data

(60) Provisional application No. 61/763,570, filed on Feb. 12, 2013, provisional application No. 61/723,872, filed on Nov. 8, 2012.

(30) Foreign Application Priority Data

Nov. 8, 2012  (EP) ..................................... 12191840
Feb. 12, 2013  (EP) ..................................... 13154867

(51) Int. Cl.
| | | |
|---|---|---|
| *A61K 38/00* | (2006.01) | |
| *C07K 7/06* | (2006.01) | |
| *C07K 7/08* | (2006.01) | |
| *A61K 31/52* | (2006.01) | |
| *A61K 31/7008* | (2006.01) | |
| *A61K 31/7072* | (2006.01) | |
| *A61K 47/48* | (2006.01) | |

(52) U.S. Cl.
CPC ............... *C07K 7/06* (2013.01); *A61K 31/52* (2013.01); *A61K 31/7008* (2013.01); *A61K 31/7072* (2013.01); *A61K 47/48246* (2013.01); *C07K 7/08* (2013.01)

(58) Field of Classification Search
None
See application file for complete search history.

(56) References Cited

U.S. PATENT DOCUMENTS

| | | |
|---|---|---|
| 6,693,504 B1 | 2/2004 | Snitchler et al. |
| 7,119,644 B2 | 10/2006 | Snitchler et al. |
| 7,722,881 B2 | 5/2010 | Mendelsohn et al. |
| 7,943,143 B2 | 5/2011 | Mendelsohn et al. |
| 8,357,365 B2 | 1/2013 | Kim |
| 8,367,073 B2 | 2/2013 | Mendelsohn et al. |
| 8,520,747 B2 | 8/2013 | Sampath et al. |
| 8,895,499 B2 | 11/2014 | Obrecht et al. |
| 9,217,016 B2 | 12/2015 | Panitch et al. |
| 2003/0011452 A1 | 1/2003 | Snitchler et al. |
| 2003/0078374 A1 | 4/2003 | Roberts et al. |
| 2005/0282755 A1 | 12/2005 | Hart et al. |
| 2006/0005265 A1 | 1/2006 | Bughrara |
| 2009/0117093 A1 | 5/2009 | Kim |
| 2009/0238289 A1 | 9/2009 | Sampath et al. |
| 2009/0324629 A1 | 12/2009 | Mendelsohn et al. |
| 2010/0136037 A1 | 6/2010 | Mendelsohn et al. |
| 2011/0236411 A1 | 9/2011 | Scholler et al. |
| 2011/0318380 A1 | 12/2011 | Brix et al. |
| 2012/0076806 A1 | 3/2012 | Mendelsohn et al. |
| 2013/0189363 A1 | 7/2013 | Obrecht et al. |
| 2014/0301983 A1 | 10/2014 | Panitch et al. |

FOREIGN PATENT DOCUMENTS

| | | |
|---|---|---|
| WO | 0142277 A1 | 6/2001 |
| WO | 0152276 A2 | 7/2001 |
| WO | 03084477 A2 | 10/2003 |
| WO | 2005090385 A2 | 9/2005 |
| WO | 2006088945 A2 | 8/2006 |
| WO | 2007091159 A2 | 8/2007 |
| WO | 2009039854 A2 | 4/2009 |

(Continued)

OTHER PUBLICATIONS

Mohele et al. Angew. Chem. Int. Ed., 2007, 46, p. 9101-9104.*
Kerstin Moehle et al., "Design of [beta]-Hairpin Peptidomimetics that Inhibit Binding of [alpha]-Helical HIV-1 Rev Protein to the Rev Response Element RNA," Angewandte Chemi International Edition, vol. 46, No. 47, pp. 9101-9104 (2007).
Resende Mafalda et al., "Identification of glycosaminoglycan binding regions in the Plasmodium falciparum encoded placental sequestration ligand, VAR2CSA," Malaria Journal, Biomed Central, London, GB, vol. 7, No. 1, pp. 104 (2008).

*Primary Examiner* — Jeanette Lieb
(74) *Attorney, Agent, or Firm* — Jonathan D. Ball; Greenberg Traurig, LLP

(57) ABSTRACT

The present invention relates to isolated molecules, peptides, and polypeptides of specific consensus sequences or structures, and to compounds comprising or consisting of such molecules, peptides and polypeptides, which may act as transporter molecules that specifically recognize proteoglycans, in particular, chondroitin-4-sulfate (C4S). The isolated molecules, peptides, polypeptides and compounds of the invention may be conjugated or otherwise linked to a biologically active moiety (BAM). Thus the BAM conjugates allow the specific targeting and delivery of the BAM, which may be, for example, a peptide, chemical entity or nucleic acid, into the cytoplasm and/or nuclei of C4S expressing cells in vitro and in vivo.

22 Claims, 20 Drawing Sheets

(56) References Cited

FOREIGN PATENT DOCUMENTS

Figure 1:
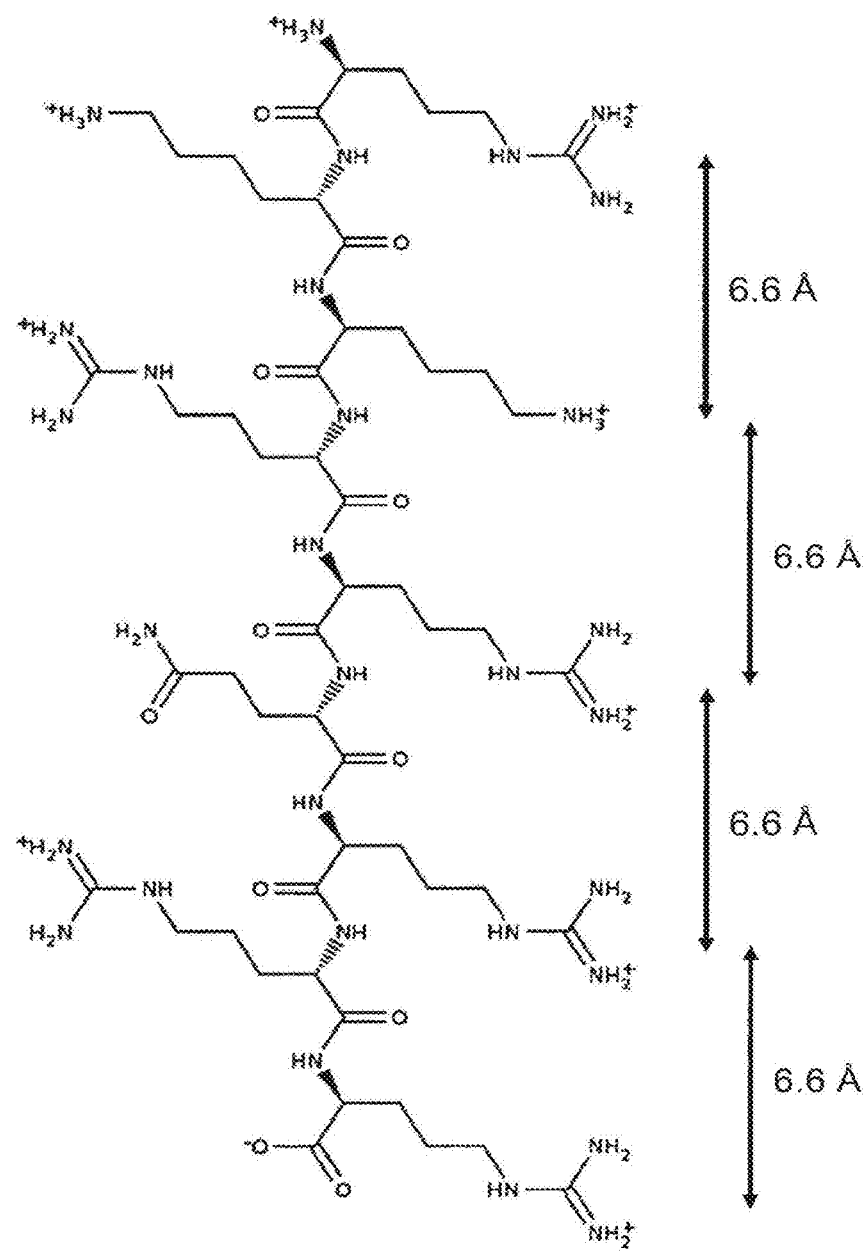
Figure 1:
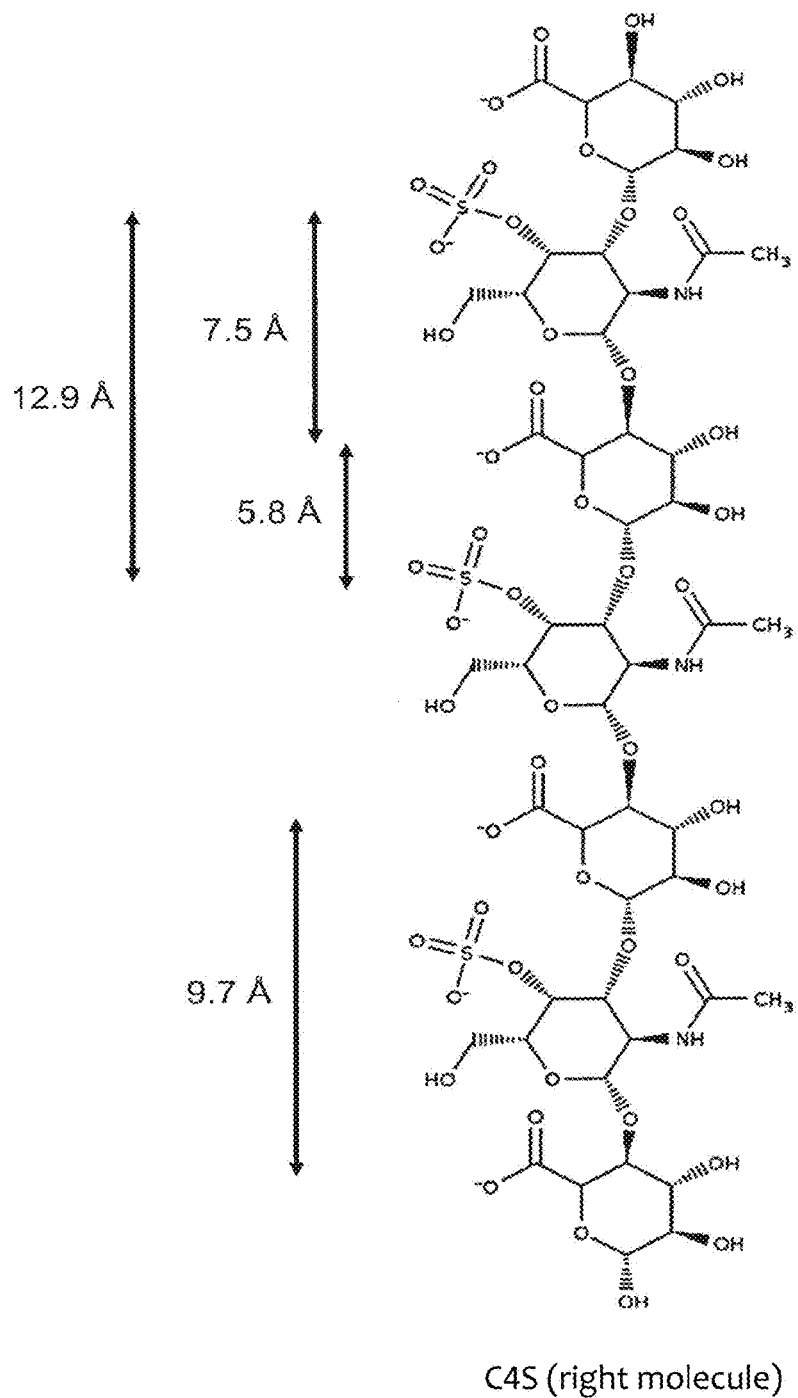

| WO | 2009117254 A2 | 9/2009 |
| WO | 2009157926 A1 | 12/2009 |
| WO | 2010037395 A2 | 4/2010 |
| WO | 2012016595 A1 | 2/2012 |
| WO | 2012162534 A2 | 11/2012 |

* cited by examiner

TAT (left molecule)

C4S (right molecule)

C4S PROTEOGLYCAN SPECIFIC TRANSPORTER MOLECULES

The present application is a National Phase application of International Application No. PCT/EP2013/073279, filed Nov. 7, 2013, which claims priority to U.S. Provisional Application No. 61/763,570, filed Feb. 12, 2013; European Application No. 13154867.9 filed Feb. 12, 2013; U.S. Provisional Application No. 61/723,872, filed Nov. 8, 2012; and European Application No. 12191840.3, filed Nov. 8, 2012. The entirety of each application is incorporated by reference herein. The International Application was published in English on May 15, 2014 as Publication No. WO 2014/072411 A1, the entire contents of which are hereby incorporated by reference herein.

1. Field of the Invention

The present invention relates to isolated molecules, peptides, and polypeptides of specific consensus sequences or structures, and to compounds comprising or consisting of such molecules, peptides and polypeptides, which may act as transporter molecules that specifically recognize proteoglycans, in particular, chondroitin-4-sulfate (C4S). The isolated molecules, peptides, polypeptides and compounds of the invention may be conjugated or otherwise linked to a biologically active moiety (BAM). Thus the BAM conjugates allow the specific targeting and delivery of the BAM, which may be, for example, a peptide, chemical entity or nucleic acid, into the cytoplasm and/or nuclei of C4S expressing cells in vitro and in vivo.

2. Background of the Invention

Cellular membranes are generally impermeable to macromolecules, including proteins and nucleic acids. Moreover, even smaller molecules may enter living cells only at very low rates and in the presence of high, potentially toxic extracellular concentrations. The lack of means for specifically targeting and delivering a compound of interest into specific cells or tissues has been an obstacle to the therapeutic, prophylactic and diagnostic or experimental use of a potentially large number of biologically active molecules having intracellular sites of action.

Over the past decade various means for intracellular delivery of compounds have been investigated in an attempt to facilitate efficient transfer of a substance of interest from the external medium into tissues or cells. The most common delivery constructs have been based on antibodies (or antibody fragments) or on viral and bacterial peptides discovered to have membrane binding and transport activity. For example, transporter constructs have been investigated based on herpes viral VP22 protein; polypeptides comprising the human immunodeficiency virus (HIV) TAT protein, and polypeptides comprising a homeodomain of an Antennapedia protein (Antp HD), as well as functional fragments and modifications thereof.

The majority of the viral and bacterial peptides investigated in the delivery constructs (also termed cell-penetrating peptides (CPPs)) comprise cationic peptides rich in basic residues such as lysine and/or arginine, or peptides comprising alpha helix enhancing amino acids. CPPs have been used to transfect cells in vitro in some experimental animal models, but have demonstrated limited success in clinical trials. It has been postulated that the lack of success in the clinic may arise from their lack of specificity for any particular cell type or tissue, as well as the inherent instability of these peptides in vivo (often exhibiting half-lives on the order of several minutes). To circumvent the lack of in vivo stability, several stabilized CPPs have been developed which have been chemically modified or which contain non-natural amino acids, including "ID" amino-acids. For example, a full "D"-retro-inverso form ("D-TAT") of the archetypal "TAT" peptide has reached clinical Phase 2, but the potentially extremely long persistence of this peptide has limited its uses to topical administration, e.g., to the ear or intraocular for treatment of inflammation of the eye. The systemic administration of such stabilized peptides is contraindicated by virtue of their potential toxicity.

By replacing only specific positions in the "D-TAT" peptide by L-amino acids, peptides have been obtained with an intermediate half-live potentially more suitable for clinical development. The transporter constructs disclosed in the applications WO 2010/072406, WO 2010/072228 or WO2010/072275, comprising amino acid with both L- and D-amino acids are stable enough to prevent degradation by proteases prior to transport of the cargo moiety to its target site. Moreover, these transporter constructs appear not to permanently persist in the cell and are to some extent subject to protease degradation. Nevertheless, while effective transmembrane transporter activity has been demonstrated, it has been found that upon uptake, the cargo moiety of the cargo-transporter construct is not readily cleaved from the transporter moiety, which is generally a prerequisite for the cargo moiety to be biologically active. Moreover, it has been found that the degradation of the cargo-transporter construct is slow, such that is exhibits the tendency to accumulate in the target cell. Therefore, even if the attached cargo moiety is eventually released or is metabolized, the transporter construct may remain in the cell for a prolonged time and participate in further inter- and intracellular processes leading to unknown and unwanted side effects. Accordingly, there is a need to develop improved compounds for the intracellular delivery of desired cargo moieties.

3. SUMMARY OF THE INVENTION

The inventors have surprisingly discovered that specific consensus sequences of isolated peptides and/or polypeptides are able to effect specific binding to the proteoglycan C4S, which are selective to C4S relative to other proteoglycans (e.g., heparin, dermatan, keritan), which further exhibit improved in vivo stability relative to similarly sized peptides and which are able to function as improved carrier peptides/peptides for the cellular and intracellular delivery of molecules conjugated to them (e.g., by chemical conjugation or recombinant fusion). The peptides and or polypeptides having the polypeptides have the consensus sequences according to (i) or (ii), or the reverses thereof:

$$\text{Arg}_1\text{-}X_2\text{-}X_3\text{-}X_4\text{-}\text{Arg}_5\text{-}X_6\text{-}X_7\text{-}X_8\text{-}\text{Arg}_9\text{-}(\text{LD}_{10})_n\text{-}(\text{XD}_{11})_m, \text{ or} \quad (i)$$

$$(\text{XD}_{-2})_m\text{-}(\text{LD}_{-1})_n\text{-}\text{Arg}_1\text{-}X_2\text{-}X_3\text{-}X_4\text{-}\text{Arg}_5\text{-}X_6\text{-}X_7\text{-}X_8\text{-}\text{Arg}_9 \quad (ii)$$

wherein, (a) $\text{Arg}_1$, $\text{Arg}_5$, and $\text{Arg}_9$ represent L-arginine; $\text{LD}_{10}$ or $\text{LD}_{-1}$ represents any L- or D-amino acid other than D-arginine, D-lysine; L-arginine or L-lysine and n has a value of 0 to 10; wherein $\text{XD}_{11}$ or $\text{XD}_{-2}$ represents any D-amino acid other than D-arginine or D-lysine and m has a value of 0 or 1; and wherein the remaining amino acids $X_2$ to $X_4$ and $X_6$ to $X_8$ may be any L- or D-amino acid other than L-lysine, D-lysine, L-arginine or D-arginine, with the proviso that either $X_3$ or $X_7$, but not both, represents L-lysine or L-arginine;

or wherein, (b) $\text{Arg}_1$, $\text{Arg}_5$, and $\text{Arg}_9$ represent D-arginine; $\text{LD}_{10}$ or $\text{LD}_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1; and wherein the remaining amino acids $X_2$ to $X_4$ and $X_6$ to $X_8$ may be any L- or D-amino acid other than L-lysine, D-lysine, L-arginine or D-arginine, with the proviso that either $X_3$ or $X_7$, but not both, represents D-lysine or D-arginine.

Consensus sequence (i), above, with conditions (a) is SEQ ID NO:17, and with conditions (b) is SEQ ID NO:19. Consensus sequence (ii), above, with conditions (a) is SEQ ID NO:18, and with conditions (b) is SEQ ID NO:20.

The present inventors have further discovered that, as reflected in the consensus rules above, that the amino acid residues at positions 2, 4, 6, 8 and 3 (where position 7 is defined/selected according to rule (b)) or 7 (where position 3 is defined/selected according to rule (b)) do not contribute to the binding activity of the peptide. Therefore, the targeting moiety of the above peptides, represented by $Arg_1$-$X_2$-$X_3$-$X_4$-$Arg_5$-$X_6$-$X_7$-$X_8$-$Arg_9$ with the proviso that position 3 or 7 (but not both) is a lysine or arginine, can be seen to be to be identical for all possible peptides encompassed by the consensus sequences (with respect to the presentation of the side chains at 1, 5, 9, and 3 or 7, in 3D space). In fact, it is the 3D linear arrangement and/or 3D configuration of the arginine residues at positions 1, 5 and 9, together with the lysine or arginine at position 3 or 7 (but not both) that establishes the binding activity of the targeting moiety sequences and contributes the binding specificity and selectively for C4S relative to other proteoglycans. The remaining amino acid residues, i.e., positions 2, 4, 6, 8 and 3 (where position 7 is defined/selected according to rule (b)) or 7 (where position 3 is defined/selected according to rule (b)) serve primarily as a structural backbone to maintain the proper distance and relative configuration between the arginines at positions 1, 5 and 9, and the lysine or arginine at position 3 or 7 (but not both) of the targeting moiety. Thus, provided the 3D spatial orientation of these residues is maintained, in particular, the 3D presentation of the amino acid residue side chains, the peptide and/or compositions of the invention will exhibit specific and selective binding for a proteoglycan, in particular, C4S.

As such, the invention is generally drawn to isolated peptides and polypeptides comprising or consisting of the consensus sequences according to (i) or (ii) above, or to compounds comprising or consisting of such peptides and polypeptides, as well as to amino acid residue constructs (or compounds comprising them) having a 3D presentation of 3 arginine residues (i.e., $Arg_1$, $Arg_5$, and $Arg_9$) and the one arginine or lysine (i.e., $Arg/Lys_3$ or $Arg/Lys_7$ but not both) equivalent to the peptides and/or targeting moieties of consensus sequences (i) and (ii). Accordingly, the invention generally contemplates both the use of amino acid residues in the freely selectable positions (La, 2, 4, 6, 8 and 3 (where position 7 is defined/selected according to rule (b), above, as a D- or L-lysine or D- or L-arginine) or 7 (where position 3 is defined/selected according to rule (b), above, as a D- or L-lysine or D- or L-arginine)) in the targeting moiety of consensus sequences (i) and (ii), and the replacement of one or more of these residues with any appropriate chemical linker or chemical spacer suitable to maintain the equivalent spacing and the relative 3D orientation/presentation of the 3 arginine residues (i.e., $Arg_1$, $Arg_5$, and $Arg_9$) and the one arginine or lysine (i.e., $Arg/Lys_3$ or $Arg/Lys_7$ but not both). The invention encompasses molecules comprising or consisting of amino acid residues and also encompasses molecules comprising both amino acid residues and chemical linkers/spacers such that the molecules exhibit 3 arginines and 1 lysine or arginine in the same or an equivalent relative 3-dimensional confirmation as the arginines at positions 1, 5 and 9, and the lysine or arginine at position 3 or 7 (but not both) as in the targeting moieties of consensus sequences (i) and (ii). As used throughout this disclosure, a molecule comprising the replacement of one or more amino acid residues with a chemical Linker/spacer is termed a residue-spacer construct.

For the sake of convenience as used throughout this disclosure, the arginines in the residue-spacer construct that correspond to arginines 1, 5 and 9 of the consensus sequences (i) and (ii) will be referenced as Arg1, Arg5 and Arg9, respectively. Similarly the arginine or lysine in the residue-spacer construct that corresponds to the arginine or lysine at position 3 or 7 (but not both) of the consensus sequences (i) and (ii) of the peptides and compounds of the invention will be referenced as Arg/Lys3 or Arg/Lys7, respectively.

In view of the foregoing, the invention is generally directed to molecules wherein, Arg1 is linked to Arg5 via one or more chemical linkers (which may consist exclusively of one or more amino acid residues or may comprise both amino acid residues and chemical spacers/linkers), wherein the distance between Arg1 and Arg5 is 12.9±1.5 Å when the molecule/construct is in extended conformation; Arg5 is further linked to Arg9 via one or more chemical linkers (which may consist exclusively of one or more amino acid residues or may comprise both amino acid residues and chemical spacers/linkers), wherein the distance between Arg5 and Arg9 is 12.9±1.5 Å when the molecule/construct is in extended conformation. The linkages must be selected so that the final molecule Arg1-Arg5-Arg9 is a linear molecule when in extended conformation. The molecules of the invention further comprises either (1) an Arg/Lys3 within the one or more chemical linkers between Ar1 and Arg5, wherein the distance between Arg1 and Arg/Lys3 when the molecule is in extended conformation is about 7.5±1.5 Å; or (2) an Arg/Lys7 within the one or more chemical linkers between Arg5 and Arg9, wherein the distance between Arg9 and Arg/Lys7 when the molecule is in extended conformation is about 7.5±1.5 Å. Care must be taken when replacing one or more residues with chemical linkers according to the methods described herein so that the side chains of Arg1, Arg5, Ang9 and Arg/Lys3 or Arg/Lys7 retain the same or similar 3D presentation as their counterpart side chains in the peptide and polypeptides of consensus sequences (i) and (ii). Thus, the side chains of Arg1, Arg5, Ang9 and Arg/Lys3 or Arg/Lys7 within the residue-spacer construct should present in a linear or near linear arrangement within 3D space when the molecule/construct is in extended conformation. Thus, Arg1 and Arg9 will be separated by 25.8±3.0 Å when the molecule/construct is in extended position. In preferred embodiments, Arg1, Arg5, Ang9 and Arg/Lys3 or Arg/Lys7 are each either (i) an L-amino acid residue or (ii) a D-amino acid residue.

The invention is generally directed to at least one isolated molecule, or compounds comprising or consisting of said molecule, wherein the molecule has a consensus structure according to any one of (iii) to (vi), or the reverses thereof:

$$Arg_1\text{-}(SP_A)\text{-}Arg_5\text{-}(SP_B)\text{-}X\text{-}(SP_C)\text{-}Arg_9\text{-}(LD_{10})_n\text{-}(XD_{11})_m; \quad \text{(iii)}$$

$$Arg_1\text{-}(SP_C)\text{-}X\text{-}(SP_B)\text{-}Arg_5\text{-}(SP_A)\text{-}Arg_9\text{-}(LD_{10})_n\text{-}(XD_{11})_m; \quad \text{(iv)}$$

$$(XD_{-2})_m\text{-}(LD_{-1})_n\text{-}Arg_1\text{-}(SP_A)Arg_5\text{-}(SP_B)\text{-}X\text{-}(SP_C)\text{-}Arg_9; \text{ or} \quad \text{(v)}$$

$$(XD_{-2})_m\text{-}(LD_{-1})_n\text{-}Arg_1\text{-}(SP_C)\text{-}X\text{-}(SP_B)\text{-}Arg_5\text{-}(SP_A)\text{-}Arg_9 \quad \text{(vi)}$$

wherein, $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1;

wherein
- (a) $Arg_1$, $Arg_5$, and $Arg_9$ represent L-arginine; and X represents L-lysine or L-arginine, or
- (b) $Arg_1$, $Arg_5$, and $Arg_9$ represent D-arginine; and X represents D-lysine or D-arginine;

wherein ($SP_A$) represents a chemical linker that
- (a) consists of a peptide chain of 3 amino acid resides, wherein each residue may be independently selected from any amino acid residue other than D-arginine, D-lysine, L-arginine or L-lysine; or
- (b) separates the adjacent amino acid residues by 12.9±1.5 Å;

wherein ($SP_C$) represents a chemical linker that
- (a) consists of a single amino acid residue that may be any amino acid residue other than D-arginine, D-lysine, L-arginine or L-lysine; or
- (b) separates the adjacent amino acid residues by 7.5±1.5 Å when the molecule is in extended conformation;

and wherein ($SP_B$)-X-($SP_C$) or its reverse, ($SP_C$)-X-($SP_B$) represents a chemical linker
- (a) wherein $SP_B$ and $SP_C$ each represent a single amino acid residue that may be independently selected from any amino acid residue other than D-arginine, D-lysine, L-arginine or L-lysine; or
- (b) that separates the adjacent amino acid residues $Arg_1$ and $Arg_5$ or $Arg_5$ and $Arg_9$ by 12.9±1.5 Å when the construct is in extended conformation.

When replacing one or more amino acid residue with a chemical spacer/linker in the a consensus sequence (i) or (ii) (i.e., to form one or more of the molecules according to consensus structures (iii) to (vi)), care must be taken such that the side chains of Arg1, Arg5, Arg9 and Arg/Lys3 or Arg/Lys7 retain the same or similar 3D presentation as their counterpart side chains in the peptide and polypeptide consensus sequences (i) and/or (ii). Thus, the side chains of Arg1, Arg5, Ang9 and Arg/Lys3 or Arg/Lys7 within residue-spacer constructs according to the methods of the invention should present in a linear or near linear arrangement within 3D space when the molecule and/or construct is in extended conformation.

In certain embodiments the consensus structures (iii) to (vi) of the molecules of the invention do not comprise any chemical spacer/linkers, but comprises only amino acid residues. In such embodiments, the invention can be defined as directed to at least one isolated peptide or polypeptide, and/or to compounds comprising or consisting of at least one isolated peptide or polypeptide, which peptide or polypeptide has an amino acid sequence according to the following consensus sequence (i) or (ii), or the reverses thereof:

$$Arg_1\text{-}X_2\text{-}X_3\text{-}X_4\text{-}Arg_5\text{-}X_6\text{-}X_7\text{-}X_8\text{-}Arg_9\text{-}(LD_{10})_n\text{-}(XD_{11})_m, \text{ or} \quad \text{(i)}$$

$$(XD_{-2})_m\text{-}(LD_{-1})_n\text{-}Arg_1\text{-}X_2\text{-}X_3\text{-}X_4\text{-}Arg_5\text{-}X_6\text{-}X_7\text{-}X_8\text{-}Arg_9 \quad \text{(ii)}$$

wherein,
- (a) $Arg_1$, $Arg_5$, and $Arg_9$ represent L-arginine; $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1; and wherein the remaining amino acids $X_2$ to $X_4$ and $X_6$ to $X_8$ may be any L- or D-amino acid other than L-lysine, D-lysine, L-arginine or D-arginine, with the proviso that either $X_3$ or $X_7$, but not both, represents L-lysine or L-arginine;

or wherein,
- (b) $Arg_1$, $Arg_5$, and $Arg_9$ represent D-arginine; $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1; and wherein the remaining amino acids $X_2$ to $X_4$ and $X_6$ to $X_8$ may be any L- or D-amino acid other than L-lysine, D-lysine, L-arginine or D-arginine, with the proviso that either $X_3$ or $X_7$, but not both, represents D-lysine or D-arginine.

Consensus sequence (i), above, with conditions (a) is SEQ ID NO:17, and with conditions (b) is SEQ ID NO:19. Consensus sequence (ii), above, with conditions (a) is SEQ ID NO:18, and with conditions (b) is SEQ ID NO:20.

In certain embodiments the consensus structures (iii) to (vi) of the molecules of the invention comprise chemical linkers/spacers for $SP_A$, $SP_B$, and $SP_C$ that are not and do not comprise amino acid residues. In such embodiments, the invention can be defined as directed to at least one residue-spacer construct, or compounds comprising or consisting of them, wherein the construct has a consensus structure according to any one of (vii) to (x), or the reverses thereof:

$$Arg_1\text{-}(CL_A)\text{-}Arg_5\text{-}(CL_B)\text{-}X\text{-}(CL_C)\text{-}Arg_9\text{-}(LD_{10})_n\text{-}(XD_{11})_m; \quad \text{(vii)}$$

$$Arg_1\text{-}(CL_C)\text{-}X\text{-}(CL_B)\text{-}Arg_5\text{-}(CL_A)\text{-}Arg_9\text{-}(LD_{10})_n\text{-}(XD_{11})_m; \quad \text{(viii)}$$

$$(XD_{-2})_m\text{-}(LD_{-1})_n\text{-}Arg_1\text{-}(CL_A)Arg_5\text{-}(CL_B)\text{-}X\text{-}(CL_C)\text{-}Arg_9; \text{ or} \quad \text{(ix)}$$

$$(XD_{-2})_m\text{-}(LD_{-1})_n\text{-}Arg_1\text{-}(CL_C)\text{-}X\text{-}(CL_B)\text{-}Arg_5\text{-}(CL_A)\text{-}Arg_9 \quad \text{(x)}$$

wherein, $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1;

wherein
- (a) $Arg_1$, $Arg_5$, and $Arg_9$ represent L-arginine; and X represents L-lysine or L-arginine, or
- (b) $Arg_1$, $Arg_5$, and $Arg_9$ represent D-arginine; and X represents D-lysine or D-arginine;

wherein ($SP_A$) represents a chemical linker that separates the adjacent amino acid residues by 12.9±1.5 Å;

wherein ($SP_C$) represents a chemical linker that separates the adjacent amino acid residues by 7.5±1.5 Å when the molecule is in extended conformation;

and wherein ($SP_B$)-X-($SP_C$) or its reverse, ($SP_C$)-X-($SP_B$) represents a chemical linker that separates the adjacent amino acid residues $Arg_1$ and $Arg_5$ or $Arg_5$ and $Arg_9$ by 12.9±1.5 Å when the construct is in extended conformation.

When the molecule or compound of the invention comprises one or more chemical spacers/linkers that is not exclusively comprised of amino acid residues, care must be taken such that the side chains of Arg1, Arg5, Arg9 and Arg/Lys3 or Arg/Lys7 retain the same or similar 3D presentation as their counterpart side chains in the peptide and/or polypeptide consensus sequences (i) and/or (ii). Thus, the side chains of Arg1, Arg5, Ang9 and Arg/Lys3 or Arg/Lys7 within residue-spacer constructs according to the methods of the invention should present in a linear or near linear arrangement within 3D space when the molecule and/or construct is in extended conformation.

The molecules and compounds described above according to consensus sequences (iii) to (vi) (including certain embodiments comprising only amino acid residues according to consensus sequences (i) and (ii) and/or comprising chemical linkers and amino acid residues according to consensus structures (vii) to (x)) find particular use as transport and/or targeting moieties in the molecules and compounds described herein, specifically recognizing and/or binding proteoglycans, e.g., as expressed on the surface of a cell, in particular, binding the proteoglycan C4S selectively over other proteoglycans. The portion of the above consensus sequences (iii) to (vi) acting as the targeting moiety that specifically interact with the C4S proteoglycan is represented by $Arg_1$-($SP_A$)-$Arg_5$-($SP_B$)-X-($SP_C$)-$Arg_9$ or $Arg_1$-($SP_C$)-X-($SP_B$)-$Arg_5$-($SP_A$)-$Arg_9$ (including the specific embodiments having targeting moiety consensus sequences or structures $Arg_1$-$X_2$-$X_3$-$X_4$-$Arg_5$-$X_6$-$X_7$-$X_8$-$Arg_9$ (SEQ ID NO:21, where a fragment of SEQ ID NO:17 or SEQ ID NO:18; SEQ ID NO:22, where a fragment of SEQ ID NO:19 or SEQ ID NO:20), $Arg_1$-($CL_A$)-$Arg_5$-($CL_B$)-X-($CL_C$)-$Arg_9$ and $Arg_1$-($CL_C$)-X-($CL_B$)-$Arg_5$-($CL_A$)-$Arg_9$)) are identical molecules with respect to the 3D presentation of the amino acid residues corresponding to Arg1, Arg5, Arg9, and Arg/Lys3 or Arg/Lys7 and, in particular, the sides chains of these residues. Accordingly, any molecule comprising 3 arginine residues and one lysine residue according to consensus sequences (iii) to (vi) can be developed as the targeting moiety according to the following rules:

(1) Each of the residues Arg1, Arg5, and Arg9 must be the same optical isomer of arginine, i.e., each must be an L-arginine or each must be a D-arginine.

(2) Arg1 must be linked to Arg5 using one or more chemical spacers (which may consist exclusively of one or more amino acid residues or may comprise both amino acid residues and chemical spacers/linkers) such that they are separated by 12.9±1.5 Å when the molecule is in extended conformation; Arg5 must be further linked to Arg9 using one or more chemical spacers (which may consist exclusively of one or more amino acid residues or may comprise both amino acid residues and chemical spacers/linkers) such that they are also separated by 12.9±1.5 Å when the molecule is in extended conformation.

(3) The targeting moiety must also comprise one lysine or arginine residue in the linkage between Arg1 and Arg5 or between Arg5 and Arg9 (but not both) that is the same chirality as the Arg1, Arg5 and Arg9 (this residue corresponds to the residue as position 3 or 7 (but not both simultaneously) in consensus sequences (i) and (ii) and residue "X" in consensus sequences (iii) to (x)). In other words, where Arg1, Arg5 and Arg9 are L-arginine, the lysine/arginine must be a L-lysine or a L-arginine; and where Arg1, Arg5 and Arg9 are D-arginine, the lysine/arginine must be a D-arginine or a D-lysine.

(4) Where the lysine/arginine is positioned in the linkage between Arg1 and Arg5, it is separated from Arg1 by 7.5±1.5 Å; where the lysine/arginine is positioned in the linkage between Arg5 and Arg9, it is separated from Arg9 by 7.5±1.5 Å.

(5) The remaining linkages may comprise any chemical spacer or linker known in the art and/or described herein (which may consist exclusively of one or more amino acid residues or may comprise both amino acid residues and chemical spacers/linkers) suitable for maintaining the required separation of Arg1, Arg5, Arg9 and X as well as suitable to maintain a 3D orientation and/or 3/D presentation of amino acids and their side chains similar or the same as that in the corresponding residues in consensus sequences (i) and (ii). The linkages between Arg1, Arg5, Arg9 and X should preferentially not be positively charged. Where the linkages between Arg1, Arg5, Arg9 and X are amino acid residues or comprise amino acid residues, the residues can be any D- or L-amino acid other than D- or L-arginine or D- or L-lysine.

Where the consensus structures of the invention consist or comprise exclusively amino acids, the targeting moiety as described immediately above can be designed as follows. The sequence of the targeting moiety in consensus structures (iii) to (vi), where the structure consists or comprises exclusively amino acid residues is represented by $Arg_1$-$X_2$-$X_3$-$X_4$-$Arg_5$-$X_6$-$X_7$-$X_8$-$Arg_9$ (see, e.g., consensus sequences (i) and (ii)). The structure satisfies rule (2) above. That is, the linkage that separates Arg1 and Arg5 and that separates Arg5 and Arg9 by 12.9±1.5 Å when the molecule is in extended conformation that separates is a peptide consisting of 3 amino acid residues. The rules described immediately above as further applied to the peptide consensus sequence are:

(P1) Each of the residues Arg1, Arg5, and Arg9 must be the same optical isomer of arginine, i.e., each must be an L-arginine or each must be a D-arginine (corresponding to Rule (1), above).

(P2) Residue $X_3$ or $X_7$ (but not both) is a lysine or arginine of the same chirality as Arg1, Arg5 and Arg9. That is, where Arg1, Arg5 and Arg9 are L-arginine, $X_3$ or $X_7$ (but not both) must be a L-lysine or a L-arginine; and where Arg1, Arg5 and Arg9 are D-arginine, $X_3$ or $X_7$ (but not both) must be a must be a D-arginine or a D-lysine (corresponding to Rule 3 and 4, above).

(P3) The remaining residues, i.e., $X_2$, $X_4$, $X_6$, $X_8$ and $X_3$ (where $X_7$ is selected according to rule P2 immediately above) or $X_7$ (where $X_3$ is selected according to rule P2 immediately above) may be any amino acid other than L- or D-arginine or L- or D-lysine.

For all molecules and compounds of the invention, i.e., comprising or consisting of any of consensus sequences (iii) to (vi) (including embodiments (i), (ii), and (vii) to (x)) it is further preferred, but not necessary, that $LD_{10}$ or $LD_{-1}$ represents an L- or D-amino acid other than L- or D-arginine or L- or D-lysine and that $XD_{-11}$ or $XD_{-2}$ represents a D-amino acid other than D-arginine or D-lysine. It is most preferred that $LD_{-10}$ or $LD_{-1}$ represents L- or D-histidine and that $XD_{-11}$ or $XD_{-2}$ represents D-histidine.

Where the consensus structures of the invention consist or comprise exclusively amino acids (i.e., correspond to consensus sequences (i) or (ii)), it is preferred, but not necessary, that a D-amino acid is present at position 4 or position 6, i.e., at $X_4$ or $X_6$. In further preferred embodiments, the "freely selectable positions", i.e., 2, 4, 6, 8 and 3 (where position 7 is defined/selected according to rule (b), above, as a D- or L-lysine or D- or L-arginine) or 7 (where position 3 is defined/selected according to rule (b), above, as a D- or L-lysine or D- or L-arginine) are each independently selected from amino acids phenylalanine, tryptophan, valine, methionine, isoleucine and leucine. It is also preferred that no more than three of the freely selectable positions are alanine residues. Additionally, it is preferred that none of the freely selectable positions is a proline residue.

Non-limiting examples of peptides that may be used according to the methods disclosed herein and, in particular, as defined hereinabove are provided in Table 1.

TABLE 1

Exemplary Peptides Of The Invention*

| Sequence | |
|---|---|
| RSTqRYRVRh | (SEQ ID NO: 1) |
| RYFvRIKYRh | (SEQ ID NO: 2) |
| RYFvRIKARh | (SEQ ID NO: 3) |
| RAAvRAKYRh | (SEQ ID NO: 4) |
| RAAvRIKYRh | (SEQ ID NO: 5) |
| RSTqRYRVRh | (SEQ ID NO: 6) |
| RSTqRYKVRh | (SEQ ID NO: 7) |
| RGGgRGKGRh | (SEQ ID NO: 8) |
| RHHhRHKHRh | (SEQ ID NO: 9) |
| RVVvRVKVRh | (SEQ ID NO: 10) |
| RLLlRLKLRh | (SEQ ID NO: 11) |
| RMMmRMKMRh | (SEQ ID NO: 12) |
| RIIiRIKIRh | (SEQ ID NO: 13) |
| RYFVRiKYRh | (SEQ ID NO: 25) |
| RSTqRYRVR | (SEQ ID NO: 26) |
| RYFvRIKYR | (SEQ ID NO: 15) |
| RYFvRIKAR | (SEQ ID NO: 27) |
| RAAvRAKYR | (SEQ ID NO: 28) |
| RAAvRIKYR | (SEQ ID NO: 29) |
| RSTqRYRVR | (SEQ ID NO: 30) |
| RSTqRYKVR | (SEQ ID NO: 31) |
| RGGgRGKGR | (SEQ ID NO: 32) |
| RHHhRHKHR | (SEQ ID NO: 33) |
| RVVvRVKVR | (SEQ ID NO: 34) |
| RLLlRLKLR | (SEQ ID NO: 35) |
| RMMmRMKMR | (SEQ ID NO: 36) |
| RIIiRIKIR | (SEQ ID NO: 37) |
| RYFVRIKYR | (SEQ ID NO: 14) |
| RYFVRiKYR | (SEQ ID NO: 16) |

*lower case indicates D-enantiomer; upper case indicates L-enantiomer

In addition the peptides, polypeptides and compounds comprising or consisting of the peptides according to the consensus sequences (i) or (ii), the invention further encompasses variants of the exemplary peptide sequences explicitly disclosed herein. Such variants comprise substitution of the freely selectable positions, i.e., substitution at positions 2, 4, 6, 8 and 3 (where position 7 is defined/selected according to rule (b), above, as a D- or L-lysine or D- or L-arginine) or 7 (where position 3 is defined/selected according to rule (b), above, as a D- or L-lysine or D- or L-arginine), with a conservative amino acid substitution. As is well known in the art, "conservative substitutions" are substitutions with another amino acid having similar characteristics, e.g., small amino acids substituted for small amino acids, acidic amino acids substituted for acidic amino acids, etc., for any characteristic class of amino acids e.g., polar amino acids, basic amino acids, hydrophobic amino acids and aromatic amino acids. Preferred substitutions for a particular residue according to the present invention may be chosen from among the other members of its conservative substitution group. Six conservative substitution groups are commonly recognized in the art: (1) alanine (A), glycine (G) serine (S) and threonine (T); (2) aspartic acid (D) and glutamic acid (E); (3) asparagine (N) and glutamine (Q); (4) arginine (R), histidine (H) and lysine (K); (5) isoleucine (I), leucine (L), methionine (M) and valine (V); and (6) phenylalanine (F), tyrosine (Y) and tryptophan (W).

However, the substitutions in the freely selectable positions of any peptide sequence according to consensus sequences (i) and (ii) expressly disclosed herein need not be made with a member of its conservative substitution group. The invention also contemplates the substitution of any residue at a freely selectable position, i.e., 2, 4, 6, 8 and 3 (where position 7 is defined/selected according to rule (P2), above, as a D- or L-lysine or D- or L-arginine) or 7 (where position 3 is defined/selected according to rule (P2), above, as a D- or L-lysine or D- or L-arginine), with any other L- or D-amino acid other than L- or D-arginine or L- or D-lysine subject to the rules of the consensus sequences outlined herein. As detailed herein, the non-defined positions do not substantially contribute to targeting effects.

In all embodiments of the invention, use of the amino acid proline (P) in any consensus sequences (i) to (x), e.g., in any of the chemical linkers/spacers defined therein, should be avoided as it is believed that this residue would destroy or sufficiently distort the 3-dimensional conformation of the molecule or peptide so as to significantly reduce binding activity or affinity.

Any appropriate chemical linker or chemical spacer suitable to maintain the spacing and the relative 3D orientation/presentation of the 3 arginine residues (i.e., $Arg_1$, $Arg_5$, and $Arg_9$) and the one arginine or lysine (i.e., $Arg/Lys_3$ or $Arg/Lys_7$ but not both) equivalent to the corresponding residues in consensus sequences (i) and (ii) known in the art or described herein may be used in the construction of the molecules of the invention according to consensus structures (iii) to (vi) (including the embodiments having any of consensus structures (vii) to (x)). Nonlimiting examples of appropriate chemical linkers/spacers include beta- and gamma-peptides; sugar amino acid based scaffolds; beta-hairpin peptidometics including, but not limited to X, X, and X); alpha-helical mimetic, beta-sheet/beta-stand mimetics and beta-turn mimetics and cyclotides. In preferred embodiments, the chemical linker/spacers are not positively charged. The linkers should be subject to metabolic breakdown, non-toxic (including metabolites) and should not significantly reduce the solubility of the compounds of the invention.

It is expressly contemplated that the embodiments described throughout this application, whether identified as preferred (including most preferred) or not, can be independently implemented and/or can be combined with the other disclosed embodiments in the design or selection of a peptide of the invention. Therefore, a sequence or structure of the targeting moiety of the peptide, polypeptide, molecule or compound of the invention must satisfy the rules (1) to (5) listed above, and may optionally satisfy none, one, or more than one of the conditions outlined in the other embodiments disclosed herein whether preferred or not.

The invention may comprise the isolated molecules and compounds (including isolated molecules, peptides, polypeptides and compounds comprising or consisting of the molecules, peptides and/or polypeptides) according to consensus sequences (iii) to (vi) (including embodiments according to consensus sequences (i) and (ii) and consensus structures (vii) to (x)) and may further comprise a biologically active moiety (BAM; also referenced as the "cargo" of the targeting moiety). The (BAM)-(targeting moiety) construct may also be referenced as a BAM-conjugate of the invention throughout the disclosure. The BAM may be chemically conjugated to the compounds, peptides, polypeptides and/or molecules of the invention directly and/or may be linked thereto through a linker group.

As used throughout the disclosure, direct conjugation indicates the conjugation of the BAM moiety to any amino acid residue within consensus sequences (iii) to (vi) (including embodiments according to consensus sequences (i) and (ii) and consensus structures (vii) to (x)), or to any amino acid residue or suitable chemical group therein, using any chemical coupling known in the art or described herein suitable for the conjugation of the BAM moiety to an amino acid residue (e.g., an amino acid side chain) and/or chemical group. Accordingly, direct coupling may result in one or more chemical groups spaced between the BAM moiety and the amino acid (e.g., amino acid side chain) or chemical group of the residue-spacer construct, which groups form as a result of the coupling reaction as is known in the art.

Alternatively, as described herein, the BAM moiety may be conjugated to any amino acid residue or chemical group within consensus sequences (iii) to (vi) (including embodiments according to consensus sequences (i) and (ii) and consensus structures (vii) to (x)), indirectly, that is, via a linker group. Therefore, as used throughout this disclosure, indirect conjugation means that the BAM is conjugated to the linker group, which linker group is conjugated to an amino acid residue or chemical group within a consensus sequence as defined herein. The conjugation between the BAM and the linker group and between the linker group and an amino acid residue or chemical group of consensus sequences (iii) to (vi) (including embodiments according to consensus sequences (i) and (ii) and consensus structures (vii) to (x)), may be any conjugation method and/or compound suitable for effecting such conjugation as described herein or as is otherwise known in the art.

The direct or indirect conjugation of the BAM moiety may be directed to any amino acid residue or chemical linker/spacer group within molecules of the invention. Thus, the BAM moiety may be directly or indirectly conjugated to an amino acid residue that is at the N or C terminus of consensus sequence (iii) to (vi) (including embodiments according to consensus sequences (i) and (ii) and consensus structures (vii) to (x)). Alternatively or additionally, the BAM moiety may be directly or indirectly conjugated to an internal amino acid residue or chemical linker/spacer group within molecules of the invention. As used throughout this disclosure, an internal residue or internal chemical group references an amino acid residue or chemical group of consensus sequence (iii) to (vi) (including embodiments according to consensus sequences (i) and (ii) and consensus structures (vii) to (x)) that is not at the terminus of the linear peptide chain or linear residue-spacer construct. As is known in the art, conjugation methods (whether direct or indirect) may require the chemical modification of one or both sites of conjugation (e.g., modification of an amino acid residue, modification of a chemical group within the molecule of the invention and/or modification of the BAM moiety). Accordingly, the present invention also encompasses chemical modification of the molecules of the invention, compounds comprising or consisting of the molecules and/or conjugate components.

In preferred embodiments, the compounds of the invention comprise or consist of a peptide-conjugate, e.g., a BAM-conjugate, having a BAM conjugated at the terminus of a consensus sequence or structure (i) to (x) as described herein. Therefore, in these preferred embodiments, the BAM-conjugate has a consensus structure according to the following consensus structures (xi) to (xiv), or the reverses thereof:

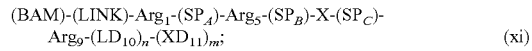

(BAM)-(LINK)-Arg$_1$-(SP$_A$)-Arg$_5$-(SP$_B$)-X-(SP$_C$)-Arg$_9$-(LD$_{10}$)$_n$-(XD$_{11}$)$_m$; (xi)

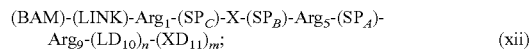

(BAM)-(LINK)-Arg$_1$-(SP$_C$)-X-(SP$_B$)-Arg$_5$-(SP$_A$)-Arg$_9$-(LD$_{10}$)$_n$-(XD$_{11}$)$_m$; (xii)

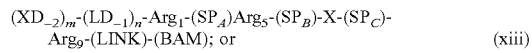

(XD$_{-2}$)$_m$-(LD$_{-1}$)$_n$-Arg$_1$-(SP$_A$)Arg$_5$-(SP$_B$)-X-(SP$_C$)-Arg$_9$-(LINK)-(BAM); or (xiii)

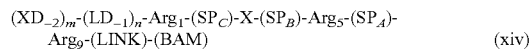

(XD$_{-2}$)$_m$-(LD$_{-1}$)$_n$-Arg$_1$-(SP$_C$)-X-(SP$_B$)-Arg$_5$-(SP$_A$)-Arg$_9$-(LINK)-(BAM) (xiv)

(BAM) represents a biologically active moiety; wherein (LINK) represents an optional linker group; wherein, LD$_{10}$ or LD$_{-1}$ represents any L- or D-amino acid and n has a value of 0 to 10; wherein XD$_{11}$ or XD$_{-2}$ represents any D-amino acid and m has a value of 0 or 1;

wherein
(a) Arg$_1$, Arg$_5$, and Arg$_9$ represent L-arginine; and X represents L-lysine or L-arginine, or
(b) Arg$_1$, Arg$_5$, and Arg$_9$ represent D-arginine; and X represents D-lysine or D-arginine;

wherein (SP$_A$) represents a chemical linker that
(a) consist of a peptide chain of 3 amino acid resides, wherein each residue may be independently selected from any amino acid residue other than D-arginine, D-lysine, L-arginine or L-lysine; or
(b) separates the adjacent amino acid residues by 12.9±1.5 Å;

wherein (SP$_C$) represents a chemical linker that
(a) consists of a single amino acid residue that may be any amino acid residue other than D-arginine, D-lysine, L-arginine or L-lysine; or
(b) separates the adjacent amino acid residues by 7.5±1.5 Å when the molecule is in extended conformation;

and wherein (SP$_B$)-X-(SP$_C$) or its reverse, (SP$_C$)-X-(SP$_B$) represents a chemical linker
(a) wherein SP$_B$ and SP$_C$ each represent a single amino acid residue that may be independently selected from any amino acid residue other than D-arginine, D-lysine, L-arginine or L-lysine; or
(b) that separates the adjacent amino acid residues Arg$_1$ and Arg$_5$ or Arg$_5$ and Arg$_9$ by 12.9±1.5 Å when the construct is in extended conformation.

Consensus sequences (xi) to (xiv) are identical to consensus sequences (iii) to (vi), respectively, but for the presence of the BAM-moiety and the optional linker group, (LINK). Therefore, selection of the chemical spacers (SP$_A$), (SP$_B$) and (SP$_C$), which may consist of or comprise exclusively amino acid residues or comprise both chemical linkers and amino acid residues as described herein) proceeds as described herein with respect to consensus sequences (iii) to (vi), including selection of these chemical spacers to consist of or comprise exclusively amino acid residues according to the embodiments (and combinations thereof) of consensus sequences (i) and (ii) as detailed throughout this disclosure, and selection of these chemical spacers to comprise both chemical linkers and amino acid residues according to the embodiments (and combinations thereof) of consensus structures (vi) to (x) as detailed throughout this disclosure.

Where a linker group is present, (e.g., (LINK) in consensus structures (xi) to (xiv)) and/or a linker group used in the indirect linkage of the BAM to an amino acid residue or to a chemical group in any of consensus sequences/structures (i) to (x), such linker may be any linker, e.g., a peptide linker, known in the art or disclosed herein suitable for linking the BAM to the remaining targeting moiety. The BAM may be chemically conjugated to the linking group, or, for example, where both the linking group, (e.g., (LINK) of structures (xi) to (xiv)), and the BAM are peptides or polypeptides, the BAM may be linked to the linking group via a peptide bond and the linking group may also be linked to the targeting moiety of the consensus sequence/structure via a peptide bond. Non-limiting examples of linker groups include peptide linkers, e.g., comprising one or more residues of glutamic acid, glycine, serine, cysteine and combinations thereof. In certain embodiments, the linking group (LINK) of structures (xi) to (xiv) is a single amino acid that is L- or D-glutamic acid.

The invention also encompasses molecules and compounds comprising or consisting of the molecules, e.g., peptide-conjugates/residue-spacer-conjugates/BAM-conjugates, that do not comprise a linking group, i.e., consensus structures (xi) to (xiv) lacking the (LINK) moiety and/or direct linkage of the BAM moiety to any amino acid residue or chemical group within any consensus sequence/structure (i) to (x). Where the BAM-conjugate of the invention is lacking the linking group, the BAM may be conjugated, e.g., chemically conjugated, directly to the molecules' amino acid residue or chemical group (e.g., a chemical group of the chemical linker). Non-limiting examples of such chemical conjugation include covalent attachment to the molecule at the N-terminus and/or to the N-terminal amino acid residue via an amide bond or at the C-terminus and/or C-terminal amino acid residue via an ester bond. Where the BAM is a peptide or polypeptide, the BAM may be directly conjugated to the N-terminus and/or N-terminal amino acid or to the C-terminus and/or C-terminal amino acid via a peptide bond.

The invention encompasses any BAM expected to exert a therapeutically relevant activity on administration to an organism or on delivery to one or more cells of an organism, whether in vitro or in vivo. Accordingly, non-limiting examples of BAMs encompassed by the invention include mono- and poly-saccharides, cytotoxic agents, antineoplastic agents, anti-inflammatory agents, anti-viral agents, antibacterial agents, and agents for the treatment of protozoan infections. The BAM may also be a deoxyribose or ribose.

Non-limiting examples of anti-neoplastic agents that may be used as BAMs according to the methods of the invention include, but are not limited to, aldesleukin, alemtuzumab, alitretinoin, allopurinol, altretamine, amifostine, anastrozole, abiraterone, arsenic, axitinib, azacitidine, bendamustine, bexarotene, bleomycin, bortezomib, busulfan, cabazitaxel, calusterone, capecitabine, carboplatin, carfilzomib, carmustine, carmustine, celecoxib, chlorambucil, cisplatin, cladribine, clofarabine, crizotinib, cyclophosphamide, cytarabine, dacarbazine, dactinomycin, actinomycin D, dasatinib, daunorubicin, decitabine, dexrazoxane, docetaxel, doxorubicin, entinostat, epirubicin, eribulin, erlotinib, estramustine, etoposide, everolimus, exemestane, fostamatinib, floxuridine, fludarabine, fluorouracil, 5-FU, fulvestrant, gefitinib, gemcitabine, hydroxyurea, idarubicin, lenalidomide, ifosfamide, imatinib, lomustine, irinotecan, isotretinoin, ixabepilone, lapatinib, lenalidomide, letrozole, leucovorin, levamisole, lomustine, CCNU, marizomib, meclorethamine, nitrogen mustard, melphalan, L-PAM, mercaptopurine, 6-MP, mertansine, mesna, methotrexate, methoxsalen, mitomycin, mitotane, mitoxantrone, nandrolone, nelarabine, nilotinib, oxaliplatin, paclitaxel, pamidronate, pazopanib, pegademase, pemetrexed, pentostatin, pipobroman, plerixafor, plicamycin, mithramycin, porfimer, pralatrexate, procarbazine, quinacrine, rapamycin, romidepsin, ruxolitinib, sorafenib, streptozocin, sunitinib, tamoxifen, temozolomide, temsirolimus, teniposide, VM-26, testolactone, thalidomide, thioguanine, 6-TG, thiotepa, topotecan, toremifene, tretinoin, ATRA, uracil mustard, valrubicin, vandetanib, vemurafenib, verteporfin, vinblastine, vincristine, vinorelbine, vismodegib, vorinostat, zoledronate, nucleoside analogues AZT, b-D-arabinofuranose, vidarabine, 2-chlorodeoxyadenosine, intercalating drugs, kinase inhibitors, cofarabine, laromustine, clophosphamide, asparaginase, dexamethasone, prednisone and lestaurtinib. The above-listed anti-neoplastic agents may be used in accordance with the methods disclosed herein not only in connection with neoplastic diseases, but also in the treatment, prevention and/or amelioration of other diseases, or symptoms thereof, as is known in the art, e.g., in connection with the treatment, prevention and/or amelioration of anti-inflamatory or autoimmune diseases, and/or symptoms thereof.

Examples of anti-inflammatory agents that may be used as BAMs according to the methods of the invention include, but are not limited to, COX-2 inhibitors, prednisone, pazopanib, famotidine, dalfampridine, pegloticase, esomeprazole, aspirin, celecoxib, diclofenac, valdecoxib, rofecoxib, diflunisal, etodolac, fenoprofen, flurbiprofen, ibuprofen, indomethacin, ketoprofen, ketorolac, mefenamic acid, meloxicam, nabumetone, naproxen, oxaprozin, piroxicam, sulindac, tolmetin, lansoprazole, meclofenamate, triamcinolone, methylprednisolone, betamethasone, budesonide, prednisolone, hydrocortisone, dexamethasone and cortisone.

Examples of anti-protozoal agents that may be used as BAMs according to the methods of the invention include, but are not limited to, chloroquine, mefloquine, primaquine, proguanil hydrochloride, proguanil hydrochloride with atovaquone, pyrimethamine, sulfadoxine, quinine, quinoline, doxycycline, clindamycin, artesunate, diloxanide, metronidazole, tinidazole, mepacrine hydrochloride, amphotericin, pentamidine, pyrimethamine, sulfadiazine, azithromycin, atovaquone, trimethoprim-sulphamethoxazole, trimethoprim, dapsone, atovaquone, pentamidine isetionate, amodiaquine, chloroguanide, eflornithine, hydroxychloroquine, iodoquinol, meglumine antimonate, melarsoprol, nifurtimox, paromomycin, sodium stibogluconate, suramin, and tryparsamide.

As detailed herein, the compounds of the invention comprise or consist of a BAM-conjugate (i.e., a BAM conjugated to the targeting moiety; also referenced as a peptide-conjugate) that may effect intracellular transport of the BAM. Accordingly, in preferred embodiments, the invention encompasses a pharmaceutical composition comprising a compound of the invention, e.g., a BAM-conjugate, and a pharmaceutically acceptable carrier. The pharmaceutical compositions of the invention comprising, e.g., the BAM-conjugate, may be used for any indication known or predicted to be treatable with the BAM. For example, where the BAM is an anti-viral agent, the pharmaceutical composition comprising the BAM conjugate may be used in the treatment of a viral infection, or the symptom thereof, including but not limited to HIV; Epstein Barr virus; morbillivirus; paramyxovirus; rubivirus; herpes virus; dengue virus; herpes simplex virus; parvovirus; respiratory syncytial virus; variola virus; varicella; flavivirus; human T-lymphotropic virus; hepatitis virus A, B, C, D or E, lassa virus and/or influenza virus. Where the BAM is an anti-protozoal agent, the pharmaceutical composition comprising the BAM-conjugate may be used in the treatment of protozoal infections, such as leshmaniasis and/or malaria.

The targeting moieties of consensus sequences/structures (i) to (xiv) interact specifically with proteoglycans, in particular, chondroitin-4-sulfate (C4S). C4S is preferentially expressed in connection with certain cell surface markers, e.g., CD68, and preferentially expressed, relative to other proteoglycans, by certain cell types, e.g., leukocytes and myelocytes. Accordingly, the invention encompasses the use of the molecules and compounds, e.g., BAM-conjugates, to specifically target cells expressing CD68 and/or C4S. The invention encompasses the use of the molecules and compounds, e.g., BAM-conjugates, to facilitate transport of the BAM moiety into cells expressing CD68 and/or C4S, such as myelocytes and leukocytes.

The molecules and compounds of the invention (including isolated molecules peptides, polypeptides and compounds comprising or consisting of any of consensus sequences (i) to (xiv)) find particular use in the targeting of leukocytes and/or myleocytes and, thus, may find particular use in the treatment, prevention or amelioration of symptoms associated with diseases or conditions in which leukocytes have a pathophysiological involvement. Nonlimiting examples of such diseases or conditions include neutrophilia, neutropenia, leukopenia, basopenia, basophilia, eosinopenia, eosinophilia, idiopathic hypereosinophilic syndrome, lymphocytic leukocytosis, lymphocytosis, lymphocytopenia, monocytosis, monocytopenia, May Hegglin Anomaly, Pelger-Huet Anomaly, Alder-Reilly Anomaly, Chedial-Higashi syndrome, Job's syndrome (hyper-IgE), lazy leukocyte syndrome, congenital C3 deficiency, chronic granulomatous disease, leukocyte, glucose-6-phosphate dehydrogenase deficiency, myeloperoxidase deficiency-benign, severe combined immunodeficiency disease, DiGeorge's syndrome, Nezelof's syndrome, infantile sex-linked agammaglobulinemia, common variable hypogammaglobulinemia, mucopolysaccharidosis, lipodoses, Gaucher disease, Niemann-pick disease, Fabry disease, Farber's disease, gangliosidoses; Tay Sachs, Sandhoff disease, Krabbe disease, metachromatic leukodystrophy, Wolman's disease, leukemia, acute lymphocytic leukemia (L1, L2, L3), chronic lymphocytic leukemia, all forms of acute myelogenous leukemia (AML), including undifferentiated AML (M0), myeloblastic leukemia (M1), myeloblastic leukemia, (M2), promyelocytic leukemia, (M3), myelomonocytic leukemia (M4), monocytic leukemia (M5), erytholeukemia (M6), megakaryoblastic leukemia, (M7), chronic myelogenous leukemia as well as undifferentiated or biphenotypic acute leukemias (leukemias that have both lymphocytic and myeloid features), and all forms of lymphomas including Hodgkin lymphoma, T-cell lymphoma, B-cell lymphoma, lymphoplasmacytic lymphoma, Waldenström macroglobulinemia, multiple myeloma, and follicular lymphoma.

4. DEFINITIONS

The term "diseases or conditions in which leukocytes have a pathophysiological involvement" and analogous phrases as used herein refers to: i) conditions, where the etiology of the disease lies primarily within the myeloid or lymphoid cells, such as malignant transformations, including all forms of leukemia as well as nonmalignant leukocyte disorders, including genetic disorders of leukocyte function; ii) secondary disorders of leukocyte function resulting from toxic challenge, or resulting from viral, bacterial, protozoan or other parasitic infections of the leukocyte; or iii) by virtue of the ubiquitous involvement of leukocytes in inflammation and the immune response in general, such as in diseases and conditions or symptoms thereof, which are neither primarily nor secondarily caused or by leukocytes, but which may be treated, prevented, attenuated or ameliorated by modulating (stimulating or inhibiting) leukocyte activity.

The term "chemical derivatives" as used herein refers to the (chemical) modification of amino acids, amino acid side chains and peptide bonds (including those at the N-terminus, the C-terminus, within the backbone of the consensus structure/sequence) as well as modification of any chemical group within the chemical spacer/linker of consensus structures (iii) to (xiv). The term does not intend to refer to any addition, substitution or deletion of amino acids residues in an amino acid or peptide chain. Chemical derivatives from L-amino acids or L-enantiomeric amino acids typically comprise any naturally or non-naturally occurring derivative of these amino acids, including, without being limited thereto, amino acids as defined above comprising post-translational modifications or synthetic modifications, including acetylation (at the N-terminus of the (poly-)peptide sequence, at lysine residues, etc.), deacetylation, alkylation, such as methylation, ethylation, etc. (preferably at lysine or arginine residues within the (poly-)peptide sequence), dealkylation, such as demethylation, deethylation, etc., amidation (preferably at the C-terminus of the (poly-)peptide sequence), formylation, gamma-carboxylation, glutamylation, glycosylation (preferably at asparagine, lysine, hydroxylysine, serine or threonine residues, etc., within the (poly-)peptide sequence), addition of a heme or haem moiety, hydroxylation, iodination, isoprenylation addition of an isoprenoid moiety such as farnesyl or geranylgeraniol, etc.), lipoylation (attachment of lipoate functionality), such as prenylation, formation of a GPI anchor, including myristoylation, farnesylation, geranylgernaylation, etc., oxidation, phosphorylation (e.g. to a serine, tytosine, threonine or a histidine moiety, etc., within the (poly-)peptide sequence), sulfation (e.g., of tyrosine), selenoylation, sulfation, etc. Chemical derivatives of amino acids also include, without being limited thereto, modified amino acids, which have been modified by introducing a label, including radioactive labels, a dye or fluorescent group, or a chemoluminesent group.

As used herein, the term "freely selectable positions", "freely selectable amino acids" and analogous terms references the positions within the targeting moiety of the embodiments encompassing consensus sequences (i) and (ii) that are not explicitly defined. The targeting moiety of consensus sequences (i) and (ii) is represented by $Arg_1$-$X_2$-$X_3$-$X_4$-$Arg_5$-$X_6$-$X_7$-$X_8$-$Arg_9$, wherein $Arg_1$, $Arg_5$, and $Arg_9$ represent D- or L-arginine (all of the same chirality), and wherein the remaining amino acids $X_2$ to $X_4$ and $X_6$ to $X_8$ may be any L- or D-amino acid other than L-lysine, D-lysine, L-arginine or D-arginine, with the proviso that $X_3$ or $X_7$, but not both, is a lysine or arginine having the same chirality as $Arg_1$, $Arg_5$, and $Arg_9$. Thus, there are 5 freely selectable positions of consensus sequences (i) and (ii), which are $X_2$, $X_4$, $X_6$, $X_8$ and either $X_3$ (where position $X_7$ is defined/selected as a D- or L-lysine or D- or L-arginine) or $X_7$ (where position 3 is defined/selected as a D- or L-lysine or D- or L-arginine). As further defined herein, the invention also encompasses the replacement of the freely-selectable amino acids with chemical spacers (which may also include amino acid residues) to form the residue-spacer constructs such that the relative 3D orientation of three arginines and one lysine or arginine is equivalent to that of $Arg_1$, $Arg_5$ and $Arg_9$ and Arg/Lys at position 3 or 7 (but not both) of consensus sequences (i) and (ii) termed a residue-spacer construct throughout). The chemical spacers/linkers that may replace the freely selectable amino acid in the molecules of the invention (e.g., a residue-spacer construct) are presented by ($SP_A$), ($SP_B$), and ($SP_C$) in consensus structures (iii) to (vi) and (xi) to (xiv) and by ($CL_A$), ($CL_B$) and ($CL_C$) in consensus structures (vii) to (x).

In the context of the present invention, L-amino acids, also known in the art and referenced herein as L-enantiomeric amino acids, are preferably amino acids selected from natively occurring amino acids or their derivatives. Naturally occurring amino acids are recognized as the standard (proteinogenic) amino acids alanine, arginine, asparagine, aspartic acid, cysteine, glutamine, glutaminic acid, glycine, histidine, isoleucine, leucine, lysine, methionine, phenyl alanine, proline, serine, threonine, tryptophane, tyrosine, and valine, but also include non-standard amino acids such as ornithine, citrulline, homocysteine, S-adenosyl methionine, hydroxyproline, selenocysteine, pyrolysine, lanthionine, 2-aminoisobutyric acid, dehydroalanine, and gamma-aminobutyric acid.

Similarly, in the context of the present invention, D-amino acids, also known in the art and referenced herein as D-enantiomeric amino acids, are preferably non-native (non-proteinogenic) "retro-inverso" amino acids, wherein these non-native (non-proteinogenic) "retro-inverso" amino acids are recognize derived from naturally occurring L-amino acids and/or their derivatives as defined above. In this context, the term "retro-inverso" refers to an isomer of a naturally occurring L-amino acid as defined above (and peptides made therefrom) in which the chirality of the naturally occurring L-amino acid residue is inverted in the corresponding D-amino acid. In other words, in the peptide bonds of D-amino acids the positions of carbonyl and amino groups are exchanged, while the position of the side-chain groups at each alpha carbon is preserved. Accordingly, D-amino acids may be inserted into a peptide sequence consisting of or comprising L-amino acids and therefore may be conjugated with L-amino acids as defined above by methods known in the art or defined herein.

The amino acids abbreviations used in the present disclosure are shown in the following Table of Correspondence. As used throughout the present disclosure and as detailed in the following table, upper-case or a capital letter in the 1 letter symbol references a L-amino acid, while a lowercase 1 letter symbol references a D-amino acid.

| Symbol | | | |
|---|---|---|---|
| 1-Letter | | | |
| L-amino acid | D-amino acid | 3-Letter | Amino acid |
| A | a | Ala | Alanine |
| R | r | Arg | Arginine |
| N | n | Asn | Asparagine |
| D | d | Asp | Aspartic acid |
| C | c | Cys | Cysteine |
| E | e | Glu | Glutamic acid |
| Q | q | Gln | Glutamine |
| G | g | Gly | Glycine |
| H | h | His | Histidine |
| I | i | Ile | Isoleucine |
| L | l | Leu | Leucine |
| K | k | Lys | Lysine |
| M | m | Met | Methionine |
| F | f | Phe | Phenylalanine |
| P | p | Pro | Proline |
| S | s | Ser | Serine |
| T | t | Thr | Threonine |
| W | w | Trp | Tryptophan |
| Y | y | Tyr | Tyrosine |
| V | v | Val | Valine |
| X | x | Xaa | Unknown or other |

The term "Leukocytes" as used herein refers to any type of white blood cell as defined herein or as known in the art. The term also encompasses precursor cells and/or different developmental stages of white blood cells. The term "leukocytes" typically includes granulocytes, lymphocytes, monocytes, macrophages, dendritic cells, mast cells and/or microglial cells. Granulocytes include, but are not limited to, neutrophils, eosinophils and basophils. Lymphocytes include, but are not limited to, NK cells, Helper T cells, cytotoxic T cells, γδ T cells, and B cells.

As used herein, the term "peptides", "polypeptides" and "proteins" have their meaning as generally understood as in the art, i.e., referring to a chain of amino acids. However, the terms shall not be construed as limiting the length of the amino acid chain.

5. BRIEF DESCRIPTION OF FIGURES

FIG. 1 Representation of TAT peptide (left molecule) and C4S (right molecule) in extended conformation, indicating calculated distances between certain chemical groups according to model predictions.

Figure 2:
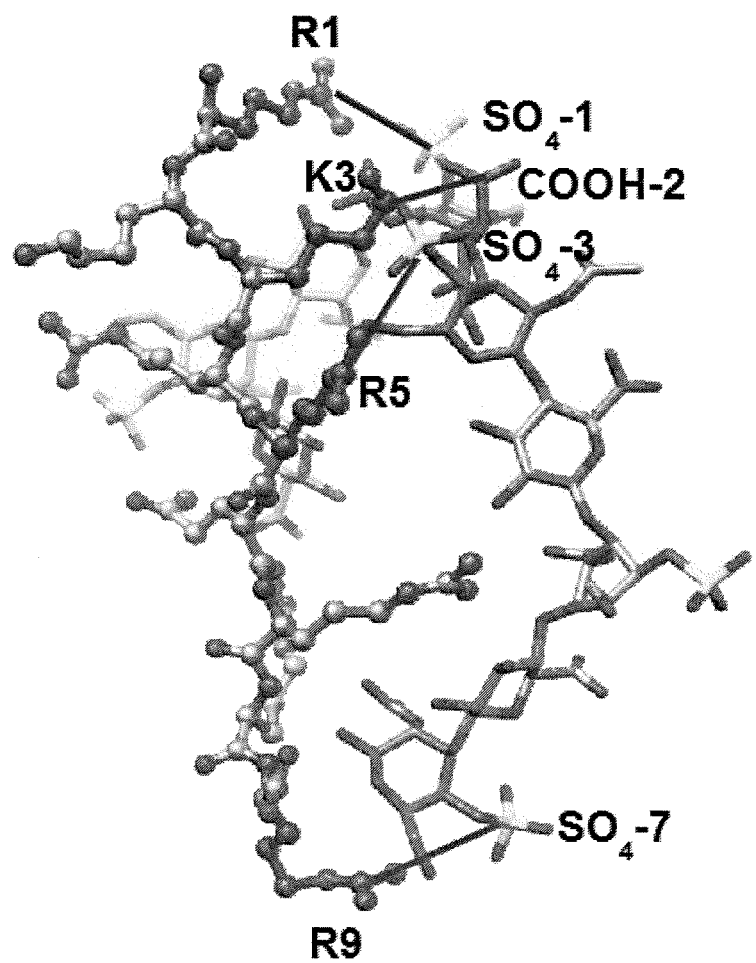

FIG. 2 Three-dimensional representation of the modeling of the interaction between the targeting moieties (i.e., the nine-mer peptide) according to the invention (left molecule) and the C4S proteoglycan (right molecule).

Figure 3:
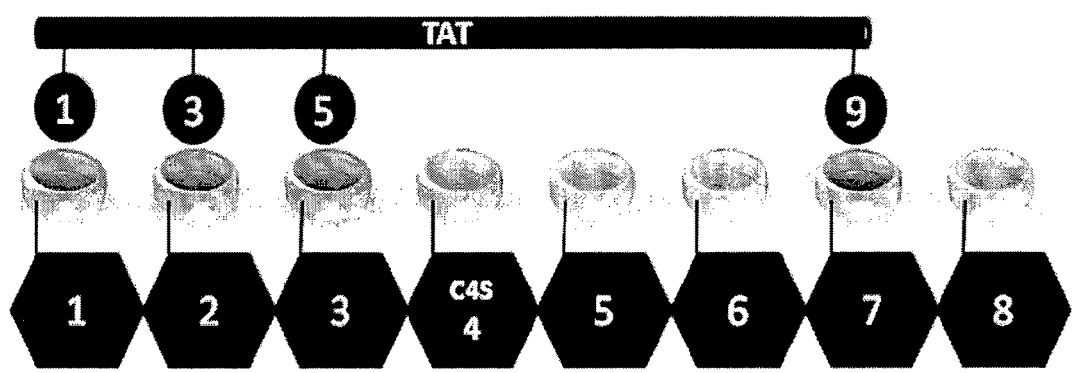

FIG. 3 Schematic representation of interaction between C4S and the targeting peptide of the invention.

FIG. 4 Binding of a peptide of the invention having the sequence RYFvRIKYRh ("RYF") to various proteoglycans (4A) as compared to the binding of the TAT peptide (4B); HS: heparan sulfate; C4S: chondroitin-4-sulfate; C6S: chondroitin-6-sulfate; HA: hyaluronic acid. The RYF peptide of the invention specifically and selectively binds C4S over other proteoglycans.

Figure 5:
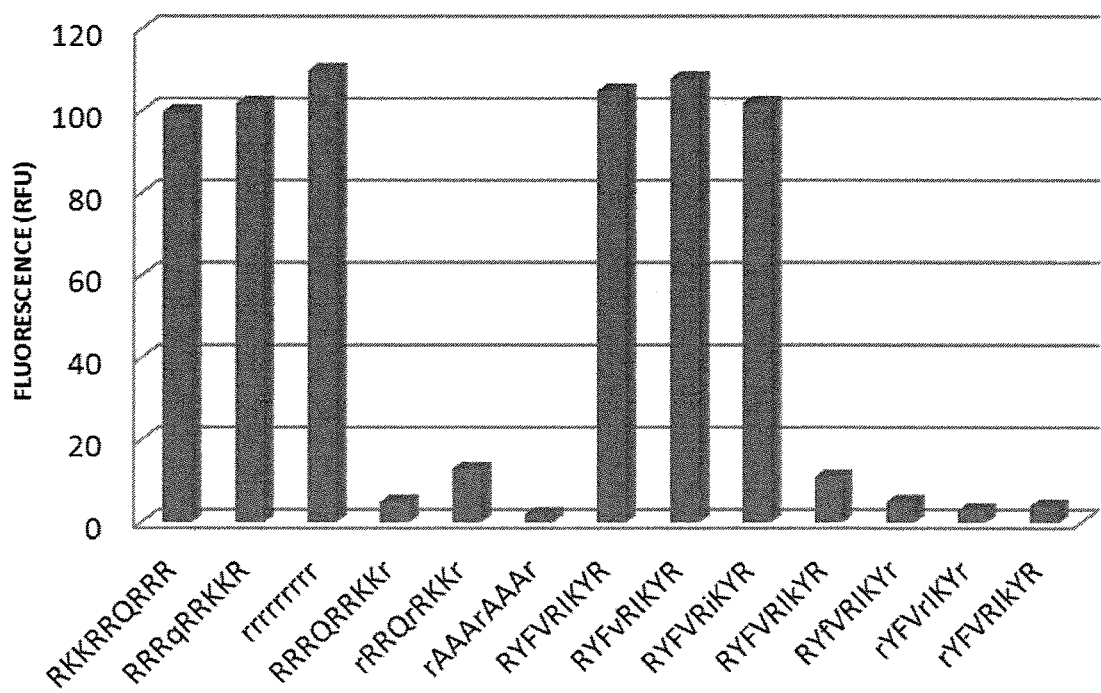

FIG. 5 Binding of peptides according to the invention to C4S. Upper case letters indicate L-enantiomers and a lower case letters indicate D-enantiomers. Binding to C4S is maintained only where all of the positions 1, 5, 9 and 3 or 7 have the same chirality.

Figure 6:
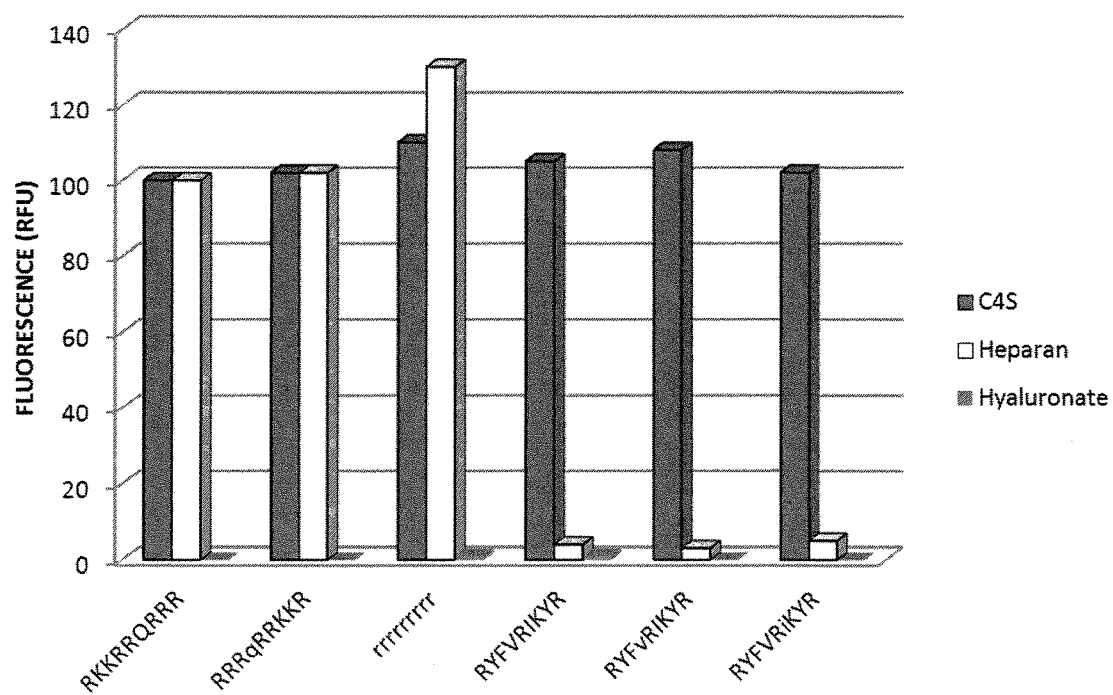

FIG. 6 Binding of peptides according to the invention to C4S. Upper case letters indicate L-enantiomers and a lower case letters indicate D-enantiomers. Selective binding to C4S over binding to the proteoglycans heparin and hyaluronate is correlated with decreased negative charge of the peptide.

Figure 7:
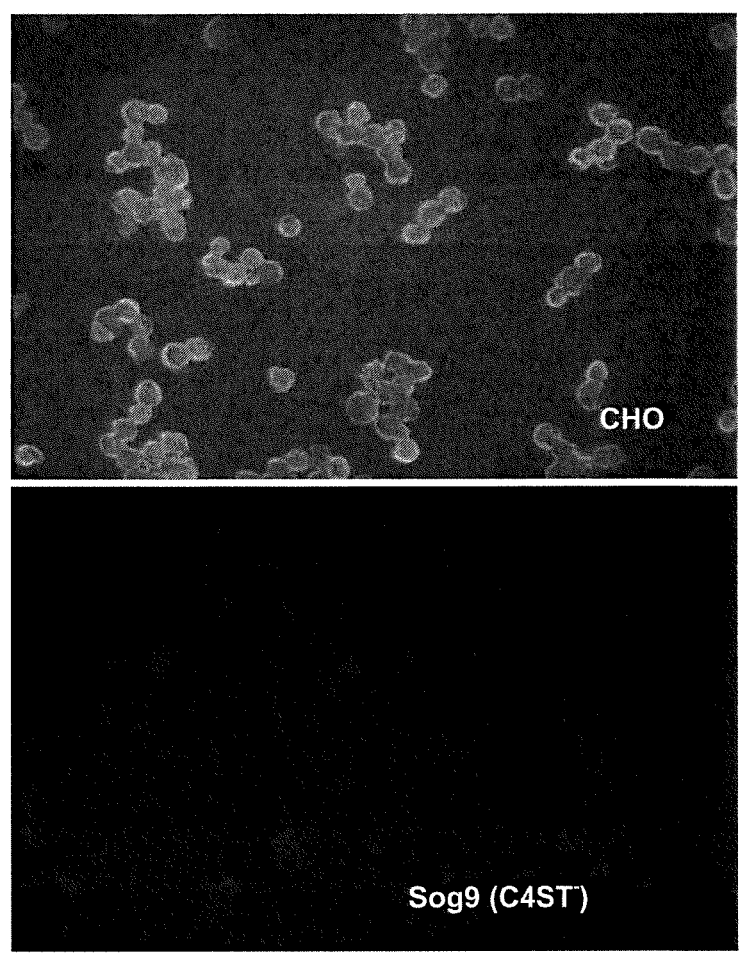

FIG. 7 LUMASCOPE™ fluorescence microscopy images of C4S expressing CHO cells and C4S deficient Sog9 cells previously incubated with a FITC-labeled peptide of the invention: RYFvRIKYRh ("RYF"; SEQ ID NO:2). RYF failed to bind the Sog9 cells, which lacked C4S expression.

Figure 8:
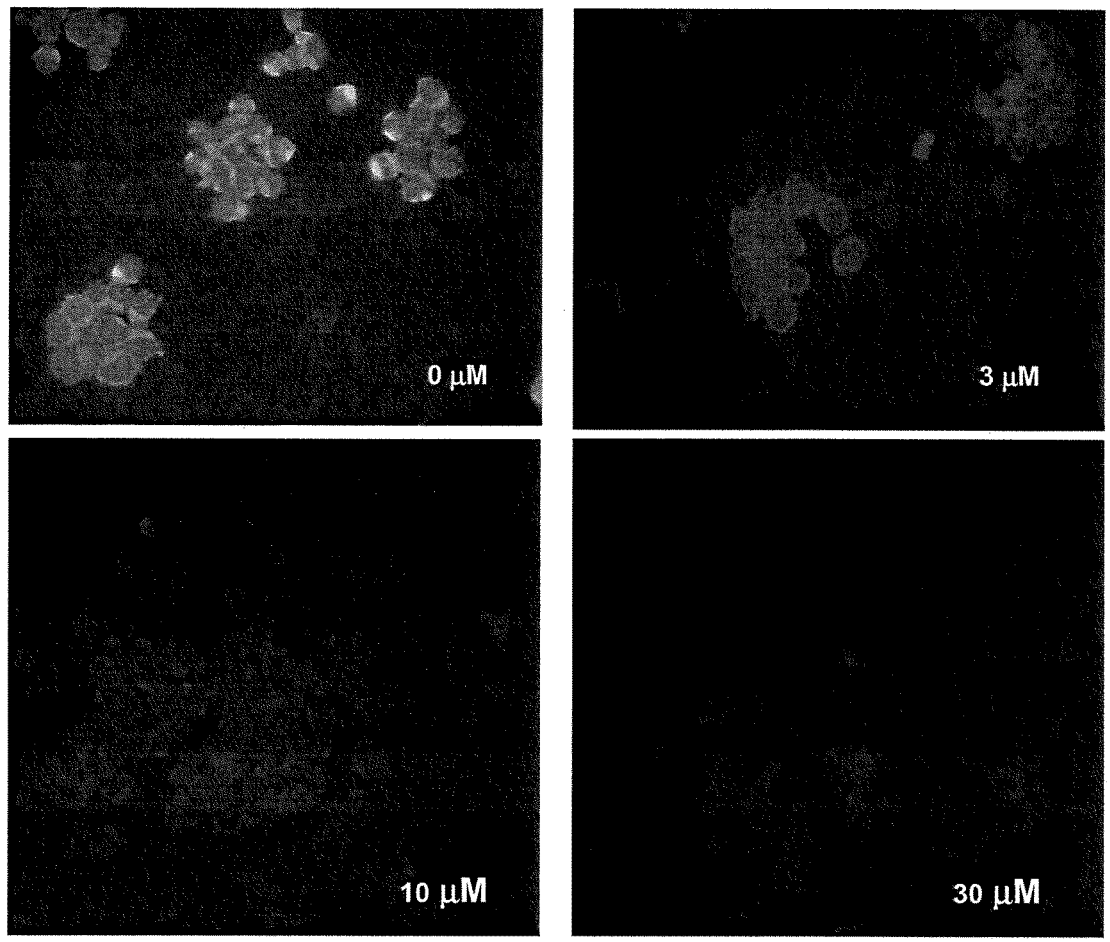

FIG. 8 LUMASCOPE™ fluorescence microscopy images of this binding of a FITC-labeled peptide of the invention: RYFvRIKYRh ("RYF"; SEQ ID NO:2) to macrophages preincubated for 16 hours with 0, 3, 10 or 30 µM chlorate, an inhibitor of sulfotransferases (and thus, C4S expression). RYF binding decreased with decreasing C4S expression.

Figure 9:
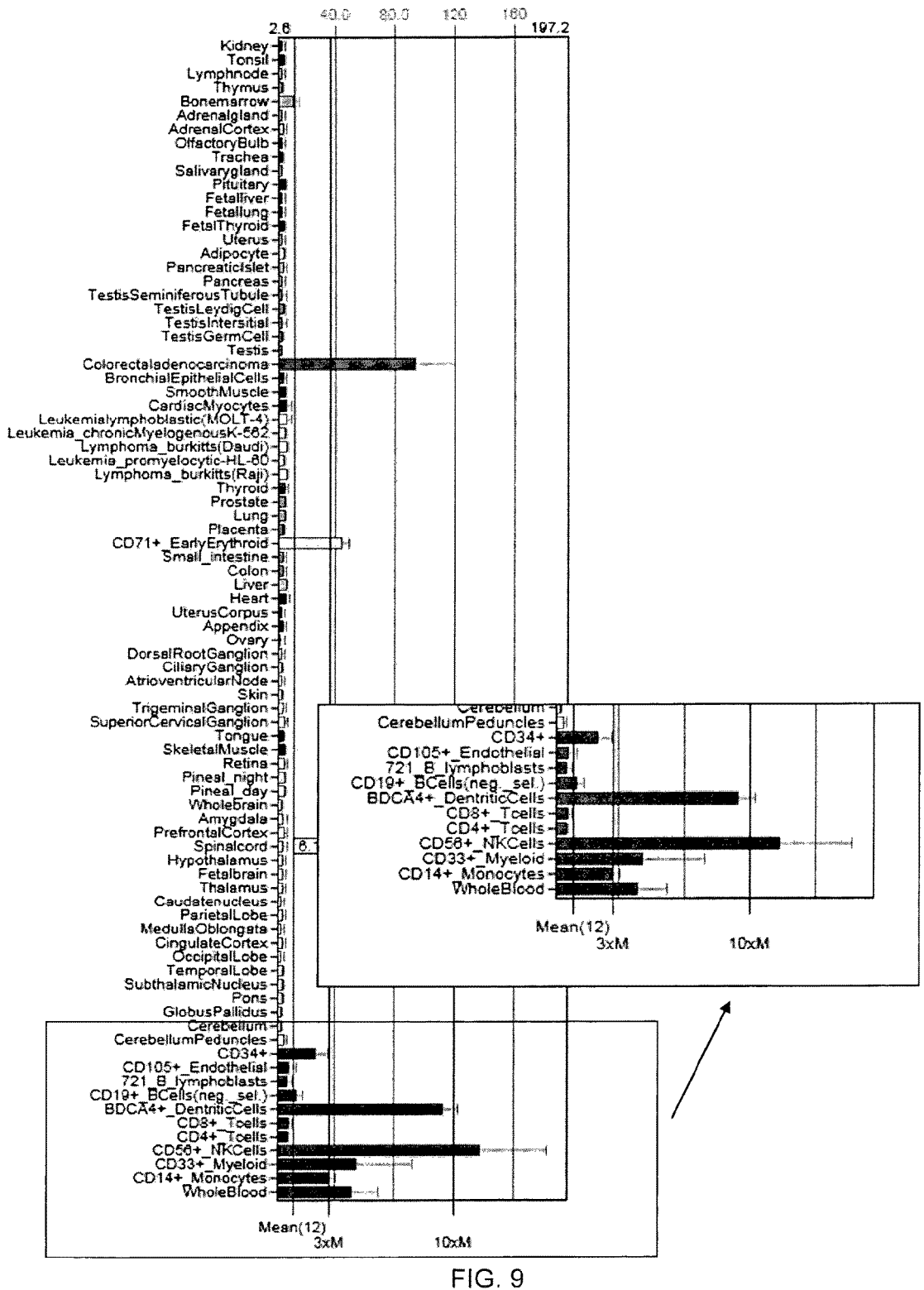

FIG. 9 CHST11 gene expression data from Atlas arrays.

Figure 10:
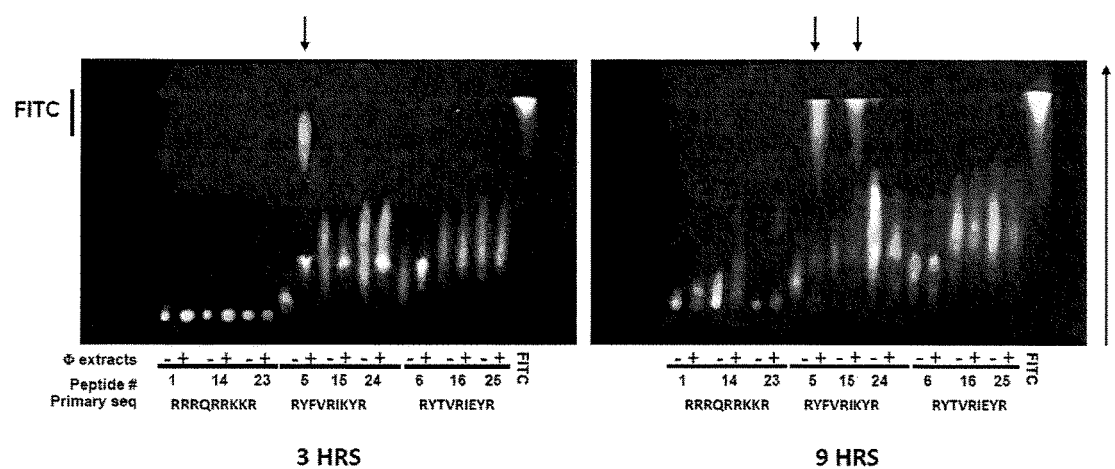

FIG. 10 Release of N-terminal conjugated FITC from peptides of the invention on exposure to macrophage extracts. Peptides 1, 5 and 6 have the consensus: RXXxRXXXRh; peptides 14, 15 and 16 have the consensus: RXxXRXXXRh; peptides 23, 24 and 25 have the consensus: rXXXrXXXr. The conjugation between the peptides and FITC was made through a regular covalent peptide bond to the N-terminal a.a. of the peptides. +/− indicates the presence or absence of cell extracts.

Figures 11A, 11B:
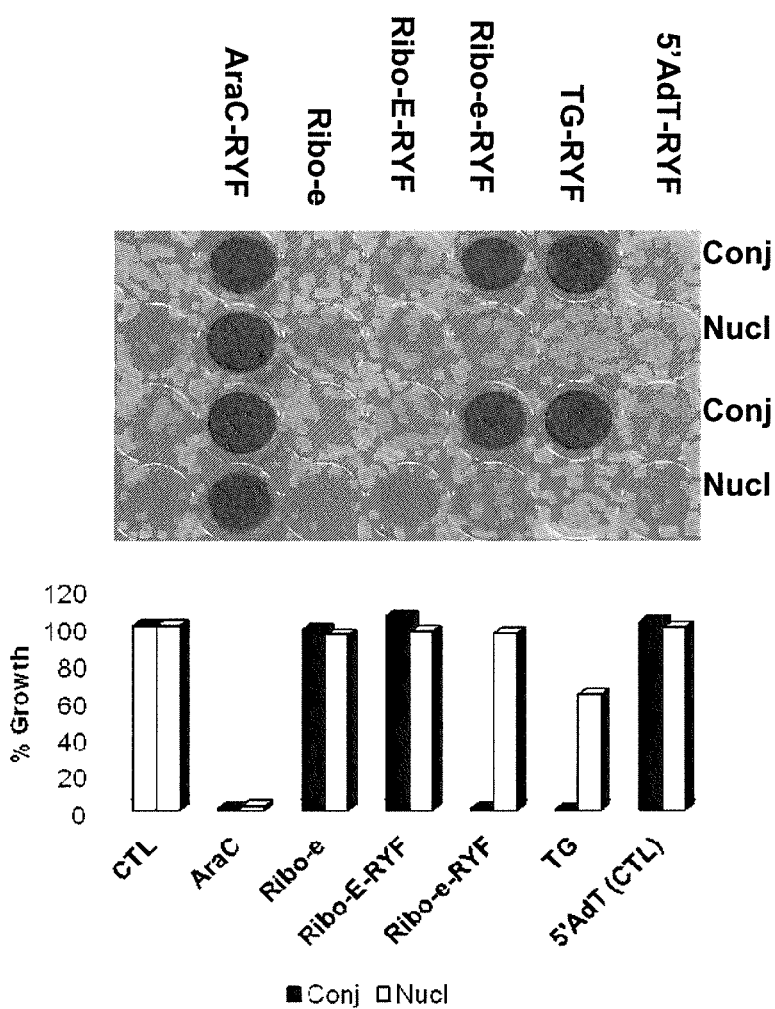

FIG. 11 Growth of raw macrophage derived cells incubated with 2.5 µM of the indicated nucleoside analog or the analog as a conjugate with the RYF (SEQ ID NO:2) peptide in the presence of phenol red. Cultures containing dividing cells turn medium clear, while the medium of cultures containing in non-dividing cells remains dark (active compounds) (FIG. 11A). Percentage growth was also determined by measuring the relative content of LDH (FIG. 11B).

Figure 12:
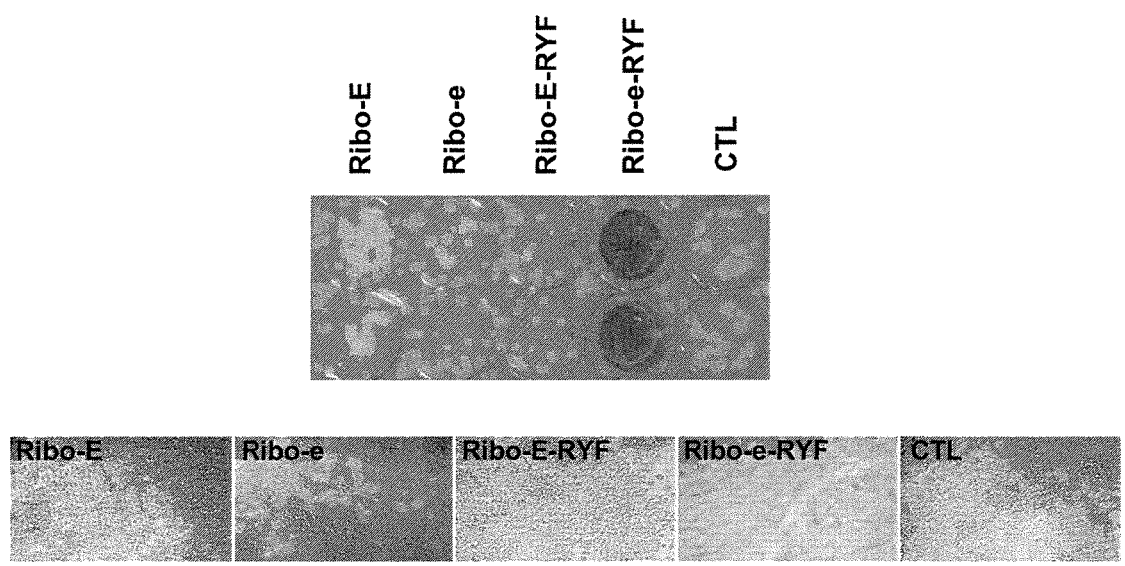

FIG. 12 Growth of raw macrophage derived cells exposed to 3' amino β-D-arabinofuranoside either alone or in the form of a conjugate with the RYF (SEQ ID NO:2) peptide in the presence of phenol red. Cultures containing dividing cells turn medium clear, while the medium of cultures containing in non-dividing cells remains dark. Only conjugation to RYF (SEQ ID NO:2) via a D-amino acid linkage demonstrated cytotoxicity.

Figure 13:
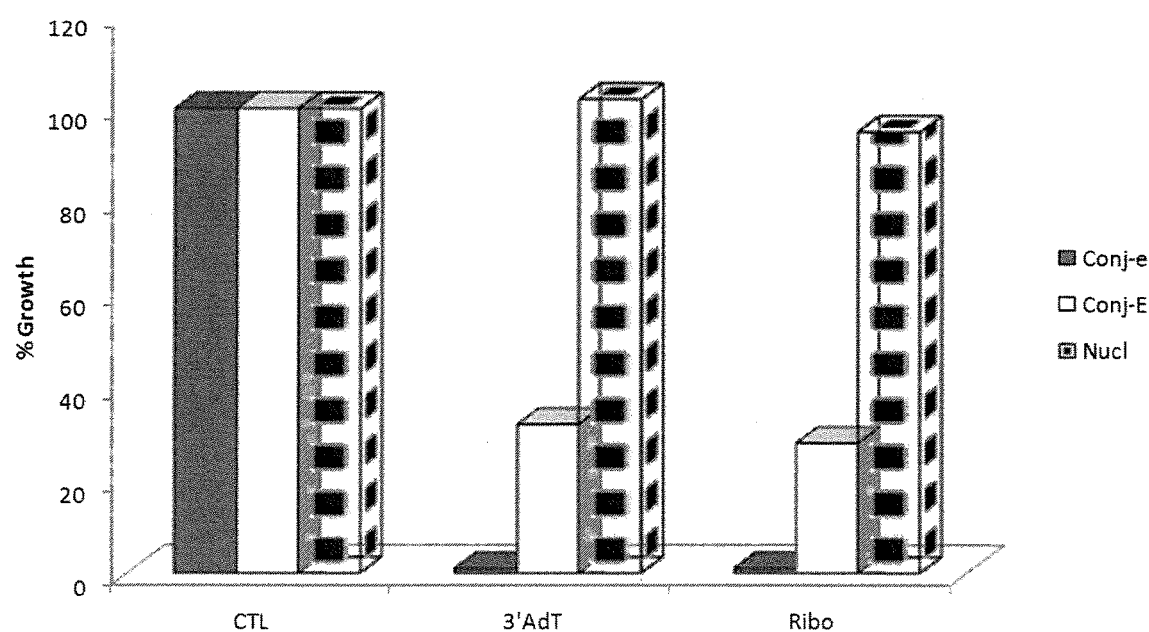

FIG. 13 Growth of raw macrophage derived cells exposed to 3'AdT (3' amino deoxythymidine) and 3' amino β-D-arabinofuranoside (Ribo) either alone or in the form of a conjugate with the RYF (SEQ ID NO:2) peptide in the presence of phenol red. Cultures containing dividing cells turn medium clear, while the medium of cultures containing in non-dividing cells remains dark. Linkage with the D-entantiomer "e" converts inactive compounds into highly cytostatic ones.

Figure 14:
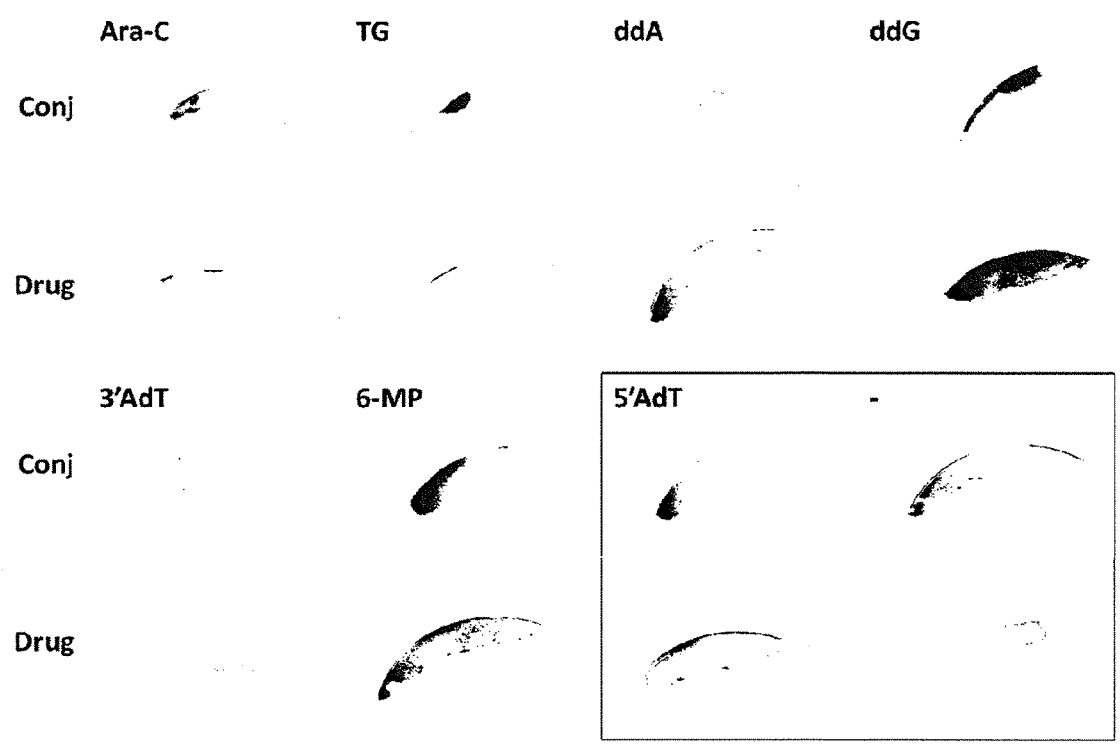

FIG. 14 Growth of MOLT4 cells exposed to the indicated compound or the compound as a conjugate with the RYF (SEQ ID NO:2) peptide (an exemplary peptide of the invention).

Figure 15:
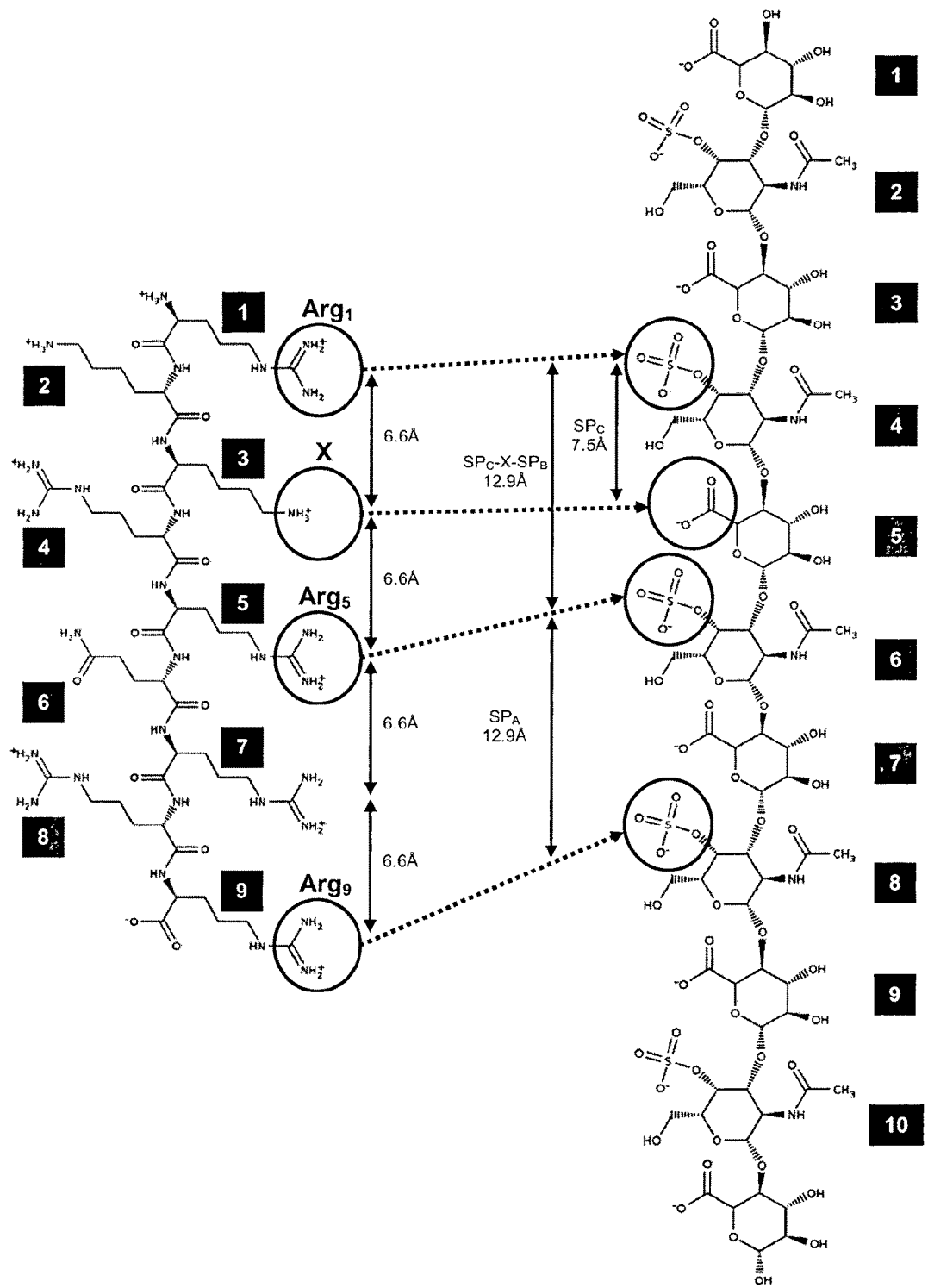

FIG. 15 Schematic detailing the average distances between potentially interacting chemical residues of TAT and C4S. The boxed numbers identify the residue numbering for each molecule used in the simulations and as described herein.

Figure 16:
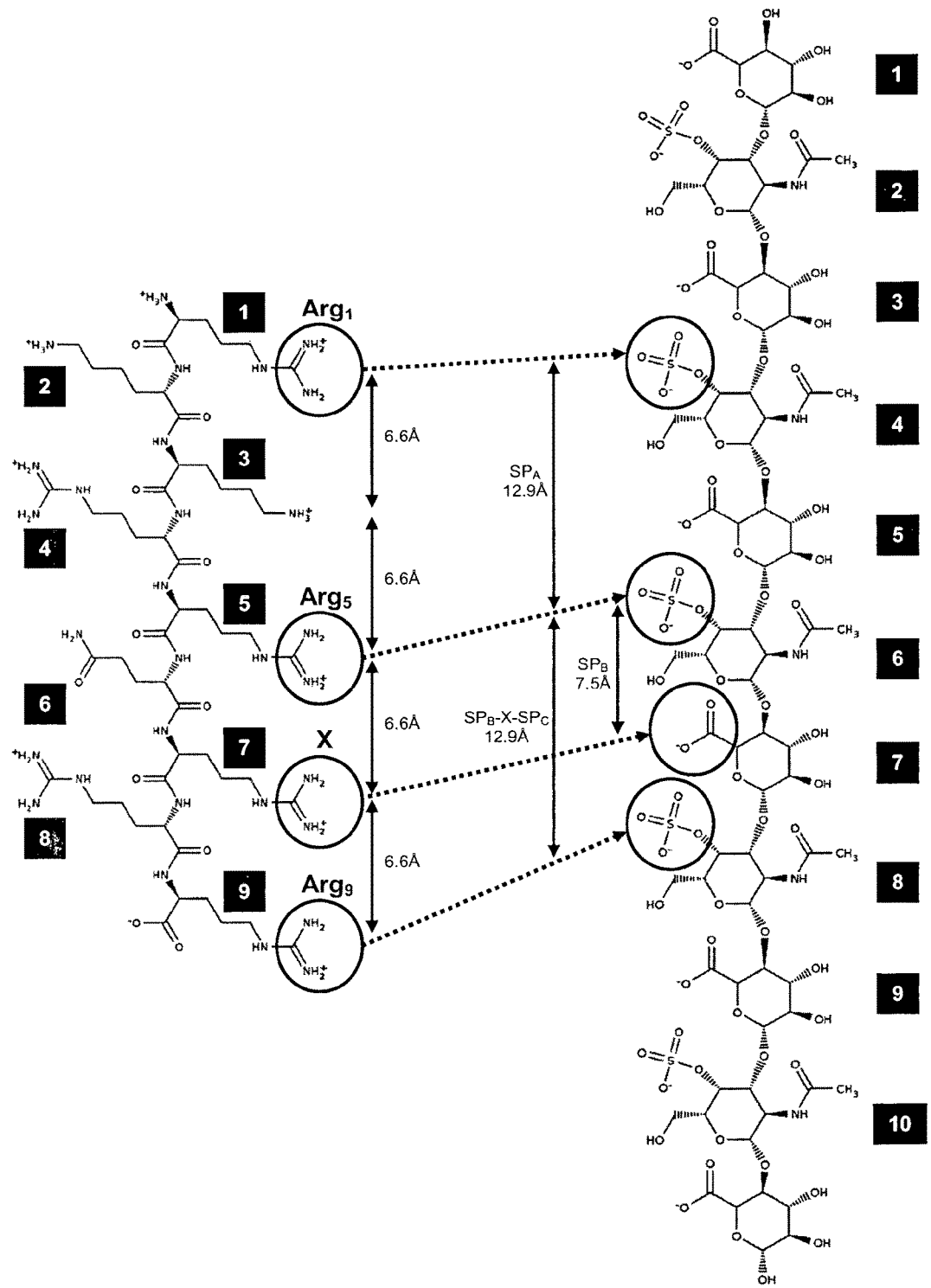

FIG. 16 Schematic detailing the average distances between potentially interacting chemical residues of TAT and C4S. The boxed numbers identify the residue numbering for each molecule used in the simulations and as described herein.

Figure 17:
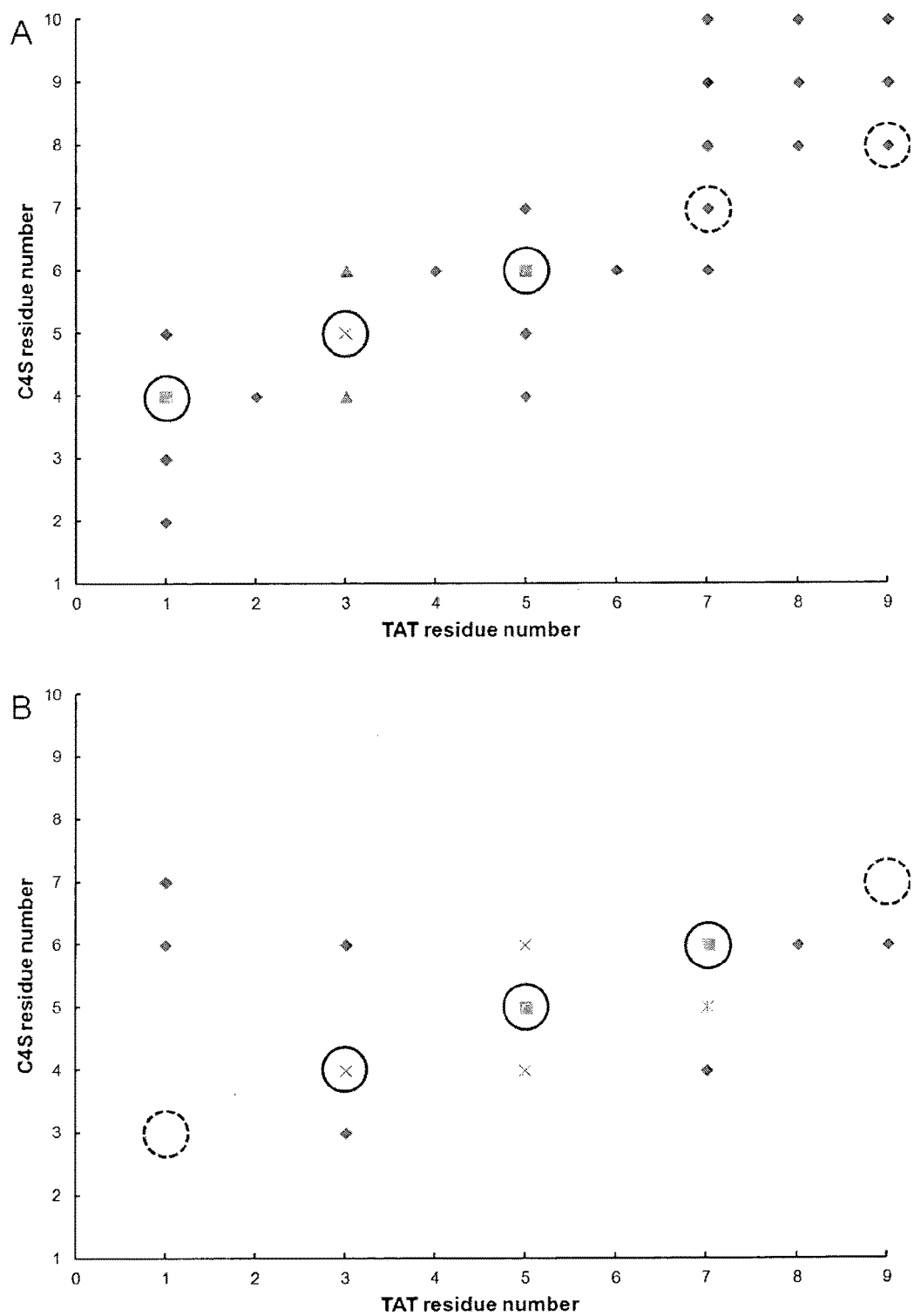

FIG. 17 Frequency of occurrence of interactions between residue pairs of TAT and C4S, calculated over 30 MD simulations, each 20 ns in length, starting from (A) the triplet of interacting residue pairs 1/4; 3/5; and 5/6 of TAT and C4S, respectively; and (B) the triplet of interacting pairs 3/4; 5/5 and 7/6 of TAT and C4S, respectively. The intervals of calculated frequencies of occurrence are 90-100% (square), 80-90% (cross), 70-80% (triangle), 50-70% (star) and 30-50% (diamond). Solid-line circles show the interacting residue pairs introduced at the start of the MD simulation, while dashed-line circles show the expected interacting residue pairs that should form spontaneously if the hypothesized interaction scheme is correct.

Figure 18A:
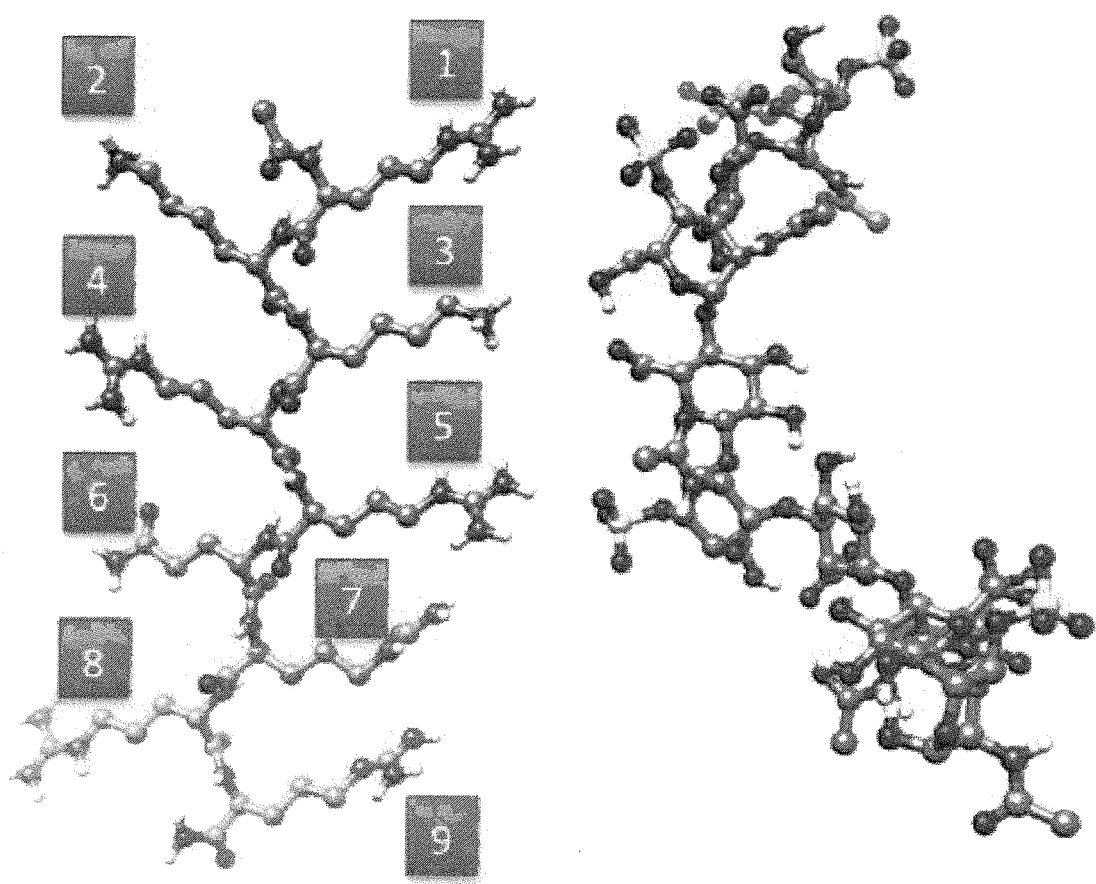
Figure 18B:
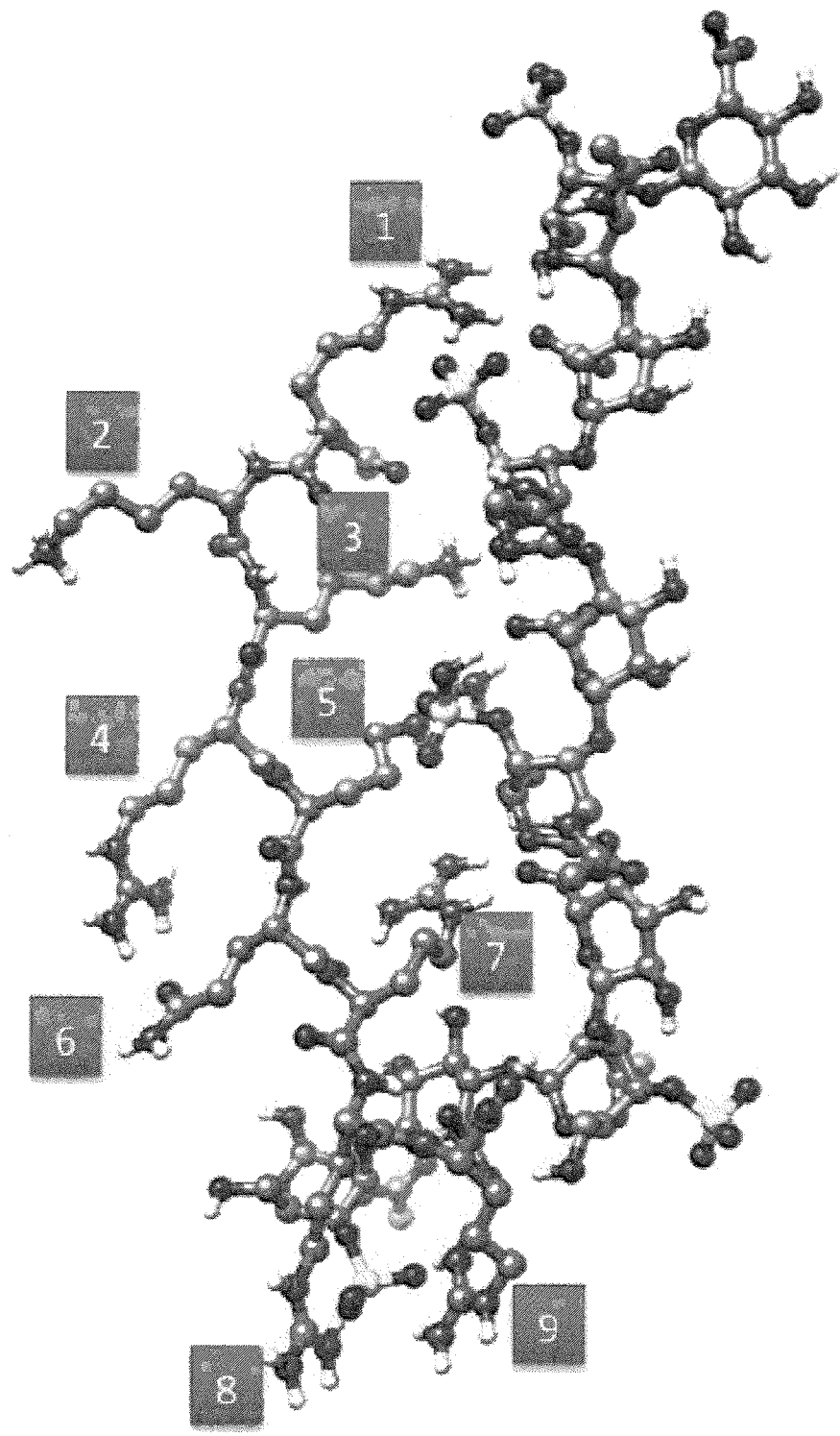

FIG. 18 (A) Starting conformation of the TAT/C4S complex used to initiate the MD simulation (the results of which are present in FIG. 17A). Only residues 1/4, 3/5 and 5/6 of TAT and C4S, respectively are interacting.

(B) One frame extracted from one of the MD simulations showing the spontaneous formation of interactions between residues 7 and 9 of TAT and highly-numbered residues of C4S, including residues 7 and 8.

6. DETAILED DESCRIPTION OF THE INVENTION

The present invention relates to molecules, peptides, polypeptides and compounds comprising or consisting of such molecules, peptides or polypeptides having specific consensus sequences or structures and their use for specific transport of biologically active moieties (BAMs) to the intercellular environment, i.e., the cytoplasm and/or the nucleus. The inventors have surprisingly discovered that certain consensus structures or sequences of molecules and peptides are able to selectively target specific proteoglycans, in particular chondroitin-4-sulfate (C4S). Accordingly, the molecules, proteins, polypeptides and compounds comprising or consisting of such molecules, peptide or polypeptide comprising or consisting of one or more of the consensus sequences disclosed herein may find particular use as transport moieties for the targeted delivery of BAMs to cells expressing C4S.

Although the binding of certain peptides to proteoglycans and phospholipids is known, it has previously been viewed as a non-specific process driven primarily though ubiquitous hydrostatic interactions. As such, it has not been previously suggested that such interactions could be manipulated to impart selectivity, preventing the peptides from being used for specific targeting. Despite the perceived ubiquitous nature of these interactions, the present inventors have surprisingly discovered that specific peptide sequences can be designed that exhibit selectivity for certain proteoglycans over phospholipids in general. Specifically, the present inventors have discovered that a peptide comprising a 9 residue sequence having arginines at positions 1, 5, and 9, and a lysine or arginine at position 3 or 7, or a molecular construct exhibiting an equivalent relative 3D confirmation of these 4 residues (e.g., a residue-spacer construct), optimally interacts via electrostatic bridging with the sulfates on the aminoglycan units of C4S. Moreover, including non-charged amino acids or non-positively charged chemical spacers in the remaining positions provides selectivity, inhibiting or substantially reducing the non-specific interaction of the peptide with other proteoglycans and/or phospholipids. Thus, the unique combination of residues and/or 3D presentation of specific residues allows peptides and residue-spacer constructs to be designed that exhibit selective binding for C4S proteoglycans, over other proteoglycans and other phospholipids.

C4S is known to be only partially sulfated, that is, the molecule is not sulfated at all potential sites for sulfation. Computer simulations of molecular interactions revealed that arginines at, at least positions 1, 5 and 9 of a 9-mer peptide (and/or at the equivalent 3D positions of a 9-mer peptide, e.g., in a residue spacer construct) specifically interacted with the sulfate pattern specific to C4S. An additional charged amino acid, in particular, an arginine or a lysine, at position 3 or 7 (and/or at its equivalent 3D position), but not both, was also found necessary for specific binding. The model simulations suggest that position 3 or position 7 are equivalent three dimensionally within the 9-mer, in particular, within the spatial orientation of the other relevant residues for interaction, i.e., at positions 1, 5 and 9.

The remaining residues are not predicted by the model to be involved in the binding of the peptide to C4S, and, provided the three dimensional linear conformation of residues 1, 5, 9 and (3 or 7) was not disturbed in the peptide, substitution with a wide variety of amino acids (including non-natural amino acids, such as D-amino acids) at the freely selectable positions 2, 4, 6, 8 and (3 (where 7 is selected as lysine or arginine) or 7 (where 3 is selected as lysine or arginine)) had little to no effect on the specific binding to C4S. Accordingly, the inventors surprisingly discovered that the provided the 3D presentation and/or orientation of these 3 arginine residues and one lysine or arginine residue is maintained in the molecule, C4S specific binding will be maintained. Therefore, the invention encompasses the replacement of the residues at these freely-selectable positions with chemical spacers provided that the relative 3D orientation of the arginines at positions 1, 5 and 9 and the arginine or lysine at position 3 or 7 is maintained as in consensus sequences (i) (ii). However, the use of the charged amino acids arginine or lysine in these freely selectable positions (where amino acid residues are present) and/or charged linking groups, in particular positively charged groups increased the likelihood of non-specific interactions with other proteoglycans and phospholipids. Therefore, to maintain specificity, the use of arginine and lysine in the freely selectable positions is avoided in the peptides of the invention and/or the use of charged linking groups where one or more of the freely selectable residues is replaced by a chemical linker in the residue-linker constructs of the invention is avoided.

Additionally, it was discovered that specificity can be maintained using D-amino acids in the molecules of the invention (e.g., peptides or residue-spacer constructs) at the positions relevant for C4S binding, i.e., Arg1, Arg5, Arg9 and (Arg/Lys3 or Arg/Lys7), provided that all positions have the same chirality. It is believed that the use of a single chirality at these positions presents the same three-dimensional structure of the amino acid side chains. Where one or more of these positions has a differing chirality, the three-dimensional liner arrangement is distorted. Thus, the invention encompasses a molecule comprising 3 arginine residues and one arginine or lysine residue, wherein each of the 4 residues is a L-residue or wherein each of the 4 residues is a D-residue, provided that the molecule presents the residues in the same or similar 3D orientation and configuration as Arg1, Arg5, Arg9 and Arg/Lys3 or Arg/Lys7 in consensus sequences (i) and (ii) (in particular, when the molecules are in solution).

The consensus sequences of the molecules of the invention are preferably envisioned as transporter moieties, of use in the intercellular transport of associated cargo molecules/moieties. The cellular surface molecules containing proteoglycans, e.g., CD68, are known to be cycled via endosomes. To favor release of the compound of the invention from the endosome (and help further avoid degradation), one to several amino acid residues capable of acting as a proton sponge can optionally be added to the N- or C-terminus of the transporter moiety. The proton sponge increases the osmolarity of the endosome, causing swelling and rupture, leading to cytosolic release of its contents rather than their degradation. Any amino acid residue or combination of residues known in the art or described herein capable of functioning as a proton sponge can be used in the accordance with the invention. The final amino acid of this optional series of proton sponge resides (i.e., the final N-terminal or C-terminal residue of the proton sponge residues (where present)) may also optionally be a D-entantiomer to avoid degradation/cleavage of the proton sponge residues. Accordingly, the invention encompasses the optional use of one or more amino acid residues added to the N- or C-terminus of the transporter moiety, wherein the N- or C-terminal residue, respectively, is optionally a D-entantiomer. In preferred embodiments, the one or more residues of the proton sponge residues is (are) not lysine or arginine residues. The optional residues of the proton sponge as defined herein are represented in the consensus sequences (i) to (xiv) of the invention by $LD_{10}$ or $LD_{-1}$. The optional N- or C-terminal residue of the proton sponge is represented in the consensus sequences (i) to (xiv) of the invention by $XD_{11}$ or $XD_{-2}$ Thus, in preferred embodiments, $LD_{10}$ or $LD_{-1}$ of consensus sequences (i) to (xiv) (where present) represents any L- or D-amino acid other than L- or D-arginine or L- or D-lysine; in connection with these preferred embodiments or as independent embodiments, $XD_{11}$ or $XD_{-2}$ of consensus sequences (i) to (xiv) (where present) is preferentially any D-amino acid other than D-arginine or D-lysine. In the most preferred embodiments, the one or more residues of the proton sponge residues is (are) histidine residues. Thus, in the most preferred embodiments, $LD_{10}$ or $LD_{-1}$ of consensus sequences (i) to (xiv) represents L- or D-histidine; in connection with these most preferred embodiments or as independent embodiments, $XD_{11}$ or $XD_{-2}$ of consensus sequences (i) to (xiv) is most preferentially D-histidine.

6.1 Molecule Consensus Structures

The above discoveries of the inventors may be presented as a consensus structure. The invention is generally directed to at least one isolated molecule, or compounds comprising or consisting of said molecule, wherein the molecule has a consensus structure according to any one of (iii) to (vi), or the reverses thereof:

$Arg_1$-$(SP_A)$-$Arg_5$-$(SP_B)$-X-$(SP_C)$-$Arg_9$-$(LD_{10})_n$-$(XD_{11})_m$;  (iii)

$Arg_1$-$(SP_C)$-X-$(SP_B)$-$Arg_5$-$(SP_A)$-$Arg_9$-$(LD_{10})_n$-$(XD_{11})_m$;  (iv)

$(XD_{-2})_m$-$(LD_{-1})_n$-$Arg_1$-$(SP_A)$-$Arg_5$-$(SP_B)$-X-$(SP_C)$-$Arg_9$; or  (v)

$(XD_{-2})_m$-$(LD_{-1})_n$-$Arg_1$-$(SP_C)$-X-$(SP_B)$-$Arg_5$-$(SP_A)$-$Arg_9$  (vi)

wherein, $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1;

wherein (a) $Arg_1$, $Arg_5$, and $Arg_9$ represent L-arginine; and X represents L-lysine or L-arginine, or (b) $Arg_1$, $Arg_5$, and $Arg_9$ represent D-arginine; and X represents D-lysine or D-arginine;

wherein $(SP_A)$ represents a chemical linker that (a) consist of a peptide chain of 3 amino acid resides, wherein each residue may be independently selected from any amino acid residue other than D-arginine, D-lysine, L-arginine or L-lysine; or (b) separates the adjacent amino acid residues by 12.9±1.5 Å;

wherein $(SP_C)$ represents a chemical linker that (a) consists of a single amino acid residue that may be any amino acid residue other than D-arginine, D-lysine, L-arginine or L-lysine; or (b) separates the adjacent amino acid residues by 7.5±1.5 Å when the molecule is in extended conformation;

and wherein $(SP_B)$-X-$(SP_C)$ or its reverse, $(SP_C)$-X-$(SP_B)$ represents a chemical linker (a) wherein $SP_B$ and $SP_C$ each represent a single amino acid residue that may be independently selected from any amino acid residue other than D-arginine, D-lysine, L-arginine or L-lysine; or (b) that separates the adjacent amino acid residues $Arg_1$ and $Arg_5$ or $Arg_5$ and $Arg_9$ by 12.9±1.5 Å when the construct is in extended conformation.

When the molecule or compound of the invention comprises one or more chemical spacers/linkers that is not exclusively comprised of amino acid residues, care must be taken such that the side chains of Arg1, Arg5, Arg9 and Arg/Lys3 or Arg/Lys7 retain the same or similar 3D presentation as their counterpart side chains in the peptide and/or polypeptide consensus sequences (i) and/or (ii). Thus, the side chains of Arg1, Arg5, Arg9 and Arg/Lys3 or Arg/Lys7 within residue-spacer constructs according to the methods of the invention should present in a linear or near linear arrangement within 3D space when the molecule and/or construct is in extended conformation.

6.2 Peptide Consensus Sequences

In embodiments of the invention wherein the molecules and/or compounds according to any of consensus structures (iii) to (vi) comprise or consist only of amino acid residues, the consensus structures may be represented by consensus sequences of a peptide or polypeptide. Accordingly, in certain embodiments, the present invention is directed to compounds comprising or consisting of at least one isolated peptide or polypeptide having an amino acid sequence according to the following consensus sequence (i) or (ii), or the reverses thereof:

$Arg_1$-$X_2$-$X_3$-$X_4$-$Arg_5$-$X_6$-$X_7$-$X_8$-$Arg_9$-$(LD_{10})_n$-$(XD_{11})_m$, or  (i)

$(XD_{-2})_m$-$(LD_{-1})_n$-$Arg_1$-$X_2$-$X_3$-$X_4$-$Arg_5$-$X_6$-$X_7$-$X_8$-$Arg_9$  (ii)

wherein, (a) $Arg_1$, $Arg_5$, and $Arg_9$ represent L-arginine; $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1; and wherein the remaining amino acids $X_2$ to $X_4$ and $X_6$ to $X_8$ may be any L- or D-amino acid other than L-lysine, D-lysine, L-arginine or D-arginine, with the proviso that either $X_3$ or $X_7$, but not both, represents L-lysine or L-arginine;

or wherein, (b) $Arg_1$, $Arg_5$, and $Arg_9$ represent D-arginine; $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1; and wherein the remaining amino acids $X_2$ to $X_4$ and $X_6$ to $X_8$ may be any L- or D-amino acid other than L-lysine, D-lysine, L-arginine or D-arginine, with the proviso that either $X_3$ or $X_7$, but not both, represents D-lysine or D-arginine.

Consensus sequence (i), above, with conditions (a) is SEQ ID NO:17, and with conditions (b) is SEQ ID NO:19. Consensus sequence (ii), above, with conditions (a) is SEQ ID NO:18, and with conditions (b) is SEQ ID NO:20.

6.3 Residue-Spacer Consensus Structures

In embodiments of the invention wherein the chemical linkers/spacers represented by $SP_A$, $SP_B$, and $SP_C$ in any of consensus structures (iii) to (vi) do not comprise amino acid residues, the consensus structures may be represented by consensus structures for a residue-spacer construct. In such embodiments, the invention can be defined as direct to at least one residue-spacer construct, or compounds comprising or consisting of them, wherein the construct has a consensus structure according to any one of (vii) to (x), or the reverses thereof:

$Arg_1$-$(CL_A)$-$Arg_5$-$(CL_B)$-X-$(CL_C)$-$Arg_9$-$(LD_{10})_n$-$(XD_{11})_m$;  (vii)

$Arg_1$-$(CL_C)$-X-$(CL_B)$-$Arg_5$-$(CL_A)$-$Arg_9$-$(LD_{10})_n$-$(XD_{11})_m$;  (viii)

$(XD_{-2})_m$-$(LD_{-1})_n$-$Arg_1$-$(CL_A)$$Arg_5$-$(CL_B)$-X-$(CL_C)$-$Arg_9$; or  (ix)

$(XD_{-2})_m$-$(LD_{-1})_n$-$Arg_1$-$(CL_C)$-X-$(CL_B)$-$Arg_5$-$(CL_A)$-$Arg_9$  (x)

wherein, $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1;

wherein (a) $Arg_1$, $Arg_5$, and $Arg_9$ represent L-arginine; and X represents L-lysine or L-arginine, or (b) $Arg_1$, $Arg_5$, and $Arg_9$ represent D-arginine; and X represents D-lysine or D-arginine;

wherein $(SP_A)$ represents a chemical linker that separates the adjacent amino acid residues by 12.9±1.5 Å;

wherein $(SP_C)$ represents a chemical linker that separates the adjacent amino acid residues by 7.5±1.5 Å when the molecule is in extended conformation;

and wherein $(SP_B)$-X-$(SP_C)$ or its reverse, $(SP_C)$-X-$(SP_B)$ represents a chemical linker that separates the adjacent amino acid residues $Arg_1$ and $Arg_5$ or $Arg_5$ and $Arg_9$ by 12.9±1.5 Å when the construct is in extended conformation.

When the molecule or compound of the invention comprises one or more chemical spacers/linkers that is not exclusively comprised of amino acid residues, care must be taken such that the side chains of Arg1, Arg5, Arg9 and Arg/Lys3 or Arg/Lys7 retain the same or similar 3D presentation as their counterpart side chains in the peptide and/or polypeptide consensus sequences (i) and/or (ii). Thus, the side chains of Arg1, Arg5, Ang9 and Arg/Lys3 or Arg/Lys7 within residue-spacer constructs according to the methods of the invention should present in a linear or near linear arrangement within 3D space when the molecule and/or construct is in extended conformation.

6.4 Targeting Moieties

The molecules and compounds described above according to consensus sequences (iii) to (vi) find particular use as transport and/or targeting moieties, specifically recognizing and/or binding proteoglycans, e.g., as expressed on the surface of a cell, in particular, binding the proteoglycan C4S selectively over other proteoglycans. The portion of the above consensus sequences (iii) to (vi) acting as the targeting moiety that specifically interact with the C4S proteoglycan is represented by $Arg_1$-($SP_A$)-$Arg_5$-($SP_B$)-X-($SP_C$)-$Arg_9$ or $Arg_1$-($SP_C$)-X-($SP_B$)-$Arg_5$-($SP_A$)-$Arg_9$ (including the specific embodiments having targeting moiety consensus sequences or structures $Arg_1$-$X_2$-$X_3$-$X_4$-$Arg_5$-$X_6$-$X_7$-$X_8$-$Arg_9$ (SEQ ID NO:21, where a fragment of SEQ ID NO:17 or SEQ ID NO:18; SEQ ID NO:22, where a fragment of SEQ ID NO:19 or SEQ ID NO:20), $Arg_1$-($CL_A$)-$Arg_5$-($CL_B$)-X-($CL_C$)-$Arg_9$ and $Arg_1$-($CL_C$)-X-($CL_B$)-$Arg_5$-($CL_A$)-$Arg_9$)) are identical molecules with respect to the 3D presentation of the amino acid residues corresponding to Arg1, Arg5, Arg9, and Arg/Lys3 or Arg/Lys7 and, in particular, the sides chains of these residues. Accordingly, any molecule comprising 3 arginine residues and one lysine residue according to consensus sequences (iii) to (vi) can be developed as the targeting moiety according to the following rules:

(1) Each of the residues Arg1, Arg5, and Arg9 must be the same optical isomer of arginine, i.e., each must be an L-arginine or each must be a D-arginine.

(2) Arg1 must be linked to Arg5 using one or more chemical spacers (which may consist exclusively of one or more amino acid residues or may comprise both amino acid residues and chemical spacers/linkers) such that they are separated by 12.9±1.5 Å when the molecule is in extended conformation; Arg5 must be further linked to Arg9 using one or more chemical spacers (which may consist exclusively of one or more amino acid residues or may comprise both amino acid residues and chemical spacers/linkers) such that they are also separated by 12.9±1.5 Å when the molecule is in extended conformation.

(3) The targeting moiety must also comprise one lysine or arginine residue in the linkage between Arg1 and Arg5 or between Arg5 and Arg9 (but not both) that is the same chirality as the Arg1, Arg5 and Arg9 (this residue corresponds to the residue as position 3 or 7 (but not both simultaneously) in consensus sequences (i) and (ii) and to the residue "X" in consensus sequences (iii) to (x)). In other words, where Arg1, Arg5 and Arg9 are L-arginine, the lysine/arginine must be a L-lysine or a L-arginine; and where Arg1, Arg5 and Arg9 are D-arginine, the lysine/arginine must be a D-arginine or a D-lysine.

(4). Where the lysine/arginine is positioned in the linkage between Arg1 and Arg5, it is separated from Arg1 by 7.5±1.5 Å; where the lysine/arginine is positioned in the linkage between Arg5 and Arg9, it is separated from Arg9 by 7.5±1.5 Å.

(5) The remaining linkages may comprise any chemical spacer or linker known in the art and/or described herein (which may consist exclusively of one or more amino acid residues or may comprise both amino acid residues and chemical spacers/linkers) suitable for maintaining the required separation of Arg1, Arg5, Arg9 and X as well as suitable to maintain a 3D orientation and/or 3/D presentation of amino acids and their side chains similar or the same as that in the corresponding residues in consensus sequences (i) and (ii). The linkages between Arg1, Arg5, Arg9 and X should not be positively charged. Where the linkages between Arg1, Arg5, Arg9 and X are amino acid residues or comprise amino acid residues, the residues can be any D- or L-amino acid other than D- or L-arginine or D- or L-lysine.

Where the consensus structures of the invention consist or comprise exclusively amino acids, the targeting moiety as described immediately above can be designed as follows. The sequence of the targeting moiety in consensus structures (iii) to (vi), where the structure consists or comprises exclusively amino acid residues is represented by $Arg_1$-$X_2$-$X_3$-$X_4$-$Arg_5$-$X_6$-$X_7$-$X_8$-$Arg_9$ (see, e.g., consensus sequences (i) and (ii)). The structure satisfies rule (2) above. That is, the linkage that separates Arg1 and Arg5 and that separates Arg5 and Arg9 by 12.9±1.5 Å when the molecule is in extended conformation that separates is a peptide consisting of 3 amino acid residues. The rules described immediately above as further applied to the peptide consensus sequence are:

(P1) Each of the residues Arg1, Arg5, and Arg9 must be the same optical isomer of arginine, i.e., each must be an L-arginine or each must be a D-arginine (corresponding to Rule (1), above).

(P2) Residue $X_3$ or $X_7$ (but not both) is a lysine or arginine of the same chirality as Arg1, Arg5 and Arg9. That is, where Arg1, Arg5 and Arg9 are L-arginine, $X_3$ or $X_7$ (but not both) must be a L-lysine or a L-arginine; and where Arg1, Arg5 and Arg9 are D-arginine, $X_3$ or $X_7$ (but not both) must be a must be a D-arginine or a D-lysine (corresponding to Rule 3 and 4, above).

(P3) The remaining residues, i.e., $X_2$, $X_4$, $X_6$, $X_8$ and $X_3$ (where $X_7$ is selected according to rule P2 immediately above) or $X_7$ (where $X_3$ is selected according to rule P2 immediately above) may be any amino acid other than L- or D-arginine or L- or D-lysine.

6.5 Chemical Linkers $SP_A$, $SP_B$, and $SP_C$ in consensus sequences (iii) to (xiv) represent chemical linkers/spacers that form part of the backbone of the molecule of the invention and may comprise or consist of exclusively one or more amino acid residues; may comprise or consist of one or more chemical linkers (i.e., that are not amino acid residues); or may comprise both amino acid residues and chemical linkers. Chemical linkers that are not amino acid residues that are of use according to the methods of the invention may be any appropriate chemical linker or chemical spacer suitable to maintain the spacing and the relative 3D orientation/presentation of the 3 arginine residues (i.e., $Arg_1$, $Arg_5$, and $Arg_9$) and the one arginine or lysine (i.e., $Arg/Lys_3$ or $Arg/Lys_7$ but not both) equivalent to the corresponding residues in consensus sequences (i) and (ii). Any such chemical linker/spacer known in the art or described herein may be used in the construction of the molecules of the invention, and it is within the abilities of one of skill in the art to select and adapt such linkers to the methods of the invention. Nonlimiting examples of appropriate chemical linkers/spacers include beta- and gamma-peptides such as those disclosed and described in e.g. Seebach et al., *Chem. Biodivers.* 1(2004), 1111-1239; sugar amino acid based scaffolds such as those disclosed and described in e.g., Chakraborty et al., Comb. Chem. High Throughput Screen. 5(2002), 373-387; beta-hairpin peptidomimetics such as those disclosed and described in e.g., Robinson, Acc. Chem. Res. 41(2008), 1278-1288; alpha-helical mimetics, beta-sheet/beta-stand mimetics and beta-turn mimetics such as those disclosed and described in e.g., Hershberger et al., Curr. Top. Med. Chem. 7(2007), 928-924 and cyclotides such as those disclosed and described in e.g., Jagadish and Camarero, Biopolymers 94(2010), 611-616. In preferred embodiments, the chemical linker/spacers are not positively charged.

6.6 BAM Conjugates

As detailed herein, the molecules and compounds of the invention comprising or consisting of the molecules, peptides and/or polypeptides according to consensus sequences and structures (i) to (x) are envisioned in preferred embodiments to function as transporter moieties capable of specifically transporting associated cargo molecules/moieties. In preferred embodiments, the molecules and compounds of the invention comprise or consist of the sequences and/or structures according to any of consensus sequences (i) to (x) further conjugated to a biologically active moiety (BAM); the structure is referenced as a BAM-conjugate throughout this description. The BAM is any moiety known or expected to exhibit a therapeutic effect when administered to an organism, or when introduced to a cell, either in vitro or in vivo. In preferred embodiments, the compounds of the invention comprise or consist of a BAM-conjugate, having a BAM conjugated at the terminus of a consensus sequence or structure (i) to (x) as described herein. Therefore, in these preferred embodiments, the BAM-conjugate has a consensus structure according to the following consensus structures (xi) to (xiv), or the reverses thereof:

$$(BAM)\text{-}(LINK)\text{-}Arg_1\text{-}(SP_A)\text{-}Arg_5\text{-}(SP_B)\text{-}X\text{-}(SP_C)\text{-}Arg_9\text{-}(LD_{10})_n(XD_{11})_m; \quad (xi)$$

$$(BAM)\text{-}(LINK)\text{-}Arg_1\text{-}(SP_C)\text{-}X\text{-}(SP_B)\text{-}Arg_5\text{-}(SP_A)\text{-}Arg_9\text{-}(LD_{10})_n\text{-}(XD_{11})_m; \quad (xii)$$

$$(XD_{-2})_m\text{-}(LD_{-1})_n\text{-}Arg_1\text{-}(SP_A)Arg_5\text{-}(SP_B)\text{-}X\text{-}(SP_C)\text{-}Arg_9\text{-}(LINK)\text{-}(BAM); \text{ or} \quad (xiii)$$

$$(XD_{-2})_m\text{-}(LD_{-1})_n\text{-}Arg_1\text{-}(SP_C)\text{-}X\text{-}(SP_B)\text{-}Arg_5\text{-}(SP_A)\text{-}Arg_9\text{-}(LINK)\text{-}(BAM) \quad (xiv)$$

wherein (BAM) represents a biologically active moiety; wherein (LINK) represents an optional linker group; wherein, $LD_{10}$ or $LD_{-1}$ represents any L- or D-amino acid other than D-arginine, D-lysine; L-arginine or L-lysine and n has a value of 0 to 10; wherein $XD_{11}$ or $XD_{-2}$ represents any D-amino acid other than D-arginine or D-lysine and m has a value of 0 or 1;

wherein
(a) $Arg_1$, $Arg_5$, and $Arg_9$ represent L-arginine; and X represents L-lysine or L-arginine, or
(b) $Arg_1$, $Arg_5$, and $Arg_9$ represent D-arginine; and X represents D-lysine or D-arginine;
wherein ($SP_A$) represents a chemical linker that
(a) consist of a peptide chain of 3 amino acid resides, wherein each residue may be independently selected from any amino acid residue other than D-arginine, D-lysine, L-arginine or L-lysine; or
(b) separates the adjacent amino acid residues by 12.9±1.5 Å;
wherein ($SP_C$) represents a chemical linker that
(a) consists of a single amino acid residue that may be any amino acid residue other than D-arginine, D-lysine, L-arginine or L-lysine; or
(b) separates the adjacent amino acid residues by 7.5±1.5 Å when the molecule is in extended conformation;
and wherein ($SP_B$)-X-($SP_C$) or its reverse, ($SP_C$)-X-($SP_B$) represents a chemical linker
(a) wherein $SP_B$ and $SP_C$ each represent a single amino acid residue that may be independently selected from any amino acid residue other than D-arginine, D-lysine, L-arginine or L-lysine; or
(b) that separates the adjacent amino acid residues $Arg_1$ and $Arg_5$ or $Arg_5$ and $Arg_9$ by 12.9±1.5 Å when the construct is in extended conformation.

6.6.1 The Optional Linking Group

Consensus sequences (xi) to (xiv) are identical to consensus sequences (iii) to (vi), respectively, but for the presence of the BAM-moiety and the optional linker group, (LINK). Therefore, selection of the chemical spacers ($SP_A$), ($SP_B$) and ($SP_C$), which may consist of or comprise exclusively amino acid residues or comprise both chemical linkers and amino acid residues as described herein) proceeds as described herein with respect to consensus sequences (iii) to (vi), including
selection of these chemical spacers to consist of or comprise exclusively amino acid residues according to the embodiments (and combinations thereof) of consensus sequences (i) and (ii) as detailed throughout this disclosure, and
selection of these chemical spacers to comprise both chemical linkers and amino acid residues according to the embodiments (and combinations thereof) of consensus structures (vi) to (x) as detailed throughout this disclosure.

The optional linking group (LINK) may be a peptidic linker. If peptidic linker sequences are used, the linker sequences preferably form a flexible sequence of 2 to 10 residues, more preferably 1 to 5 residues. In a preferred embodiment, the linker sequence contains at least 20%, more preferably at least 40% and even more preferably at least 50% Gly or β-alanine residues. Nonlimiting examples of linking groups include, GlyGlyGlyGlyGly (SEQ ID NO:23), GlyGlyGlyGly (SEQ ID NO:24), GlyGlyGly, CysGlyGly or GlyGlyCys, etc. Appropriate linker sequences are well known to and can be easily selected and prepared by a person skilled in the art. The optional linker group may be composed of D-amino acids, L amino acids, and/or combinations thereof.

Alternatively, the BAM and the transporter moiety may be linked by chemical coupling in any suitable manner known in the art or described herein, such as cross-linking methods. However, attention is drawn to the fact that many known chemical cross-linking methods are non-specific, i.e., they do not direct the point of coupling to any particular site on the carrier/transporter moiety or on the cargo moiety (e.g., BAM). Thus, the use of non-specific cross-linking agents may attack functional sites or sterically block active sites, rendering the one or both of the BAM/transporter components of the inventive BAM-conjugate molecule biologically inactive. It is referred to the knowledge of the skilled artisan to block potentially reactive groups by using appropriate protecting groups. Alternatively, the use of the powerful and versatile oxime and hydrazone ligation techniques, which are chemo-selective entities that can be applied for the cross-linking of component (A) to component (B), may be employed. This linking technology is described, e.g., by Rose et al. (1994), *JACS* 116, 30.

Coupling specificity can also be increased by direct chemical coupling to a functional group found only once or a few times in the BAM component and the transporter moiety. Coupling of the two components of the inventive peptide-conjugate molecule can be accomplished via a coupling or conjugating agent as is known in the art, including standard (poly-) peptide synthesis coupling reagents such as HOBt, HBTU, DICI, TBTU. There are several intermolecular cross-linking reagents which can be utilized, see, for example, Means and Feeney, *Chemical Modification of Proteins, Holden-Day,* 1974, pp. 39-43. These reagents include, but are not limited to, N-succinimidyl 3-(2-pyridyldithio)propionate (SPDP) or N,N'-(1,3-phenylene) bismaleimide; N,N'-ethylene-bis-(iodoacetamide) or other such reagent having 6 to 11 carbon methylene bridges; and 1,5-difluoro-2,4-dinitrobenzene. Other cross-linking reagents useful for this purpose include, but are not limited to: p,p'-difluoro-m,m'-dinitrodiphenylsulfone; dimethyl adipimidate; phenol-1,4-disulfonylchloride; hexamethylenediisocyanate or diisothiocyanate, or azophenyl-p-diisocyanate; glutaraldehyde and disdiazobenzidine. Cross-linking reagents may also be homobifunctional, i.e., having two functional groups that undergo the same reaction. A preferred homobifunctional cross-linking reagent is bismaleimidohexane (BMH). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of proteins (or polypeptides) that contain cysteine residues. Cross-linking reagents may also be heterobifunctional. Heterobifunctional cross-linking agents have two different functional groups, for example an amine-reactive group and a thiol-reactive group, that will cross-link two proteins having free amines and thiols, respectively. Non-limiting examples of heterobifunctional cross-linking agents are Succinimidyl-4-(N-maleimidomethyl)-cyclohexane-1-carboxylate (SMCC), m-maleimidobenzoyl-N-hydroxysuccinimide ester (MBS), and succinimide 4-(p-maleimidophenyl)butyrate (SMPB), an extended chain analog of MBS. The succinimidyl group of these cross-linkers reacts with a primary amine, and the thiol-reactive maleimide forms a covalent bond with the thiol of a cysteine residue. Because cross-linking reagents often have low solubility in water, a hydrophilic moiety, such as a sulfonate group, may be added to the cross-linking reagent to improve its water solubility. Sulfo-MBS and sulfo-SMCC are examples of cross-linking reagents modified for water solubility. Many cross-linking reagents yield a conjugate that is essentially non-cleavable under cellular conditions, which would not be preferred. Therefore, some cross-linking reagents contain a covalent bond, such as a disulfide, that is cleavable under cellular conditions. For example, Traut's reagent, dithiobis(succinimidylpropionate) (DSP), and N-succinimidyl 3-(2-pyridyldithio)propionate (SPDP) are well-known cleavable cross-linkers. The use of a cleavable cross-linking reagent permits the cargo moiety, e.g., BAM, to separate from the novel transporter moiety after delivery into the target cell. For this purpose, direct disulfide linkage may also be useful. Chemical cross-linking may also include the use of spacer arms. Spacer arms provide intramolecular flexibility or adjust intramolecular distances between conjugated moieties and thereby may help preserve biological activity. A spacer arm may be in the form of a protein (or polypeptide) moiety that includes spacer amino acids, e.g., proline. Alternatively, a spacer arm may be part of the cross-linking reagent, such as in "long-chain SPDP" (e.g., Pierce Chem. Co., Rockford, Ill., cat. No. 21651 H). Numerous cross-linking reagents, including the ones discussed above, are commercially available. Detailed instructions for their use are readily available from the commercial suppliers. A general reference on protein cross-linking and conjugate preparation is: Wong, *Chemistry of Protein Conjugation and Cross-Linking*, CRC Press (1991).

It will be appreciated that the different components of the BAM-conjugate molecule should be coupled in a manner so that the different components can still convey at least part of their individual activity and/or properties to the entire transporter cargo conjugate molecule. For example, coupling of the components shall preferably not lead to a total loss in targeting to C4S.

6.6.2 The BAM Moiety

The invention encompasses any BAM known or expected to be a therapeutically active component for the treatment or prevention of a disease, disorder or condition, or amelioration of a symptom thereof, e.g., such as chemical compounds, proteins, liposomes, nanoparticles and (poly-)peptides. Additionally or alternately, the BAM may be a detectable marker of use in the diagnosis of a disease or condition such as a fluorescent dye, a radioactive label or a chemoluminesent group.

A. Cytotoxic Drugs

Preferably the BAM of the "BAM-conjugate" of the invention is a pharmaceutical drug, e.g., selected from cytotoxic or anti-tumor drugs which are suitable as a chemotherapy drug. In general, chemotherapy drugs suitable for component (B) can be divided into three main categories based on their mechanism of action. They may (a) stop the synthesis of preDNA molecule building blocks. These agents work in a number of different ways. DNA building blocks are folic acid, heterocyclic bases, and nucleotides, which are made naturally within cells. All of these agents work to block some step in the formation of nucleotides or deoxyribonucleotides (necessary for making DNA). When these steps are blocked, the nucleotides, which are the building blocks of DNA and RNA, cannot be synthesized. Thus the cells cannot replicate because they cannot make DNA without the nucleotides. Examples of drugs in this class include methotrexate (Abitrexate®), fluorouracil (Adrucil®), hydroxyurea (Hydrea®), and mercaptopurine (Purinethol®), thioguanine, tocoferol, or, more generally, any nucleotide analogue, e.g., 2'-deoxycytidine analogues;

(b) directly damage the DNA in the nucleus of the cell. These agents chemically damage DNA and RNA. They disrupt replication of the DNA and either totally halt replication or cause the manufacture of nonsense DNA or RNA (i.e., the new DNA or RNA does not code for anything useful). Examples of drugs in this class include cisplatin (Platinol®) and antibiotics-daunorubicin (Cerubidine®), doxorubicin (Adriamycin®) belonging to the class of anthracycline antitumor agents and etoposide (VePesid®) or any intercalator; further included are radionuclides (e.g., alpha-radionucleids) commonly used in target cancer treatment (e.g., Bismuth-213); or (c) effect the synthesis or breakdown of the mitotic spindles. Mitotic spindles serve as molecular railroads with "North and South Poles" in the cell when a cell starts to divide itself into two new cells. These spindles are very important because they help to split the newly copied DNA such that a copy goes to each of the two new cells during cell division. These drugs disrupt the formation of these spindles and therefore interrupt cell division. Examples of drugs in this class of mitotic disrupters include: Vinblastine (Velban®), Vincristine (Oncovin® and Paclitaxel (Taxol®).

The BAM of the "BAM-conjugate" of the invention may act according to one of the above modes of action. In other terms, each of the classes of anti-tumor drugs, i.e., alkylating agents, nitrosoureas, antimetabolites, plant alkaloids, anti-tumor antibiotics, and steroid hormones may be used as component the BAM of the inventive transporter cargo conjugate molecule. To describe these drug classes in more detail it is emphasized that each anti-cancer drug may also be categorized according to its effect on the cell cycle and cell chemistry as disclosed above. Alkylating agents kill cells by directly attacking DNA.

Alkylating agents may be used, in particular, in the treatment of chronic leukemias, Hodgkin's disease, lymphomas, and certain carcinomas of the lung, breast, prostate and ovary. Cyclophosphamide is an example of a commonly used alkylating agent. Nitrosoureas act similarly to alkylating agents and also inhibit changes necessary for DNA repair. These agents cross the blood-brain barrier and are therefore used to treat brain tumors, lymphomas, multiple myeloma, and malignant melanoma. Carmustine and lomustine are the major drugs in this category. Antimetabolites are drugs that block cell growth by interfering with certain activities, usually DNA synthesis. Once ingested into the cell they halt normal development and reproduction. All drugs in this category affect the cell during the "S" phase of the cell cycle. Antimetabolites may be used in the treatment of acute and chronic leukemias, choriocarcinoma, and some tumors of the gastrointestinal tract, breast and ovary. Non-limiting examples of commonly used antimetabolites are 6-mercaptopurine and 5-fluorouracil (5FU). Antitumor antibiotics are a diverse group of compounds. In general, they act by binding with DNA and preventing RNA synthesis. These agents are widely used in the treatment of a variety of cancers. The most commonly used drugs in this group are doxorubicin (Adriamycin), mitomycin-C, and bleomycin. Plant (vinca) alkaloids are anti-tumor agents derived from plants. These drugs act specifically by blocking cell division during mitosis. They are commonly used in the treatment of acute lymphoblastic leukemia, Hodgkin's and non-Hodgkin's lymphomas, neuroblastomas, Wilms' tumor, and cancers of the lung, breast and testes. Vincristine and vinblastine are commonly used agents in this group. Steroid hormones are useful in treating some types of tumors. This class includes adrenocorticosteroids, estrogens, antiestrogens, progesterones, and androgens. Although their specific mechanism of action is not clear, steroid hormones modify the growth of certain hormone-dependent cancers. Tamoxifen is an example, which is used for estrogen dependent breast cancer. All of the above-mentioned tumor species may be treated by the inventive BAM-conjugate molecules comprising as the BAM any of the above antitumor agents.

One group of cytotoxic or anti-tumor drugs, which may be used as the BAM component of the "BAM-conjugate" of the invention is selected from alkylating drugs, antimetabolica, cytostatics or drugs related to hormone treatment. In this context, it is preferred to select as cytotoxic or anti-tumor drugs compounds of metal, in particular platin (derivative) and taxol classes. In particular, the drug moiety is selected from the group of drugs consisting of, for example, cisplatin, transplatin, satraplatin, oxaliplatin, carboplatin, nedaplatin, chlorambucil, cyclophosphamide, mephalan, azath ioprin, fluorouracil, (6)-mercaptopurine, methrexate, nandrolone, aminogluthemide, medroxyprogesteron, megestrolacetate, procarbazin, docetaxel, paclitaxel, irinotecan, epipodophyllotoxin, podophyllotoxin, vincristine, vinblastine, docetaxel, daunomycin, daunorubicin, doxorubicin, mitoxantrone, topotecan, bleomycin, gemcitabine, fludarabine, navelbine and 5-FUDR. Particularly preferred is the class of metal-containing anticancer drugs, e.g., the class of platinum compounds.

Further cytotoxic or anti-tumor drugs, which may be used as the BAM component of the "BAM-conjugate" of the invention are Alitretinoin, Altretamine, Azathioprine, Bicalutamide, Busulfan, Bortezomib, Capecitabine, Carfilzomib, Cyclophosphamide, Exemestane, Letrozole, Finasteride, Fostamatinib, Gefitinib, Imatinib, Lenalidomide, Marizomib, Megestrol Acetate, Nilotinib, Triptorelin, Temozolomide, Mifepristone, Tretinoin, Tamoxifen, Teniposide, Peplomycin sulfate or the class of camptothecins.

Further cytotoxic or anti-tumor drugs that may be used as the BAM component of the "BAM-conjugate" of the invention are radionuclides (e.g., alpha particle emitting radionucleids) such as those commonly used in target cancer therapies well known in the art. Non-limiting examples of such radionucleids that may be of use according to the invention include Molybdenum-99, Technetium-99m, Bismuth-213, Chromium-51, Cobalt-60, Copper-64, Dysprosium-165, Erbium-169, Holmium-166, Iodine-125, Iodine-131, Iridium-192, Iron-59, Lutetium-177, Palladium-103, Phosphorus-32, Potassium-42, Rhenium-186, Rhenium-188, Samarium-153, Selenium-75, Sodium-24, Strontium-89, Xenon-133, Ytterbium-169, Ytterbium-177, Yttrium-90, Radioisotopes of caesium, gold and ruthenium. Also included are Cyclotron Radioisotopes such as Carbon-11, Nitrogen-13, Oxygen-15, Fluorine-18, Cobalt-57, Gallium-67, Indium-111, Iodine-123, Krypton-81 m, Rubidium-82, Strontium-92, Thallium-201. Alternatively or additionally, any of the above non-limiting examples may also be implemented for diagnostic or imaging uses.

Another group of cytotoxic or anti-tumor drugs, which may be used as the BAM component of the "BAM-conjugate" of the invention are indolocarbazole compounds, e.g, staurosporin (and its analogues) and rebeccamycin. It is to be mentioned that compounds belonging to the class of anilinoquinazolines (e.g., gefitinib) are also particularly preferred as the BAM component of the BAM-conjugates of the invention.

A further group of cytotoxic or anti-tumor drugs, which may be used as the BAM component of the "BAM-conjugate" of the invention may be selected from inhibitors of topoisomerases, such as irinotecan, or mitotic kinesins or DHFR.

Additionally, cytotoxic or anti-tumor drugs, which may be used as the BAM component of the "BAM-conjugate" of the invention can be selected from factors inhibiting or stimulating cell proliferation (PDGF), intracellular pathways, e.g., the RAS/RAF signaling pathway, such as a member of the RAF/MEK/ERK signaling pathway (e.g., RAF-1) or mitogen-activated protein kinase pathway, CMGC kinase family (containing CDK (cyclin dependent-kinases), MAPK, GSK3, CLK), Ser/Thr kinases that belong to the AGC kinase family containing PKA, PKG, PKC kinase families, receptor tyrosine kinases involved, e.g., in neovascularization and tumor progression, including vascular endothelial growth factor receptor (VEGFR)-2, VEGFR-3, platelet-derived growth factor receptor β, Flt-3, the endothelin (ET) system, that includes ET-1, ET-2, ET-3, and the $ET_A$ receptor ($ET_{AR}$) and $ET_{BR}$, and c-KIT, which are targeted by, e.g., inhibiting their function, and members of the IGF-family, such as IGF-1, IGF-2, IGF-1 R, IGF2R, etc.

Another group of cytotoxic or anti-tumor drugs, which may be used as the BAM component of the "BAM-transporter conjugate" of the invention may be selected from inhibitors that target tumor cell proliferation and tumor angiogenesis. Particularly preferred in this context are small molecule antitumor kinase inhibitors directed toward targets on malignant cells and/or vascular cells have antiangiogenic activity. Kinase inhibitors such as those directed toward EGFR, Her2/neu, BCR-ABL, c-KIT, PKC, Raf and PI3, are antiangiogenic by virtue of blocking secretion of angiogenic factors by affected malignant cells. Kinase inhibitors such as those directed toward VEGFR2, VEGFR1, PDGFR, PKC, Raf and PI3, are antiangiogenic by effects on vascular cells. Examples of synthetic inhibitors of cyclin dependent kinases (CDKIs) are, e.g., olomoucine, flavopiridol, butyrolactone and their derivatives and thus constrain tumor cell proliferation. On the other hand, antitumor compounds suitable as the BAM component of the inventive peptide-conjugate/BAM-conjugate molecule may be selected from activators of apoptosis programs in cancer cells (e.g., staurosporine) or by down-regulating antiapoptotic proteins, e.g., Bcl-2.

6.7 The Freely-Selectable Positions

As discussed herein, when the consensus structure of the molecule or compound of the invention according to structures (iii) to (vi) consists or comprises exclusively amino acid residues, the targeting moiety that specifically interacts with C4S is represented by the sequence

$Arg_1-X_2-X_3-X_4-Arg_5-X_6-X_7-X_8-Arg_9$ (SEQ ID NO:21, subject to the rules of SEQ ID NO:17 or SEQ ID NO:18;
SEQ ID NO:22, subject to the rules of SEQ ID NO:19 or SEQ ID NO:20)

As detailed herein positions 2, 4, 6, 8 and (3 (where position 7 is defined as a D- or L-arginine or lysine according to the rules set forth herein) or 7 (where position 7 is defined as a D- or L-arginine or lysine according to the rules set forth herein)) have little effect on specific binding of the compounds of the invention to a C4S proteoglycan, thus these positions are referenced herein as freely selectable. As noted herein, use of the charged amino acids arginine or lysine is avoided, as these tend to increase the probability of non-specific interactions with proteoglycans, in general.

Additionally, it is believed that the targeting moieties exhibit specificity for C4S due to the optimal linear arrangement of arginines at positions 1, 5, 9 and an arginine or lysine at position 3 or 7, thus, the remaining amino acids are preferably selected so as to avoid the induction of 3-dimensional structures such as, e.g., α-helices. The propensity for α-helix formation for each of the naturally occurring peptidic amino acids is known, e.g., Chakrabartty et al., *Protein Sci.* 3(1994), 843-852, the ranking from highest to lowest α-helix potential is as follows:

$Ala>Arg^+>Leu>Lys^+>Glu^o>Met>Gln>Glu^->Ile>Tyr>His^o>Ser>Cys>Asn>Asp^->Asp>Trp>Phe>Val>Thr>His^+>Gly>Pro$

Thus, it is preferred that no more than 3 amino acids with a high probability of forming an α-helix are used in the freely selectable positions. Accordingly, in preferred embodiments, no more than 3 alanines are used in the freely selectable positions. In additional or alternative further preferred embodiments, proline is not to be used in the freely selectable position.

Further it is preferred that the freely selectable positions are bulky and/or hydrophobic amino acids, as such amino acids may aid membrane insertion and cell penetration (see, e.g., Rothbard, *Cell-Penetratinq Peptides: Processes and Applications*. Lanel Ü (Ed), CRC Press (2000)). Thus, in preferred embodiments wherein the molecule or compound of the invention consists or comprises a sequence according to consensus sequences (i) or (ii), the freely selectable positions, 2, 4, 6, 8 and (3 (where position 7 is defined as a D- or L-arginine or lysine according to the rules set forth herein) or 7 (where position 7 is defined as a D- or L-arginine or lysine according to the rules set forth herein) are independently selected from Phe, Trp, Tyr, Val, Met, Ile and Leu.

It is known that D-amino acids enhance resistance to proteases and/or other means of protein degradation. Thus, in further preferred embodiments, position 4 or position 6 is a D-amino acid.

It is also noted that the consensus sequence of the compounds of the invention contains optional amino acid residues that act as a proton sponge. In the consensus sequences (i) to (xiv), $(XD_{11})_m$ or $(XD_{-2})_m$ and $(LD_{10})_n$ or $(LD_{-1})_n$, wherein m is 0 or 1 and n is 0-10, represent the optional proton sponge amino acids. The residues of the proton sponge may be selected from among any residue or combination of residues that is(are) known in the art or described herein capable of acting as a proton sponge. In preferred embodiments, $XD_{11}$ or $XD_{-2}$ represents any D-amino acid other than D-arginine or D-lysine (if the residue is present) and $LD_{10}$ or $LD_{-1}$ represents any L- or D-amino acid other than L- or D-arginine or L- or D-lysine (if the residue(s) are present). In the most preferred embodiments, $XD_{11}$ or $XD_{-2}$ represents D-histidine (if the residue is present) and $LD_{10}$ or $LD_{-1}$ represents L- or D-histidine (if the residue(s) are present). As is recognized in the art, the accumulation of specific amino acid residues (e.g., histidine) inside acidic vesicles such as an endosome produces the protein sponge effect. For example, the imidazole ring of histidine is a weak base that has the ability to acquire a cationic charge when the pH of the environment drops below 6, which may further promote membrane fusion and endosome escape.

It is expressly contemplated that the embodiments described in this section and throughout this application, whether identified as preferred (including most preferred) or not, can be independently implemented or can be combined with the other disclosed embodiments in the design or selection of a compound of the invention. Therefore, the consensus sequence and/or targeting moiety of the compound may optionally satisfy none, one, or more than one of the embodiments outlined in this section and/or throughout the description. As a non-limiting example of such combination, the freely selectable positions may each be independently selected from Phe, Trp, Tyr, Val, Met, Ile and Leu, position 4 may be a D-amino acid, n of $(LD_{10})_n$ may be 0 and m of $(XD_{11})_m$ may be 1.

The novel D/L amino acid configuration and/or novel combination of chemical linkers/spacers and/or combination of the compounds of the invention allow a skilled person to define the in vivo or in vitro persistence of the inventive molecule or compound as defined above in the cell, specifically, with a half-life that closely matches the half-life of, e.g., the BAM to be administered into the cell or nucleus prior to degradation of the transporter construct by proteases.

In the context of the present invention, variants and/or fragments of peptides and/or polypeptides preferably comprise or consist of a (poly-)peptide sequence having at least 10%, 20%, 30%, 40%, 50%, 60%, 70%, 80%, or 85%, preferably at least 90%, more preferably at least 95% and most preferably at least 99% sequence identity over the whole length to the sequence of the (poly-)peptides expressly disclosed herein and subject to the rules for selection of the consensus sequence(s).

6.8 Use of Compounds of the Invention

The consensus sequences (i) to (x) of the invention are envisioned as transporter moieties that effect transport across the cell membrane and into the cytoplasm and/or nucleus of a cell. It is common to all of the therapeutic compounds (i.e., BAMs) disclosed herein that they have to cross the cell membrane in order to act as anticancer drugs. By coupling compounds belonging to these classes (compounds directly damaging the DNA in the nucleus of the cell, effecting the synthesis or breakdown of the mitotic spindles or stopping the synthesis of pre-DNA molecule building blocks) to the consensus sequences (i) to (x) of the invention, the entry of the anticancer compounds into the cell is enhanced and/or their solubility is enhanced, thereby increasing the efficacy of these therapeutic compounds. In turn, increased cell take-up and, preferably, better solubility of these compounds in the aqueous environment (e.g., the cytosol) allows to lower the dosage of the therapeutic anti-cancer compound may be achieved.

The consensus sequences of the targeting moieties of the compounds of the invention target, in particular, the C4S proteoglycan. These proteoglycans are preferentially expressed in conjunction with the surface proteins, e.g., CD68, of leukocytes. Indeed, it is likely that leukocytes express no other form of proteoglycan. Accordingly, the molecules and compounds of the invention allow the specific targeting of leukocytes. Therefore, the molecules, compounds and methods of the invention facilitate the efficient delivery of cargo moieties, e.g., BAMs, to leukocytes and provides a general means of selectively delivering a substance of interest into a leukocyte. Thus, it is preferred that the BAM to be conjugated to the transporter moiety be any substance the person skilled in the art knows or expects to exert an effect on leukocyte activity, including therapeutic effects (such as treating, preventing, attenuating or ameliorating a disease), or for the purpose of labeling leukocytes such as for diagnostic purposes or for purposes of scientific research. Of particular interest is the targeting of myeloid cells.

The BAM-conjugates of the invention may be used for the treatment, amelioration, prophylaxis, or diagnosis of a wide range of diseases or conditions in which leukocytes have a pathophysiological involvement. Non-limiting exemplary conditions involving primary or secondary leukocyte disfunction include: neutrophilia, neutropenia, leukopenia, basopenia, basophilia, eosinopenia, eosinophilia, idiopathic hypereosinophilic syndrome, lymphocytic leukocytosis, lymphocytosis, lymphocytopenia, monocytosis, monocytopenia, May Hegglin Anomaly, Pelger-Huet Anomaly, Alder-Reilly Anomaly, Chedial-Higashi syndrome, Job's syndrome (hyper-IgE), lazy leukocyte syndrome, congenital C3 deficiency, chronic granulomatous disease, leukocyte, glucose-6-phosphate dehydrogenase deficiency, myeloperoxidase deficiency-benign, severe combined immunodeficiency disease, DiGeorge's syndrome, Nezelof's syndrome, infantile sex-linked agammaglobulinemia, common variable hypogammaglobulinemia, mucopolysaccharidosis, lipodoses, Gaucher disease, Niemann-pick disease, Fabry disease, Farber's disease, gangliosidoses; Tay Sachs, Sandhoff disease, Krabbe disease, metachromatic leukodystrophy, Wolman's disease, leukemia, acute lymphocytic leukemia (L1, L2, L3), chronic lymphocytic leukemia, all forms of acute myelogenous leukemia (AML), including undifferentiated AML (M0), myeloblastic leukemia (M1), myeloblastic leukemia (M2), promyelocytic leukemia, (M3), myelomonocytic leukemia (M4), monocytic leukemia (M5), erytholeukemia (M6), megakaryoblastic leukemia, (M7), chronic myelogenous leukemia as well as undifferentiated or biphenotypic acute leukemias (leukemias that have both lymphocytic and myeloid features), and all forms of lymphomas including Hodgkin lymphoma, T-cell lymphoma, B-cell lymphoma, lymphoplasmacytic lymphoma, Waldenström macroglobulinemia, multiple myeloma, and follicular lymphoma.

The BAM-conjugates of the invention are of use, either additionally or alternatively, in the treatment of diseases wherein the etiology is primarily dysfunction of myeloid or lymphoid cells. Non-limiting examples of such diseases include the various forms of acute myelogenous leukemia (AML), in particular, Acute Lymphoblastic Leukemia, Acute Myeloblastic Leukemia, Acute Myelogenous Leukemia, Acute Myeloid Leukemia, Acute Promyelocytic Leukemia, Acute Undifferentiated Leukemia, B-cell Chronic Lymphocytic Leukemia, B-cell (acute) Leukemia, Chronic Lymphocytic Leukemia, Chronic Myelocytic Leukemia, Myeloid Leukemia, pre B-cell Leukemia, T-cell Leukemia, T-cell Acute Lymphoblastic Leukemia, T-cell Leukemia (in lung carcinoma), Cutaneous T-cell Leukemia, Human Monocytic Leukemia, Mast cell Leukemia, Mixed Linkage Leukemia, Hairy cell leukemia, T-cell prolymphocytic leukemia, Large granular lymphocytic leukemia, Adult T-cell leukemia, and all forms of lymphomas including Hodgkin lymphoma, T-cell lymphoma, B-cell lymphoma, lymphoplasmacytic lymphoma, Waldenström macroglobulinemia, multiple myeloma, and follicular lymphoma.

Exemplary conditions involving secondary leukocyte dysfunction include infections by any one of the following pathogens: HIV, Epstein Barr Virus, Morbillivirus (measles), Paramyxovirus, Rubivirus, Herpes Virus Type 6, Herpes Virus, Dengue Virus, Herpes Simplex Virus 1, Herpes Simplex Virus 2, Parvovirus, Respiratory Syncytial Virus, Variola Virus, Varicella, Flavivirus, Human T-lymphotropic virus Type 1, Human T-lymphotropic virus Type 2, Human T-lymphotropic virus Type 3, Human T-lymphotropic virus Type 4, Hepatitis A Virus, Hepatitis B Virus, Hepatitis C Virus, Hepatitis D Virus, Hepatitis E Virus, Lassa Virus, Influenza A, Subtypes H1N1 and H3N2 of Influenza A, Influenza B, or Influenza C Virus or Trypanosomatid protozoa, including *Leishmania*. Most preferably, the disease involving secondary leukocyte dysfunction is HIV infection and AIDS or leishmaniasis.

Exemplary conditions and diseases which may be treated, prevented, attenuated or ameliorated by modulating leukocyte activity include acute or chronic inflammatory conditions, including chronic obstructive pulmonary disease (COPD). rheumatoid arthritis (RA), psoriatic arthritis, inflammatory bowel disease, psoriasis, lupus, asthma, allergic reactions, and autoimmune diseases, including but not limited to Acute disseminated encephalomyelitis (ADEM), Addison's disease, Agammaglobulinemia, Alopecia areata, Amyotrophic Lateral Sclerosis, Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behçet's disease, Berger's disease, Bickerstaff's encephalitis, Blau syndrome, Bullous pemphigoid, Cancer, Castleman's disease, Celiac disease, Chagas disease, Chronic inflammatory demyelinating polyneuropathy, Chronic recurrent multifocal osteomyelitis, Chronic obstructive pulmonary disease, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease (including either of the two types of idiopathic inflammatory bowel disease "IBD"), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Drug-induced lupus, Discoid lupus erythematosus, Eczema, Endometriosis, Enthesitis-related arthritis, Eosinophilic fasciitis, Eosinophilic gastroenteritis, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Giant cell arteritis, Glomerulonephritis, Goodpasture's syndrome, Graves' disease, Guillain-Barré syndrome (GBS), Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemia, Idiopathic inflammatory demyelinating diseases, Idiopathic pulmonary fibrosis, Idiopathic thrombocytopenic purpura (See Autoimmune thrombocytopenic purpura), IgA nephropathy, Inclusion body myositis, Chronic inflammatory demyelinating polyneuropathy, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease (LAD), Lou Gehrig's disease (Also Amyotrophic lateral sclerosis), Lupoid hepatitis aka Autoimmune hepatitis, Lupus erythematosus, Majeed syndrome, Ménière's disease, Microscopic polyangiitis, Miller-Fisher syndrome see Guillain-Barre Syndrome, Mixed connective tissue disease, Morphea, Mucha-Habermann disease aka *Pityriasis* lichenoides et varioliformis acuta, Multiple sclerosis, Myasthenia gravis, Myositis, Narcolepsy, Neuromyelitis optica (also Devic's disease), Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with *streptococcus*), Paraneoplastic cerebellar degeneration, Paroxysmal nocturnal hemoglobinuria (PNH), Parry Romberg syndrome, Parsonage-Turner syndrome, Pars planitis, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatic fever, Sarcoidosis, Schizophrenia, Schmidt syndrome another form of APS, Schnitzler syndrome, Scleritis, Scleroderma, Serum Sickness, Sjögren's syndrome, Spondyloarthropathy, Still's disease see Juvenile Rheumatoid Arthritis, Stiff person syndrome, Subacute bacterial endocarditis (SBE), Susac's syndrome, Sweet's syndrome, Sydenham chorea see PANDAS, Sympathetic ophthalmia, Systemic lupus erythematosus see Lupus erythematosus, Takayasu's arteritis, Temporal arteritis (also known as "giant cell arteritis"), Thrombocytopenia, Tolosa-Hunt syndrome, Transverse myelitis, Ulcerative colitis (one of two types of idiopathic inflammatory bowel disease "IBD"), Undifferentiated connective tissue disease different from Mixed connective tissue disease, Undifferentiated spondyloarthropathy, Urticarial vasculitis, Vasculitis, Vitiligo, and Wegener's granulomatosis.

6.8.1 Haematological Malignancies

In a preferred embodiment, the "BAM-conjugate" of the invention may be used for the treatment or amelioration of various haematological malignancies, such as acute lymphoblastic leukemia (ALL), chronic lymphocytic leukemia, chronic myeloid (or myelogenous) leukemia (CML), all forms of lymphoma and myeloma, and, in particular, all forms of acute myeloid (or myelogenous) leukemia (AML).

AML is a heterogeneous group of diseases, characterized by uncontrolled proliferation of clonal neoplastic precursor cells, and impaired production of normal haematopoiesis, leading to neutropenia, anaemia and thrombocytopenia. For prognostic and therapeutic purposes the World Health Organization (WHO) has provided the following broad classification for AML:

AML with certain genetic abnormalities, including
AML with a translocation between chromosomes 8 and 21
AML with a translocation or inversion in chromosome 16
AML with changes in chromosome 11
APL (M3), which usually has translocation between chromosomes 15 and 17
AML with multilineage dysplasia (more than one abnormal myeloid cell type is involved)
AML related to previous chemotherapy or radiation
AML not otherwise specified, including
Undifferentiated AML (M0)
AML with minimal maturation (M1)
AML with maturation (M2)
Promyelocytic leukemia, (M3),
Acute myelomonocytic leukemia (M4)
Acute monoblastic leukemia (M5a) acute monocytic leukemia (M5b)
Acute erythroid leukemia (M6)
Acute megakaryoblastic leukemia (M7)
Acute basophilic leukemia
Acute panmyelosis with fibrosis
Myeloid sarcoma (also known as granulocytic sarcoma or chloroma)
Undifferentiated or biphenotypic acute leukemias (leukemias that have both lymphocytic and myeloid features). Sometimes called ALL with myeloid markers, AML with lymphoid markers, or mixed lineage leukemias.

Any of the conventional chemotherapeutic agents as specified above may be used as the biologically active moiety conjugated to the transporter peptides of the invention for the treatment of AML.

Preferably, for the treatment of AML, the BAM is selected from one of the following chemotherapeutic agents:

anti-metabolites such as cytosine arabinosides including cytarabine, purine analogues such as thioguanine, antifolates including trimethopin and pemetred, or pyrimidine analogues including gemcitabine and flouroacil;

topoisomerase inhibitors, such as the anthracyclines, including daunorubicin, adriamycin (doxorubicin) epirubicin, idarubicin, ansamycin, and MEN 10755; the quinoline alkaloids, including camptothecin, SN-38, DX-8951f, topotecan, 9-aminocamptothecin, BN 80915, irinotecan, DB 67, BNP 1350, exatecan, lurtotecan, ST 1481, and CKD 602; the podophyllotoxin analogues etoposide and teniposide, and the anthracenediones, mitoxantrone and amsacrine or other natural products include azathioprine; brequinar; phenoxizone biscyclopeptides, such as dactinomycin; basic glycopeptides, e.g., bleomycin; anthraquinone glycosides, such as plicamycin (mithramycin); anthracenediones, e.g., mitoxantrone; azirinopyrrolo indolediones, e.g., mitomycin; macrocyclic immunosuppressants, e.g., cyclosporine, FK-506 (tacrolimus, prograf), rapamycin, etc.; and the like;

agents that interfere with microtubule assembly, such as the family of vinca alkaloids including vinca alkaloids include vinblastine, vincristine; vinorelbine, vindesine; vindoline and vincamine; the taxanes and diterpenes, including paclitaxel and docetaxel, metal complexes, e.g., cisplatin (cis-DDP), carboplatin, etc.; ureas, e.g., hydroxyurea; and hydrazines, e.g., N-methylhydrazine, arsenic trioxide;

retinoids, e.g., vitamin A, 13-cis-retinoic acid, trans-retinoic acid, isotretinoin, etc.; carotenoids, e.g., beta-carotene, vitamin D, etc.

A growing body of evidence documents that the myeloid malignancies, including the various forms of AML are caused by genetic mutations that constitutively activate enzymes involved in signal transduction. Accordingly, in certain embodiments, the BAM-conjugates of the invention may comprise a BAM moiety designed to target these enzymes, downstream mediators of these enzymes or one or more sequalae of their constitutive activity. Non-limiting examples of such enzymes and/or downstream effectors include farnesyl transferase; vascular endothelial growth factor and other angiogenic proteins; enzymes that contribute to the enhanced proliferative and survival capacity of leukemia blasts, such as FLT3 or RAS; enzymes that contribute to impaired hematopoietic differentiation, such as HDAC inhibitors, the anti-apoptotic gene BCL-2, inhibitors of M-CSF, af10, alox 12, arhgef12, arnt, axl, bax, bad, bcl, bcl3, bcl6, btg1, cav1, cbfb, cdc23, cdh17, cdx2, cebpa, clc, cr1, crebbp, dek, dleu1, dleu2, egfr, ets1, evi2a, evi2b, foxo3a, fus, gli2, gmps, hox11, hoxa9, irf1, kit, laf4, lcp1, ldb1, lmo1, lmo2, lyl1, madh5, mll3, mllt2, mllt3, mov10l1, mtcp1, myc, nfkb2, notch1, notch3, npm1, nup214, nup98, p53, pbx1, pbx2, pbx3, pbxp1, pitx2, pml, rab7, rgs2, runx1, set, sp140, tal1, tal2, tcl1b, tcl6, thra, tra, and znfn1a1.

In line with this, more recently, genotype specific drug targets for the treatment of the various forms of AML have been identified. Such targeted therapies include in particular protein-kinase inhibitors, including inhibitors of tyrosine kinases (Flt3, c-kit, BCR-ABL), Aurora kinases and other components of intracellular signaling pathways (e.g., Ras).

In a preferred embodiment, the biologically active moiety conjugated to the transporter moiety of the invention may be an agent which interferes with such aberrant signal transduction, such as farnesyl transferase inhibitors, histone deacetylase and proteosome inhibitors, antiangiogenesis agents, FLT3 inhibitors, apoptosis inhibitors or inhibitors of M-CSF.

These agents may selectively inhibit a specific component of the signaling pathway or may interact with various components, such as the multi-kinase inhibitor sorafenib.

Protein kinase inhibitors which may be used in accordance with the present invention include crizotinib, gefitinib, imatinib, erlotinib, pazopanib, sunitinib, sorafenib, dasatenib, lapatinib, lestaurtinib, nilotinib, ruxolitinib, tandutinib, vandetanib, cediranib, seliciclib, midostaurin, L-21649, ABT-869, dovitinib and PKC412, tipifarnib, AFG206, AFG210, and AHL196, AUZ454 and ATH686, SU5416 and SU6668.

Non-limiting examples of BAMs that may be used in the treatment haematological malignancies other than acute myeloid leukemia according to the methods disclosed herein include protease inhibitors (e.g., bortezomib, carfilzomib, marizomib), mTOR inhibitors (e.g., rapamycin), inhibitors of protein kinases primarily expressed in leukocytes (e.g., fostamatinib) and epigenetic modifying drugs (compounds acting on the writing and/or erasing or the epigenetic code, e.g., vorinostat).

6.8.2 Inflammatory Conditions And Autoimmune Diseases

The molecules and compounds of the invention may also be used in the treatment or prevention of inflammatory conditions; diseases or conditions associated with autoimmune disease and disorders; and/or or amelioration of the symptoms of such inflammatory conditions and/or autoimmune disease. Non-limiting examples of conditions that may be treated with the compounds and methods of the invention include Acute disseminated encephalomyelitis (ADEM), Addison's disease, Agammaglobulinemia, Alopecia areata, Amyotrophic Lateral Sclerosis, Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behçet's disease, Berger's disease, Bickerstaff's encephalitis, Blau syndrome, Bullous pemphigoid, Cancer, Castleman's disease, Celiac disease, Chagas disease, Chronic inflammatory demyelinating polyneuropathy, Chronic recurrent multifocal osteomyelitis, Chronic obstructive pulmonary disease, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease (one of two types of idiopathic inflammatory bowel disease "IBD"), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Drug-induced lupus, Discoid lupus erythematosus, Eczema, Endometriosis, Enthesitis-related arthritis, Eosinophilic fasciitis, Eosinophilic gastroenteritis, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Giant cell arteritis, Glomerulonephritis, Goodpasture's syndrome, Graves' disease, Guillain-Barré syndrome (GBS), Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemia, Idiopathic inflammatory demyelinating diseases, Idiopathic pulmonary fibrosis, Idiopathic thrombocytopenic purpura (See Autoimmune thrombocytopenic purpura), IgA nephropathy, Inclusion body myositis, Chronic inflammatory demyelinating polyneuropathy, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease (LAD), Lou Gehrig's disease (Also Amyotrophic lateral sclerosis), Lupoid hepatitis aka Autoimmune hepatitis, Lupus erythematosus, Majeed syndrome, Ménière's disease, Microscopic polyangiitis, Miller-Fisher syndrome see Guillain-Barre Syndrome, Mixed connective tissue disease, Morphea, Mucha-Habermann disease aka *Pityriasis lichenoides et varioliformis acuta*, Multiple sclerosis, Myasthenia gravis, Myositis, Narcolepsy, Neuromyelitis optica (also Devic's disease), Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with *streptococcus*), Paraneoplastic cerebellar degeneration, Paroxysmal nocturnal hemoglobinuria (PNH), Parry Romberg syndrome, Parsonage-Turner syndrome, Pars planitis, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatic fever, Sarcoidosis, Schizophrenia, Schmidt syndrome another form of APS, Schnitzler syndrome, Scleritis, Scleroderma, Serum Sickness, Sjögren's syndrome, Spondyloarthropathy, Still's disease see Juvenile Rheumatoid Arthritis, Stiff person syndrome, Subacute bacterial endocarditis (SBE), Susac's syndrome, Sweet's syndrome, Sydenham chorea see PANDAS, Sympathetic ophthalmia, Systemic lupus erythematosis see Lupus erythematosis, Takayasu's arteritis, Temporal arteritis (also known as "giant cell arteritis"), Thrombocytopenia, Tolosa-Hunt syndrome, Transverse myelitis, Ulcerative colitis (one of two types of idiopathic inflammatory bowel disease "IBD"), Undifferentiated connective tissue disease different from Mixed connective tissue disease, Undifferentiated spondyloarthropathy, Urticarial vasculitis, Vasculitis, Vitiligo, and Wegener's granulomatosis.

Non-limiting Examples of BAMs that may used in the treatment of such conditions include COX-2 inhibitors, prednisone, pazopanib, famotidine, dalfampridine, pegloticase, esomeprazole, aspirin, celecoxib, diclofenac, valdecoxib, rofecoxib, diflunisal, etodolac, fenoprofen, flurbiprofen, ibuprofen, indomethacin, ketoprofen, ketorolac, mefenamic acid, meloxicam, nabumetone, naproxen, oxaprozin, piroxicam, sulindac, tolmetin, lansoprazole, meclofenamate, triamcinolone, methylprednisolone, betamethasone, budesonide, prednisolone, hydrocortisone, dexamethasone and cortisone.

6.8.3 Protozoal Diseases And Infectious Conditions

The molecules and compounds of the invention may also be used in the treatment or prevention of diseases and conditions associated with protozoal infections or other infectious conditions, and/or or amelioration of the symptoms associated therewith. Non-limiting examples of such diseases and conditions that may be treated with the compounds and methods of the invention include *Acinetobacter* infections, Actinomycosis, African sleeping sickness (African trypanosomiasis), AIDS (Acquired immunodeficiency syndrome), Amebiasis, Anaplasmosis, Anthrax, Arcanobacterium haemolyticum infection, Argentine hemorrhagic fever, Ascariasis, Aspergillosis, Astrovirus infection, Babesiosis, *Bacillus cereus* infection, Bacterial pneumonia, Bacterial vaginosis (BV), *Bacteroides* infection, Balantidiasis, *Baylisascaris* infection, BK virus infection, Black *piedra, Blastocystis hominis* infection, *Blastomycosis*, Bolivian hemorrhagic fever, *Borrelia* infection, Botulism (and Infant botulism), Brazilian hemorrhagic fever, Brucellosis, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, Chlamydia, *Chlamydophila pneumoniae* infection, Cholera, Chromoblastomycosis, Clonorchiasis, *Clostridium difficile* infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fasciolopsiasis, Fasciolosis, Fatal familial insomnia (FFI), Filariasis, Food poisoning by *Clostridium perfringens*, Free-living amebic infection, *Fusobacterium* infection, Gas gangrene (Clostridial myonecrosis), Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome (HPS), *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human *ewingii* ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Melioidosis (Whitmore's disease), Meningitis, Meningococcal disease, Metagonimiasis, Microsporidiosis, Molluscum contagiosum (MC), Mumps, Murine typhus (Endemic typhus), *Mycoplasma pneumonia*, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American *blastomycosis*), Paragonimiasis, Pasteurellosis, Pelvic inflammatory disease (PID), Pertussis (Whooping cough), Plague, Pneumococcal infection, *Pneumocystis pneumonia* (PCP), Pneumonia, Poliomyelitis, *Prevotella* infection, Primary amoebic meningoencephalitis (PAM), Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsialpox, Rift Valley fever (RVF), Rocky mountain spotted fever (RMSF), Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, Tetanus (Lockjaw), *Tinea barbae* (Barber's itch), *Tinea capitis* (Ringworm of the Scalp), *Tinea corporis* (Ringworm of the Body), *Tinea cruris* (Jock itch), Tinea manuum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans (OLM)), Toxocariasis (Visceral Larva Migrans (VLM)), Toxoplasmosis, Trichinellosis, Trichomoniasis, Trichuriasis (Whipworm infection), Tuberculosis, Tularemia, Ureaplasma urealyticum infection, Venezuelan equine encephalitis, Venezuelan hemorrhagic fever, Viral pneumonia, West Nile Fever, White piedra (Tinea blanca), Yersinia pseudotuberculosis infection, Yersiniosis, Yellow fever and Zygomycosis.

Non-limiting Examples of BAMs that may used in the treatment of such conditions include chloroquine, mefloquine, primaquine, proguanil hydrochloride, proguanil hydrochloride with atovaquone, pyrimethamine, sulfadoxine, quinine, quinoline, doxycycline, clindamycin, artesunate, diloxanide, metronidazole, tinidazole, mepacrine hydrochloride, amphotericin, pentamidine, pyrimethamine, sulfadiazine, azithromycin, atovaquone, trimethoprim-sulphamethoxazole, trimethoprim, dapsone, atovaquone, pentamidine isetionate, amodiaquine, chloroguanide, eflornithine, hydroxychloroquine, iodoquinol, meglumine antimonate, melarsoprol, nifurtimox, paromomycin, sodium stibogluconate, suramin, tryparsamide.

6.8.4 HIV/AIDS

It is well established that leucocytes, in particular macrophages play a crucial role in HIV-1 infection. They are among the first cells infected by HIV-1, and have been proposed to form a reservoir of HIV-1 in infected persons. They also serve as a means of spreading virus to other tissues such as the brain. Moreover, the virus may be stored here while remaining hidden from potentially neutralising antibodies or other forms of immune response.

In light if the above, the transport moieties of the invention, which selectively target macrophages and facilitate intracellular transport are ideally suited as carrier moieties of intracellular HIV agents.

Thus, the BAM which may be conjugated to the transport moiety of the invention may in particular be an NRTI (nucleoside or nucleotide reverse transcriptase inhibitor) including zidovudine, didanosine, stavudine, lamivudine, emtricitabine, abacavir and Tenofovir, apricitabine elvucitabine, OBP-601, amdoxovir, epivir, retrovir, stavudine, zalcitabine, AZT, stavudine, 4-Ed4T, Amdoxovir, Dexelvucitabine, DOT (dioxolane thymidine), Fosalvudine, GS-9131, GS-9148, IDX12899, IDX12989, Quinolones, Racivir, Thiovir, TSAO-T derivatives;
- an NNRTI (non-nucleoside reverse transcriptase inhibitor) including nevirapine, delaviradme, efavirenz, etravinne and rilpivi[pi]ne, etravirine, HBY097, IDX899, V026048, RDEA806, RDEA427, RDEA640, UK-435061; or
- a protease inhibitor including ritonavir, tipranavir, saquinavir, nelfinavir, indinavir, amprenavir, fosamprenavir, atazanavir, lopinavir, darunavir (TMC-1 14), lasinavir and brecanavir (VX-385), GRL-02031, SPI-256.

6.8.5 Anti-Protozoal Agents/Leishmaniasis

*Leishmania* are protozoa belonging to the order Kinetoplastida and the family Trypanosomatidae. Leishmaniasis is a vector-borne disease that is transmitted by sandflies. Human infection is caused by about 30 different species that infect mammals. These include the *L. donovani* complex with 3 species (*L. donovani, L. infantum*, and *L. chagasi*); the *L. mexicana* complex with 3 main species (*L. mexicana, L. amazonensis*, and *L. venezuelensis*); *L. tropica; L. major, L. aethiopica*; and the subgenus *Viannia* with 4 main species (*L.* (*V.*) *braziliensis, L.* (*V.*) *guyanensis, L.* (*V.*) *panamensis*, and *L.* (*V.*) *peruviana*). The different species are morphologically indistinguishable, but they can be differentiated by isoenzyme analysis, molecular methods, or monoclonal antibodies.

Leishmaniasis is responsible for various types of diseases, including visceral leishmaniasis, cutaneous leishmaniasis (of localized or diffuse type) and mucocutaneous leishmaniasis. This variability of the clinical features results from both the diversity of the *Leishmania* species and the immune response of the hosts.

In humans as well as in other mammals, the parasite is inoculated through the skin as a flagellated, extracellular promastigote by its arthropod vector. In its mammalian host, *Leishmania* promastigotes must first evade complement-mediated lysis until they are engulfed by a macrophage. The *Leishmania* promastigote then differentiates into the more resistant amastigotes stage and remains an obligate intracellular pathogen infecting the hematopoietic cells of the monocyte/macrophage lineage. Sequestering itself insides the cells of the host allows *Leishmania* to escape many of the immune responses that would otherwise be directed against it. However, in order to survive the antimicrobial activities of its host cell and to prevent activation of an effective immune response, the various *Leishmania* species have evolved complex mechanisms to subvert normal macrophage function, particularly those involved in immune surveillance and macrophage activation, at either the protein or gene expression level.

In addition to repressing the microbicidal activities of the host macrophage, *Leishmania* inhibits the ability of the host cell to display parasite antigens to other components of the immune system. Thus, *Leishmania* prevents the activation of an effective immune response by inhibiting production of a number of cytokines, particularly those involved in the inflammatory response (IL-1 and tumor necrosis factor alpha [TNF-$\alpha$]) or in T-lymphocyte activation (IL-12)). The powerful ability of *Leishmania* to shut down the macrophage antimicrobial machinery allows the parasite to avoid the initial innate immune response and create a safe environment for proliferation. Moreover, the hidden location within the host macrophage is largely responsible for the lack of effective chemotherapy as it impairs the accession of therapeutic drugs.

In order to enhance the antileishmanial activity and to reduce toxicity of the medication, liposomal drug delivery systems have been developed so as to target the mononuclear phagocyte system. Thus, for example, liposomal amphotericin B has been used to treat visceral leishmaniasis.

Nevertheless, to date, pentavalent antimony (Sb), which has been developed more than 50 years ago, remains the first-line treatment for the treatment of Leishmaniasis, despite of its poor efficacy and side effects. There is thus a substantial need for an effective antileishmanial agent, which selectively targets the macrophage host cells so as to increase antileishmanial activity and to reduce toxicity. By virtue of their ability to specifically target myeloid cells, the compounds of the invention may be used to transport and deliver agents with anti-leishmanial activity to the infected macrophage host cells.

Thus, in accordance with one preferred embodiment of the invention, the BAM which may be conjugated to form the BAM-conjugate to the invention may be an agent with anti-protozoal activity, including but not limited to chloroquine, mefloquine, primaquine, proguanil hydrochloride, proguanil hydrochloride with atovaquone, pyrimethamine, sulfadoxine, quinine, quinoline, doxycycline, clindamycin, artesunate, diloxanide, metronidazole, tinidazole, mepacrine hydrochloride, amphotericin, pentamidine, pyrimethamine, sulfadiazine, azithromycin, atovaquone, trimethoprim-sulphamethoxazole, trimethoprim, dapsone, atovaquone, pentamidine isetionate, amodiaquine, chloroguanide, eflornithine, hydroxychloroquine, iodoquinol, meglumine antimonate, melarsoprol, nifurtimox, paromomycin, sodium stibogluconate, suramin and tryparsamide.

6.9 Pharmaceutical Compositions and their Administration

The invention also relates to pharmaceutical compositions comprising the molecules and compounds of the invention, e.g., BAM-conjugates. Such compositions comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The pharmaceutical compositions also may include additional therapeutic agents for the treatment of the given disease being treated. The formulation is made to suit the mode of administration. In general, methods of administering polypeptides are well known in the art and can be applied to administration of the conjugates of the invention.

Administration is by any of the routes normally used for introducing a molecule into ultimate contact with blood. Suitable methods of administering such conjugates in the context of the present invention to a patient are available including oral and parenteral routes. Although more than one route can be used to administer a particular composition, a particular route can often provide a more immediate and more effective action or reaction than another route.

Preferably the BAM-conjugates of the invention are administered by parenteral modes of administration, in particular by intravenous, intraperitoneal, intramuscular, intradermal, subcutaneous intrathecal, intraocular, retrobulbar, intrapulmonary or intraarticular means. Such administration routes and appropriate formulations are generally known to those of skill in the art. Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilises, thickening agents, stabilizers, and preservatives. Carrier polypeptide-target polypeptide conjugates can also be administered via liposomes.

The molecules and compounds of the invention, alone or in combination with other suitable components, can also be made into aerosol formulations (i.e., they can be "nebulised") to be administered via inhalation. Aerosol formulations can be placed into pressurized acceptable propellants, such as dichlorodifluoromethane, propane, nitrogen, and the like.

In a preferred embodiment, the pharmaceutical compositions of the invention are provided in lyophilized form to be reconstituted prior to administration. Buffers and solutions for the reconstitution of the pharmaceutical compositions may be provided along with the pharmaceutical formulation to produce aqueous compositions of the present invention for administration.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, antibacterial and antifungal agents, isotonic and absorption delaying agents and the like.

Pharmaceutically acceptable carriers are determined in part by the particular composition being administered, as well as by the particular method used to administer the composition. Accordingly, there are a wide variety of suitable formulations of pharmaceutical compositions of the present invention.

Pharmaceutically acceptable carriers and excipients are well known in the art, and one or more conjugates of the invention can be formulated into pharmaceutical compositions by well-known methods (see, e.g., Remington: *The Science and Practice of Pharmacy*, 21st edition, A. R. Gennaro, Ed., Mack Publishing Company (2005); *Pharmaceutical Formulation Development of Peptides and Proteins*, S. Frokjaer and L. Hovgaard, Eds., Taylor & Francis (2000); and *Handbook of Pharmaceutical Excipients, 3rd edition*, A. Kibbe, Ed., *Pharmaceutical Press* (2000)).

Pharmaceutical compositions comprising one or more BAM-conjugates of the invention are optionally tested in one or more appropriate in vitro and/or in vivo animal models of disease, to confirm efficacy, tissue metabolism, and to estimate dosages, according to methods well known in the art. Thus, it is understood that the suitable dose of a composition according to the present invention will depend upon the age, health and weight of the recipient, kind of concurrent treatment, if any, frequency of treatment, and the nature of the effect desired. However, the dosage is tailored to the individual subject, as is determinable by one of skill in the art, without undue experimentation. The total dose of therapeutic agent may be administered in multiple doses or in a single dose. In certain embodiments, the compositions are administered alone, in other embodiments the compositions are administered in conjunction with other therapeutics directed to the disease or directed to other symptoms thereof.

The dose administered to a patient, in the context of the present invention, is sufficient to effect a beneficial therapeutic response in the patient over time, or, e.g., to inhibit infection by a pathogen, to reduce or prevent the symptoms of a disease state, or other appropriate activity, depending on the application. The dose is determined by the efficacy of a particular composition/formulation, and the activity, stability or serum half-life of the BAM polypeptide conjugate employed and the condition of the patient, as well as the body weight or surface area of the patient to be treated. The size of the dose is also determined by the existence, nature, and extent of any adverse side-effects that accompany the administration of a particular composition/formulation, or the like in a particular patient.

The invention also relates to the following items:

Item 1, A molecule or compound comprising or consisting of one of the following consensus structure comprising L and D amino acids:

$Arg_1$-$(SP_A)$-$Arg_5$-$(SP_B)$-X-$(SP_C)$-$Arg_9$-$(LD_{10})_n$-$(XD_{11})_m$;

$Arg_1$-$(SP_C)$-X-$(SP_B)$-$Arg_5$-$(SP_A)$-$Arg_9$-$(LD_{10})_n$-$(XD_{11})_m$;

$(XD_{-2})_m$-$(LD_{-1})_n$-$Arg_1$-$(SP_A)$$Arg_5$-$(SP_B)$-X-$(SP_C)$-$Arg_9$; or $(XD_{-2})_m$-$(LD_{-1})_n$-$Arg_1$-$(SP_C)$-X-$(SP_B)$-$Arg_5$-$(SP_A)$-$Arg_9$;

wherein, $LD_{10}$ or $LD_{-1}$ represents any L- or D-amino acid other than D-arginine, D-lysine; L-arginine or L-lysine and n has a value of 0 to 10;

wherein $XD_{11}$ or $XD_{-2}$ represents any D-amino acid other than D-arginine or D-lysine and m has a value of 0 or 1;

wherein
(a) $Arg_1$, $Arg_5$, and $Arg_9$ represent L-arginine; and X represents L-lysine or L-arginine, or
(b) $Arg_1$, $Arg_5$, and $Arg_9$ represent D-arginine; and X represents D-lysine or D-arginine;
wherein ($SP_A$) represents a chemical linker that
(a) consist of a peptide chain of 3 amino acid resides, wherein each residue may be independently selected from any amino acid residue other than D-arginine, D-lysine, L-arginine or L-lysine; or
(b) separates the adjacent amino acid residues by 12.9±1.5 Å;
wherein ($SP_C$) represents a chemical linker that
(a) consists of a single amino acid residue that may be any amino acid residue other than D-arginine, D-lysine, L-arginine or L-lysine; or
(b) separates the adjacent amino acid residues by 7.5±1.5 Å;
and wherein ($SP_B$)-X-($SP_C$) or its reverse, ($SP_C$)-X-($SP_B$) represents a chemical linker
(a) wherein $SP_B$ and $SP_C$ each represent a single amino acid residue that may be independently selected from any amino acid residue other than D-arginine, D-lysine, L-arginine or L-lysine; or
(b) that separates the adjacent amino acid residues $Arg_1$ and $Arg_5$ or $Arg_5$ and $Arg_9$ by 12.9±1.5 Å.

Item 2, The molecule or compound according to item 1, wherein
($SP_A$) represents a chemical linker that separates the adjacent amino acid residues by 12.9±1.5 Å;
($SP_C$) represents a chemical linker that separates the adjacent amino acid residues by 7.5±1.5 Å;
and wherein ($SP_B$)-X-($SP_C$) or its reverse, ($SP_C$)-X-($SP_B$) represents a chemical linker that separates the adjacent amino acid residues $Arg_1$ and $Arg_5$ or $Arg_5$ and $Arg_9$ by 12.9±1.5 Å.

Item 3, The molecule or compound of item 1 or 2, wherein one or more of said chemical linkers is a beta-peptide, a sugar-amino acid based scaffold, a beta-hairpin peptidomimetic, a alpha-helical mimetic or a cyclotide.

Item 4, The molecule or compound of item 1, wherein ($SP_A$) represents a peptide chain consisting of three amino acid residues, each independently selected from any amino acid residue other than D-arginine, D-lysine, L-arginine or L-lysine; and wherein ($SP_B$) and ($SP_C$) each represent a single amino acid residue that may be independently selected from any amino acid residue other than D-arginine, D-lysine, L-arginine or L-lysine.

Item 5, The molecule or compound according to item 1 or 4, wherein ($SP_A$), ($SP_B$) and ($SP_C$) together contain no more than 3 alanine residues.

Item 6, The molecule or compound according to item 1, 4 or 5, wherein ($SP_A$), ($SP_B$) and ($SP_C$) together contain no proline residues.

Item 7, The molecule compound according to any one of items 1 and 4 to 6 wherein ($SP_A$), ($SP_B$) and ($SP_C$) together include one or more amino acids selected from Phe, Trp, Tyr, Val, Met, Ile, and Leu.

Item 8, The molecule or compound according to any one of items 1 and 4 to 7, wherein ($SP_B$) represents a D-amino acid.

Item 9, The molecule or compound according to any one of items 1 to 8, wherein $LD_{10}$ represents L- or D-histidine.

Item 10, The molecule or compound according to any one of items 1 to 9, wherein $XD_{11}$ represents D-histidine.

Item 11, The molecule or compound according to any one of items 1 to 10, wherein m has a value of 1.

Item 12, The molecule or compound according to any one of items 1 to 11, wherein n has a value of 0.

Item 13, The molecule or compound according to any one of items 1 or 4 to 8 having the sequence

| | |
|---|---|
| RSTcaRYRVRh; | (SEQ ID NO: 1) |
| RYFvRIKYRh; | (SEQ ID NO: 2) |
| RYFvRIKARh; | (SEQ ID NO: 3) |
| RAAvRAKYRh; | (SEQ ID NO: 4) |
| RAAvRIKYRh; | (SEQ ID NO: 5) |
| RSTqRYRVRh; | (SEQ ID NO: 6) |
| RSTqRYKVRh; | (SEQ ID NO: 7) |
| RGGgRGKGRh; | (SEQ ID NO: 8) |
| RHHhRHKHRh; | (SEQ ID NO: 9) |
| RVVvRVKVRh; | (SEQ ID NO: 10) |
| RLLlRLKLRh; | (SEQ ID NO: 11) |
| RMMmRMKMRh; | (SEQ ID NO: 12) |
| RIIiRIKIRh; | (SEQ ID NO: 13) |
| RYFVRIKYR; | (SEQ ID NO: 14) |
| RYFvRIKYR; or | (SEQ ID NO: 15) |
| RYFVRiKYR. | (SEQ ID NO: 16) |

Item 14, The molecule or compound of any one of items 1 to 13, further conjugated to a biologically active moiety (BAM).

Item 15, The BAM-conjugate of item 14, wherein said BAM is conjugated to the terminus of said consensus structure according to the following a consensus structure:

(BAM)-(LINK)-$Arg_1$-($SP_A$)-$Arg_5$-($SP_B$)-X-($SP_C$)-$Arg_9$-$(LD_{10})_n$-$(XD_{11})_m$;

(BAM)-(LINK)-$Arg_1$-($SP_C$)-X-($SP_B$)-$Arg_5$-($SP_A$)-$Arg_9$-$(LD_{10})_n$-$(XD_{11})_m$;

$(XD_{-2})_m$-$(LD_{-1})_n$-$Arg_1$-($SP_A$)$Arg_5$-($SP_B$)-X-($SP_C$)-$Arg_9$-(LINK)-(BAM); or $(XD_{-2})_m$-$(LD_{-1})_n$-$Arg_1$-($SP_C$)-X-($SP_B$)-$Arg_5$-($SP_A$)-$Arg_9$-(LINK)-(BAM)

wherein (BAM) represents a biologically active moiety;
wherein (LINK) represents an optional linker group;
wherein, $LD_{10}$ or $LD_{-1}$ represents any L- or D-amino acid other than D-arginine, D-lysine; L-arginine or L-lysine and n has a value of 0 to 10;

wherein XD$_{11}$ or XD$_{-2}$ represents any D-amino acid other than D-arginine or D-lysine and m has a value of 0 or 1;

wherein (a) Arg$_1$, Arg$_5$, and Arg$_9$ represent L-arginine; and X represents L-lysine or L-arginine, or (b) Arg$_1$, Arg$_5$, and Arg$_9$ represent D-arginine; and X represents D-lysine or D-arginine;

wherein (SP$_A$) represents a chemical linker that (a) consist of a peptide chain of 3 amino acid resides, wherein each residue may be independently selected from any amino acid residue other than D-arginine, D-lysine, L-arginine or L-lysine; or (b) separates the adjacent amino acid residues by 12.9±1.5 Å;

wherein (SP$_C$) represents a chemical linker that (a) consists of a single amino acid residue that may be any amino acid residue other than D-arginine, D-lysine, L-arginine or L-lysine; or (b) separates the adjacent amino acid residues by 7.5±1.5 Å;

and wherein (SP$_B$)-X-(SP$_C$) or its reverse, (SP$_C$)-X-(SP$_B$) represents a chemical linker (a) wherein SP$_B$ and SP$_C$ each represent a single amino acid residue that may be independently selected from any amino acid residue other than D-arginine, D-lysine, L-arginine or L-lysine; or (b) that separates the adjacent amino acid residues Arg$_1$ and Arg$_5$ or Arg$_5$ and Arg$_9$ by 12.9±1.5 Å.

Item 16, The BAM-conjugate of item 15, wherein the linker group (LINK) is L- or D-Glu.

Item 17, The BAM-conjugate of any one of items 14 to 16, wherein BAM is conjugated to the Arg$_1$ or Arg$_9$ by a covalent N-terminus amide- or C-terminus ester bond.

Item 18, The BAM conjugate of item 14, wherein said BAM is conjugated to a amino acid residue and/or a chemical group within (SP$_A$), (SP$_B$) or (SP$_C$).

Item 19, The BAM conjugate of item 16, wherein said conjugation is either direct conjugation to an internal residue of said peptide sequence or indirect via a linker group.

Item 20, The BAM-conjugate according to any one of items 14 to 19, wherein the BAM is a mono- or poly saccharide, a cytotoxic agent, an antineoplastic agent, an anti-inflammatory agent, an anti-viral agent, an anti-bacterial agent or an agent for the treatment of protozoan infections.

Item 21, The BAM-conjugate according to any one of items 14 to 19, wherein the BAM is deoxyribose or ribose.

Item 22, A pharmaceutical composition comprising the molecule or compound of item 14 or the BAM-conjugate of any one of items 15 to 21.

Item 23, The pharmaceutical composition of item 22 for use in the treatment of disorders involving leukocytes, selected from neoplastic disease, inflammatory disease, autoimmune disease, immunodeficiency disease, viral-, bacterial-, protozoan or parasitic infections.

Item 24, The pharmaceutical composition according to item 22 for use in the treatment of HIV, Epstein Barr Virus, Morbillivirus, Paramyxovirus, Rubivirus, Herpes Virus, Dengue Virus, Herpes Simplex virus, Parvovirus, Respiratory Syncytial Virus, Variola Virus, Varicella, Flavivirus, Human T-lymphotropic Virus, Hepatitis A, B, C, D, or E Virus, Lassa Virus, or Influenza Virus.

Item 25, The pharmaceutical composition of item 22 for use in the treatment of a disease or condition in which leukocytes have a pathophysiological involvement: neutrophilia, neutropenia, leukopenia, basopenia, basophilia, eosinopenia, eosinophilia, idiopathic hypereosinophilic syndrome, lymphocytic leukocytosis, lymphocytosis, lymphocytopenia, monocytosis, monocytopenia, May Hegglin Anomaly, Pelger-Huet Anomaly, Alder-Reilly Anomaly, Chedial-Higashi syndrome, Job's syndrome (hyper-IgE), lazy leukocyte syndrome, congenital C3 deficiency, chronic granulomatous disease, leukocyte, glucose-6-phosphate dehydrogenase deficiency, myeloperoxidase deficiency-benign, devere combined immunodeficiency disease, DiGeorge's syndrome, Nezelof's syndrome, infantile sex-linked agammaglobulinemia, common variable hypogammaglobulinemia, mucopolysaccharidosis, lipodoses, Gaucher disease, Niemann-pick disease, Fabry disease, Farber's disease, gangliosidoses; Tay Sachs, Sandhoff disease, Krabbe disease, metachromatic, leukodystrophy, Wolman's disease, leukemia, acute lymphatic leukemia (L1, L2, L3), chronic lymphatic leukemia, acute myelogenous leukemia (AML), undifferentiated AML (M0), myeloblastic leukemia (M1), myeloblastic leukemia (M2), promyelocytic leukemia (M3), myelomonocytic leukemia (M4), monocytic leukemia (M5), erytholeukemia (M6), megakaryoblastic leukemia (M7), chronic myelogenous leukemia.

Item 26, The pharmaceutical composition of item 22 for use in the treatment of leishmaniasis.

Item 27, Use of the molecule or compound according to any one of items 1 to 14 for facilitating the transport of a biologically active molecule into myeloid cells.

Item 28, Use of the molecule or compound according to any one of items 1 to 14 for the preparation of a drug-peptide conjugate.

The present invention is not to be limited in scope by the specific embodiments described herein. Indeed, various modifications of the invention in addition to those described herein will become apparent to those skilled in the art from the foregoing description and accompanying figures. Such modifications fall within the scope of the appended claims.

Various publications are cited herein, the disclosures of which are incorporated by reference in their entirety.

7. EXAMPLES 7.1 Peptide Binding to C4S

Approximation of the TAT peptide interaction with C4S was modeled in a computer simulation. The simulation modeled the TAT peptide and C4S molecules in extended conformation, which is the most common form of these molecules in solution. Model results indicated that the Arg residues of TAT residues corresponding to arginines at positions 1, 5 and 9 of the nine-mer peptides according to the invention (e.g., according to the sequence Arg1-X2-X3-X4-Arg5-X6-X7-X8-Arg9 (SEQ ID NO:21 subject to the rules of SEQ ID NO:17 or SEQ ID NO:18; SEQ ID NO:22 subject to the rules of SEQ ID NO:19 or SEQ ID NO:20)) were spaced at favorable intervals to optimally interact with the repeating sulfates of C4S. The distance between the Arg residues of TAT was 13.2 Å, which fit optimally with the repeated spacing of the sulfates on C4S which are separated by 12.9 Å (see, FIG. 1). Additionally, the lysine or arginine at the equivalent positions X3 or X7, would be approximately 6.6 Å from the Arg1 or Arg9 residue, optimally interacting with the carboxylate located 7.5 Å from the sulphate(s) on C4S (FIG. 1). The model implied that the TAT sequences must be in extended conformation to interact with C4S, and excludes any helical constraint for efficient and selective binding.

Approximation of the interaction of a peptide of the invention with C4S was also modeled in a computer simulation. As predicted by the model results described above, the simulation results indicated that arginines at positions 1, 5 and 9 of the nine-mer peptides according to the invention exhibited favorable interactions with the sulfates on the sugars of C4S (e.g., at positions 1, 3 and 7 on the simulated structure depicted in FIG. 2. Additionally, a lysine at position 3 of the nine-mer peptide was able to interact with the carboxylate on the sugar at position 2 of the C4S as modeled in FIG. 2.

The favorable interactions at positions 1, 5 and 9 of the targeting peptides of the invention with the C4S molecule are schematically represented in FIG. 3 using the viral TAT peptide. As determined by the model and as represented in FIG. 3, only Arg at positions 1, 5 and 9 (balls in FIG. 3), and Lys at 3 are engaged in interactions with the sulfates on sugars from C4S at 1, 3 and 7 and the carboxylate at position 2 on C4S, respectively. Further, because the structures are symmetric, Lys +3 can be moved at +7 with identical results.

Figure 4A:
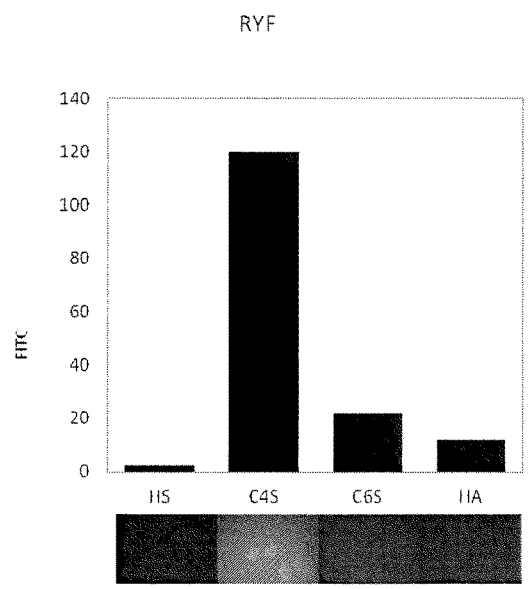
Figure 4B:
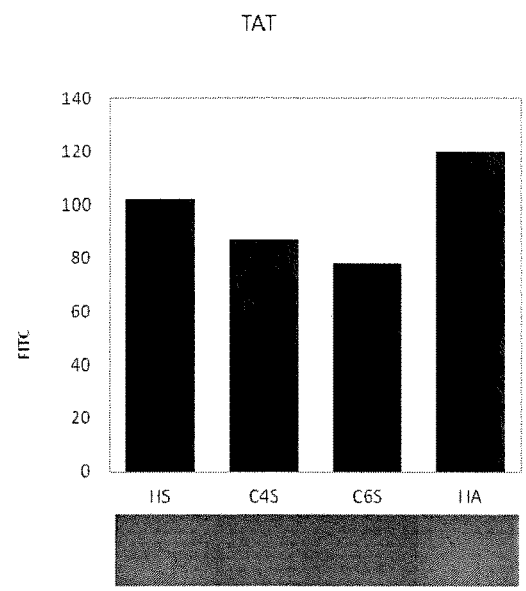

The binding of the nine-mer peptides of the invention to C4S predicted by the models, in particular, as compared to the binding to other proteoglycans was tested using a modified ELISA protocol. ELISA plates were coated overnight with 1 mg/ml of heparin sulphate (HS), chondroitin-4-sulfate (C4S), chondroitin-6-sulfate (C6S) or hyaluronic acid (HA) in PBS. The wells were then washed with PBS and incubated for 1 hour at room temperature with 1 mg/ml of an exemplary peptide of the invention having the sequence RYFvRIKYRh ("RYF"; SEQ ID NO:2) or a standard TAT peptide. The plates were then thoroughly washed with PBS and subsequently photographed with a LUMASCOPE™ luminescent microscope. Images were then quantified using the ImageJ software (FIG. 4). The results presented in FIG. 4 demonstrate, that in contrast to the standard TAT peptide (FIG. 4B), the RYF peptide according to the invention specifically binds to the C4S proteoglycan, and in particular, selectively binds C4S over the other proteoglycans tested (FIG. 4A).

The same modified ELISA protocol was used to examine the impact of altering the chirality of the amino acid residues at positions 1, 5, 9 and 3 or 7 on the binding of the peptides to C4S. FIG. 5 demonstrates that high binding activity was only maintained where all of positions Arg1, Arg5, Arg9 and Arg/Lys3 or Arg/Lys7 had the same chirality (i.e., all of these positions were either D-amino acids or all were L-amino acids). In FIG. 5, an upper case letter indicates an L-enantiomer and a lower case letter indicates a D-enantiomer.

The same modified ELISA was then used to investigate the impact of net charge of the peptide on the selective binding to C4S. The results of FIG. 6 demonstrate that the number of negatively charged residues in the "freely selectable positions" of the peptide directly correlated with the nonspecific binding to proteoglycans, and that decreasing the number of negatively charged residues at these positions increased specificity and/or selectivity for C4S.

7.2 Peptide Binding to C4S as Expressed on the Cell Surface

As explained throughout the description, the present molecules are able to selectively bind C4S over other proteoglycans. The binding selectivity of a FITC conjugated peptide of the invention, RYFvRIKYRh ("RYF"; SEQ ID NO:2) was assessed in cells expressing C4S (CHO cells) and cells lacking C4S (Sog9 cells; deficient in chondroitin 4-o-sulfotransferase 1 (C4ST-1, also known as CHST11). Sog9 (C4ST-) and CHO cells were incubated for 24 hrs in presence of the RYF (sequence: RYFvRIKYRh) peptide (2.5 M). Cells were then washed 3× in PBS before being fixed in methanol-acetone (1:1) and photographed with a LUMASCOPE™ fluorescence microscope. FIG. 7 demonstrates that the RYF peptide of the invention did not bind to the Sog9 cells lacking C4S; in contrast, the C4S expressing CHO cells exhibited intense, uniform binding.

The same fluorescent microscopy procedure was used to assess the binding of the FITC-RYF peptide on C4S expressing cells pre-treated with chlorate. Chlorate is an inhibitor of sulfotransferases, and, thus, chlorate treatment decreases or inhibits C4S expression. Macrophages were treated with 0, 3, 10 or 30 µM chlorate for 16 hours prior to washing, incubation with RYF (SEQ ID NO:2) peptide and photography as described above. FIG. 8 demonstrates that RYF (SEQ ID NO:2) binding correlated with chondroytine sulfate expression.

The experiments shown in FIGS. 7 and 8 revealed that the peptides of the invention were highly selective for C4S over other proteoglycans. Thus, the peptides allow the specific targeting of cells that exclusively express C4S or high levels of C4S relative to other proteoglycans. The primary enzyme responsible for the 4-sulfation of chondroitin, and thus the production of C4S, is CHST11. Expression data from Atlas arrays revealed that the CHST11 gene is preferentially expressed in cells from the leukocyte lineage (FIG. 9). Accordingly, the peptides and methods of the invention preferentially allow the targeting of leukocytes.

7.3 Use of Peptides of the Invention as a Carrier Molecule for a Therapeutic

The capacity for the peptides of the invention to act as carrier moieties, and the dependence on the levels and spacing of the D-amino acid residues therein was examined by the release of a FITC moiety from the peptide due to macrophage extracts. 1 µg of FITC-labeled peptides according to the invention with different levels and spacing of D-amino acids were incubated for up to 48 hours in "Raw" macrophage extracts (see, e.g., *J Exp Med.* 129(1969), 227-245) at 37° C. Together with free FITC as control, 0.5 ug of peptides were then spotted on cellulose paper (Whitman #1) before being subjected to (Thin Layer) chromatography using n-butanol, acetic acid, water (4:1:1) as solvent. The remaining 0.5 ug of samples were used for HPLC-MS/MS analysis. The legend for the peptides used in FIG. 10 is: peptides 1, 5 and 6 have the consensus: RXXxRXXXXRh; peptides 14, 15 and 16 have the consensus: RXxXRXXXXRh; peptides 23, 24 and 25 have the consensus: rXXXrXXXr (see, e.g., WO 2010/072228). The conjugation between the peptides and FITC was made through a regular covalent peptide bond to the N-terminal a.a. of the peptides. No degradation was observed for peptides 23, 24 and 25 because of conjugation to the N-terminal "r" ("d"-amino acid). The amount of free FITC released from the peptides ranges from 100% (#5) (consensus: RXXxRXXXXRh) to 30% (#15) (consensus: RXxXRXXXXRh). The data indicated that inclusion of a D-amino acid at position 4 of the peptide can modulate the stability and its ability to release the free BAM moiety.

Use of the exemplary peptide of the invention as a carrier moiety was also examined in a cell proliferation assay. Raw macrophage-derived cells were incubated for 48 hrs with 2.5 µM of the indicated nucleoside analog or the analog as a conjugate with the RYF peptide in the presence of phenol red. Cultures containing dividing cells turn medium clear, while the medium of cultures containing non-dividing cells remains dark (active compounds). Images of the cultures are presented in FIG. 11A. Percentage growth was also determined by measuring the relative content of LDH (FIG. 11B). The experiment demonstrated that the peptide-cytotoxic conjugate of the invention were able to kill a tumor macrophage cells (i.e., raw macrophage derived cells) and that the peptide was able to transport the cytotoxic into the cell, converting ineffective compounds into effective cytotoxic agents. For example, the "ribo" and "tg" (Thioguanine) compounds have no effect at the concentration tested (2.5 µm), but become potently cytotoxic when conjugated to an exemplary peptide transporter of the invention (i.e., RYF).

The Experiment was repeated to investigate the effects of the L- or D-linkage on cytotoxic properties of the BAM moiety. The cells were incubated with 3' amino β-D-arabinofuranoside either alone or in the form of a conjugate with the RYF peptide. As FIG. 12 demonstrates, the compound was only internalized with presented in the form of a conjugate. Additionally, it was surprisingly found that only use of the D-linking residue (i.e., "e" representing D-glutamic acid) was cytotoxic. This demonstrates that the linkage to the 3' position of the nucleoside sugar via a L-entantiomer (i.e., an L-amino acid) could be removed by proteases, converting the modified nucleoside in a "normal" one (i.e., with an —OH group at the 3' position, which does not act as a chain terminator). However, once the 3' position is conjugated to a D-entantiomer, it cannot be removed by a protease, and once incorporated into the DNA-strand, it will function to prevent further DNA elongation.

The experiment was repeated with 3'AdT (3' amino deoxythymidine) and 3' amino β-D-arabinofuranoside (Ribo). Cells were incubated with each of the compounds alone or as an N-terminally linked conjugate to the RYF peptide via either L-Glu (E) or D-Glu (e). The cells were then incubated for 72 hrs before LDH content was measured. FIG. 13 demonstrates that linkage with the D-entantiomer, D-glutamic acid ("e"), converts inactive compounds into highly cytostatic ones.

A similar assay was performed using MOLT4 cells. MOLT4 cells were incubated for 5 days with the indicated compounds or the compounds as a conjugates with the PYF peptide. MOLT4 cells aggregate together, thus allowing easy visualization of cell growth. FIG. 14 shows that, similar to the raw macrophage derived cells, RYF-cytotoxic conjugates kill tumor cells in vitro.

7.4 Modeling of the C4S-TAT Interaction

The mutagenesis studies of TAT as described herein demonstrated that residues Arg1, Lys/Arg3 or 7, Arg5, and Arg9 were the most important residues for the binding to C4S. In addition, comparison of the 3D structures of TAT and C4S, in their extended conformations, revealed that the average distance between side chains n and n+3 of TAT is very close to that of the sulfate and carboxylate groups of residues n and n+1 of C4S (FIG. 15).

These findings revealed that TAT and C4S likely bind due to the favorable electrostatic interactions between the pair of residues 1/n; 3/n+1; 5/n+2; 7/n+3; and 9/n+4 of TAT and C4S, respectively. In the recited A/B pairs, A and B designate residues of TAT and C4S, respectively; see, e.g., FIGS. 15 and 16, providing schematics of TAT and C4S molecules wherein the residues are indicated according to the numbering used herein. The favorable interactions between these sets of residues may be explained by 2 mechanisms (which are not necessarily mutually exclusive), depending on whether Arg1 of TAT would bind to a sugar moiety bearing a sulfate or a carboxylate group.

Due to the nature, the size and the flexibility of the two partners, it was not possible to identify the most likely binding mode using docking software. Therefore, we used a strategy consisting of (i) starting from the extended 3D conformers of both molecules, (ii) manually positioning the molecules to form the 3 adjacent contacts as described above (e.g. 3/n+1, 5/n+2, 7/n+3); (iii) perform a total of 600 ns of Molecular Dynamics (MD) simulations at 300 K while maintaining the chosen triplet of interactions; and, eventually, (iv) calculating whether new interactions would emerge during the MD simulations, and at which frequency. Importantly, at the start of the MD simulation, no interactions other than the chosen starting interactions occur between TAT and C4S.

The reasoning supporting this approach is that, if the envisioned interaction scheme constituted by five major pairs of interacting residues is correct, and if, for instance Arg1 of TAT binds preferably to a sulfated moiety of C4S, then, a MD simulation starting from a complex with only the interacting triplet (1/n, 3/n+1, 5/n+2) should lead to the spontaneous formation of more preferred interactions, e.g., 7/n+3 and 9/n+4, but only if residue n of C4S is a sulfated residue.

The interactions between TAT and C4S were modeled using the CHARMM molecular modeling package, version c36b1 (Brooks et al., *J. Comput. Chem.* 30(2009), 1545-1614). The TAT peptide (sequence: RKKRRQRRR) was described using the CHARMM22 all-hydrogen force fields (Mackerel) et al., *J. Phsy. Chem. B* 102(1998), 3586-3616), while topology and parameters were obtained using SwissParam for the C4S molecule (Zoete et al., *J. Comput. Chem.* 32(2011), 2359-2368). The C4S molecule was modeled to contain 10 sugar moieties, for example, as schematically represented in FIG. 16.

The starting points of the MD simulation were generated by manually positioning TAT and C4S, using the UCSF Chimera visualization software to form the interaction schemes of interest, i.e., involving three consecutive residues of C4S and 3 residues of TAT (for example, residues 1,3,5 or 3,5,7 or 5,7,9) (Pettersen et al., *J. Comput. Chem.* 25(2004), 1605-1612). To maintain the interaction between the chosen TAT/C4S residue pairs during the MD simulation, a "NOE" distance restraint was applied to them: RMIN and RMAX were set at 5 and 7 Å, respectively; and KMIN set at 1000 kcal mol$^{-1}$ Å$^{-2}$. The system was then minimized using 5000 steps of ABNR. Finally, for each starting interaction scheme, a pool of 30 independent MD simulations, each 20 ns in length, was performed at 300K to check whether additional interactions would take place between C4S and TAT. The solvent effect was estimated by the FACTS implicit solvation model, with a dielectric constant of 1 for the solute. For each MD simulation, 1000 frames, regularly separated, were extracted from the trajectory file. For each frame, pairs of interacting residues were identified as those having heavy atoms at a distance smaller than 5 Å. Finally, the frequency of existence of each possible pair of interacting residues was averaged over all frames extracted from the 30 MD simulations of each pool.

FIG. 17 provides two examples of interaction schemes formed during MD simulations starting from (A) the 3 contacts formed by residues 1/4, 3/5 and 5/6 or (B) from the 3 contacts formed by residues 3/4, 5/5 and 7/6 between the TAT molecules and C4S, respectively. As can be seen, during the MD simulations illustrated in (A), the system spontaneously formed interactions between the C-terminus of TAT and the high-numbered residues of C4S (see, e.g., FIGS. 18A and B), notably creating the interaction pairs 7/7 and 9/8 that were expected according to the above-mentioned hypothesis. In contrast, in the MD simulations illustrated in (B), only limited new interactions were formed.

Importantly, the two expected interactions 1/3 and 9/7 did not form. Interestingly, in the MD simulations illustrated in (A), the interaction scheme corresponds to the one where Arg1 is expected to interact with a sulfated residue of C4S, while in the MD simulations corresponding to (B), Arg1 was expected to interact with a carboxylated residue of C4S.

Several other groups of simulations were performed, each using different interaction schemes. In all cases where the scheme involved the interaction of Arg1 with a sulfated residue of C4S, nearly all the interactions expected according to our above-mentioned hypothesis occurred spontaneously during the MD simulation. In contrast, the expected interactions did not occur when the starting scheme involved an interaction between Arg1 and a carboxylated C4S residue. The results of the simulations support the hypothesis that TAT and C4S interact due to favorable electrostatic interactions between the pair of residues 1/n, 3/n+1, 5/n+2, 7/n+3 and 9/n+4, where residues n, n+2 and n+4 of C4S are sulfated moieties, and residue n+1 and n+3 are carboxylate moieties.

7.5 Use of Peptides of the Invention as a Carrier Molecule in Multiple Cell Lines The use of peptides of the invention as carrier molecules was investigated in a screening panel of human cancer cell lines. The human tumor cell lines of the cancer screening panel were grown in RPMI 1640 medium containing 5% fetal bovine serum and 2 mM L-glutamine. For a typical screening experiment, cells were inoculated into 96 well microtiter plates in volumes of 100 μL at plating densities ranging from 5,000 to 40,000 cells/well depending on the doubling time of individual cell lines. After cell inoculation, the microtiter plates were incubated at 37° C., 5% CO2, 95% air and 100% relative humidity for 24 h prior to addition of experimental drugs.

After 24 h, two plates of each cell line were fixed in situ with TCA to provide a measurement of the cell population at the time of drug addition (Tz). The experimental therapeutics were solubilized in dimethyl sulfoxide at 400-fold the desired final maximum test concentration and stored frozen prior to use. At the time of therapeutic addition, an aliquot of frozen concentrate was thawed and diluted to twice the desired final maximum test concentration using complete medium with 50 μg/ml gentamicin. Four further 10-fold or ½ log serial dilutions were also performed to provide a total of five test concentrations plus control. 100 μl aliquots of the different dilutions were added to the appropriate microtiter wells, which already contained 100 μl of medium, resulting in the desired final test concentrations.

Following addition of the test compound, the plates were incubated for an additional 48 h at 37° C., 5% CO2, 95% air, and 100% relative humidity. For adherent cells, the assay was terminated by the addition of cold TCA. Cells were fixed in situ by gentle addition of 50 μl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 μl) at 0.4% (w/v) in 1% acetic acid was added to each well, and the plates were incubated for 10 minutes at room temperature. After staining, unbound dye was removed by washing five times with 1% acetic acid followed by air drying. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 μl of 80% TCA (final concentration, 16% TCA). Using the seven absorbance measurements [time zero, (Tz), control growth, (C), and test growth in the presence of compound at the five concentration levels (Ti)], the percentage growth was calculated at each of the compound concentrations levels. Percentage growth inhibition was calculated as:

[(Ti−Tz)/(C−Tz)]×100 for concentrations for which Ti≥Tz

[(Ti−Tz)/Tz]×100 for concentrations for which Ti<Tz.

Calculated growth percent for each tested cell line is provided in Table 2

TABLE 2

| Cell Line | 3'AdT-RYF | Growth Percent Thioguanine-RYF | 5'AdT-RYF |
|---|---|---|---|
| Leukemia | | | |
| CCRF-CEM | 53.45 | 43.90 | 98.70 |
| HL-60(TB) | 70.62 | 51.19 | 95.89 |
| K-562 | 87.52 | 64.70 | 109.56 |
| MOLT-4 | 45.40 | 23.05 | 98.54 |
| RPMI-8226 | 81.35 | 68.08 | 104.25 |
| SR | 84.80 | 13.87 | 109.65 |
| Non-Small Cell Lung Cancer | | | |
| A549/ATCC | 82.45 | 92.64 | 102.66 |
| HOP-62 | 102.03 | 79.43 | 114.67 |
| HOP-92 | 98.25 | 94.99 | 99.83 |
| NCI-H226 | 96.97 | 90.76 | 106.10 |
| NCI-H23 | 98.27 | 104.79 | 115.75 |
| NCI-H322M | — | 120.25 | 118.09 |
| NCI-H460 | 33.43 | 38.65 | 102.43 |
| NCI-H522 | 110.62 | 102.59 | 119.23 |
| Colon Cancer | | | |
| COLO 205 | 108.84 | 114.86 | 111.19 |
| HCC-2998 | 102.58 | 106.69 | 117.32 |
| HCT-116 | 97.74 | 75.06 | 106.17 |
| HCT-15 | 106.90 | 100.79 | 111.73 |
| HT29 | 100.38 | 83.18 | 98.93 |
| KM12 | 105.07 | 97.68 | 107.42 |
| SW-620 | 92.66 | 61.11 | 107.90 |
| CNS Cancer | | | |
| SF-268 | 104.00 | 66.64 | 112.32 |
| SF-295 | 105.74 | 79.05 | 106.60 |
| SF-539 | 91.48 | 100.54 | 98.34 |
| SNB-19 | 110.60 | 101.24 | 107.37 |
| SNB-75 | 97.21 | 97.85 | 93.69 |
| U251 | 86.13 | 83.47 | 102.81 |
| Melanoma | | | |
| LOX IMVI | 97.19 | 42.72 | 104.99 |
| MALME-3M | 94.33 | 84.12 | 130.94 |
| M14 | 98.60 | 58.68 | 109.68 |
| MDA-MB-435 | 85.83 | 79.84 | 100.66 |
| SK-MEL-2 | 124.24 | 126.86 | 112.17 |
| SK-MEL-28 | 107.37 | 105.71 | 105.50 |
| SK-MEL-5 | 97.47 | 96.96 | 102.45 |
| UACC-257 | 96.89 | 84.76 | 105.98 |
| UACC-62 | 87.13 | 26.64 | 106.42 |
| Ovarian Cancer | | | |
| IGROV1 | 126.74 | 95.59 | 111.16 |
| OVCAR-3 | 118.06 | 103.06 | 113.03 |
| OVCAR-4 | 103.44 | 88.49 | 92.35 |
| OVCAR-5 | 122.59 | 109.15 | 107.73 |
| OVCAR-8 | 87.74 | 67.03 | 102.70 |
| NCI/ADR-RES | 88.17 | 54.63 | 113.90 |
| SK-OV-3 | 107.27 | 98.27 | 113.84 |
| Renal Cancer | | | |
| 786-0 | 106.78 | 94.97 | 112.19 |
| A498 | 107.72 | 97.50 | 117.71 |
| ACHN | 60.47 | 45.46 | 100.75 |
| RXF 393 | 96.63 | 91.71 | 97.28 |
| SN12C | — | 84.02 | 102.57 |

TABLE 2-continued

| Cell Line | 3'AdT-RYF | Growth Percent Thioguanine-RYF | 5'AdT-RYF |
|---|---|---|---|
| TK-10 | 108.34 | 111.91 | 110.77 |
| UO-31 | 100.01 | 57.20 | 114.49 |
| Prostate Cancer | | | |
| PC-3 | 81.48 | 76.13 | 104.03 |
| DU-145 | 90.48 | 64.98 | 107.78 |
| Breast Cancer | | | |
| MCF7 | 74.99 | 86.30 | 111.41 |
| MDA-MB-231/ATCC | 98.27 | 94.34 | 96.92 |
| HS 578T | 109.43 | 108.12 | 113.42 |
| BT-549 | 103.38 | 91.09 | 122.81 |
| T-47D | 100.40 | 89.47 | 109.17 |
| MDA-MB-468 | 99.93 | 98.01 | 104.66 |

Three dose response parameters were also calculated for each experimental agent (data not shown). Growth inhibition of 50% (GI50) was calculated from $[(Ti-Tz)/(C-Tz)] \times 100=50$, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment was calculated from $[(Ti-Tz)/Tz] \times 100=-50$. Values were calculated for each of these three parameters if the level of activity was reached; however, if the effect was not reached or is exceeded, the value for that parameter was expressed as greater or less than the maximum or minimum concentration tested.

As seen from Table 2, the experiment tested two active compounds (3'AdT and Thioguanine) conjugated to a RYF moiety to form a BAM conjugate as described herein. The BAM conjugate was tested for growth inhibition in 60 tumor cell lines (leukemias, non small cell lung cancer, colon cancer, CNS cancer, melanoma, ovarian cancer, renal cancer, prostate cancer, breast cancer). One non active conjugate (5'AdT, an inactive nucleotide analogue) was included as negative control. Two fold the standard deviation among non leukemia/lymphoma cell lines was used as the arbitrary threshold to detect growth inhibition (growth below 85% of untreated cells).

As expected, the negative control did not inhibit cell growth: none of the 60 cell lines grew below 85% of untreated cells. This demonstrates that the peptides according to the invention do not have intrinsic growth inhibition in this experimental setting.

Growth inhibition to both active compound conjugates was observed among 5 out of 6 leukemia/lymphoma cell lines (3'AdT: mean growth 71% of untreated; Thioguanine: 44.13% of untreated). In contrast, only 3 out of 54 cell lines from other lineages showed inhibited growth below 85% (3'AdT: mean growth 98.26% of untreated; Thioguanine: 86.65% of untreated). The difference in growth inhibition between leukemia cell lines and cancer cell lines of other origin was statistically significant for both 3'AdT ($p=0.010$) and Thioguanine ($p=0.003$), but not for negative control 5'AdT ($p>0.05$).

The response profile of growth inhibition corresponded to the expected expression of CHST11 gene and C4S in normal and tumor myeloid cells, and in tumor lymphoid cells. In conclusion, the results demonstrate that the peptides according to the invention selectively targeted tumor cells of the myeloid and lymphoid lineages, which both express CHST11 gene and thus C4S.

The invention claimed is:

1. A molecule or compound comprising one of the following consensus structures (I) to (IV):

$$\text{Arg}_1\text{-}(SP_A)\text{-}\text{Arg}_5\text{-}(SP_B)\text{-}X\text{-}(SP_C)\text{-}\text{Arg}_9\text{-}(LD_{10})_n\text{-}(XD_{11})_m; \quad (I)$$

$$\text{Arg}_1\text{-}(SP_C)\text{-}X\text{-}(SP_B)\text{-}\text{Arg}_5\text{-}(SP_A)\text{-}\text{Arg}_9\text{-}(LD_{10})_n\text{-}(XD_{11})_m; \quad (II)$$

$$(XD_{-2})_m\text{-}(LD_{-1})_n\text{-}\text{Arg}_1\text{-}(SP_A)\text{-}\text{Arg}_5\text{-}(SP_B)\text{-}X\text{-}(SP_C)\text{-}\text{Arg}_9; \text{ or} \quad (III)$$

$$(XD_{-2})_m\text{-}(LD_{-1})_n\text{-}\text{Arg}_1\text{-}(SP_C)\text{-}X\text{-}(SP_B)\text{-}\text{Arg}_5\text{-}(SP_A)\text{-}\text{Arg}_9, \quad (IV)$$

(a) wherein, $LD_{10}$ or $LD_{-1}$ represents any L- or D-amino acid other than D-arginine, D-lysine; L-arginine or L-lysine and n has a value of 0 to 10;

(b) wherein $XD_{11}$ or $XD_{-2}$ represents any D-amino acid other than D-arginine or D-lysine and m has a value of 0 or 1;

(c) wherein (i) $Arg_1$, $Arg_5$, and $Arg_9$ represent L-arginine; and X represents L-lysine or L-arginine, or (ii) $Arg_1$, $Arg_5$, and $Arg_9$ represent D-arginine; and X represents D-lysine or D-arginine;

(d) wherein ($SP_A$) represents a chemical linker that (i) consist of a peptide chain of 3 amino acid residues, wherein each residue may be independently selected from any amino acid residue other than D-arginine, D-lysine, L-arginine or L-lysine; or (ii) separates the adjacent amino acid residues by 12.9±1.5 Å;

(e) wherein ($SP_C$) represents a chemical linker that (i) consists of a single amino acid residue that may be any amino acid residue other than D-arginine, D-lysine, L-arginine or L-lysine; or (ii) separates the adjacent amino acid residues by 7.5±1.5 Å;

(f) wherein ($SP_B$)-X-($SP_C$) or its reverse, ($SP_C$)-X-($SP_B$) represents a chemical linker (i) wherein $SP_B$ and $SP_C$ each represent a single amino acid residue that may be independently selected from any amino acid residue other than D-arginine, D-lysine, L-arginine or L-lysine; or (ii) that separates the adjacent amino acid residues $Arg_1$ and $Arg_5$ or $Arg_5$ and $Arg_9$ by 12.9±1.5 Å

(g) and wherein where (i) $Arg_1$, $Arg_5$, and $Arg_9$ represent L-arginine; and X represents L-lysine or L-arginine;

(ii) ($SP_A$) consists of a peptide chain of 3 amino acid residues; and (iii) ($SP_B$) and ($SP_C$) each represent a single amino acid residue;

the consensus structures (I) to (IV) is represented by $$Arg_1\text{-}X_2\text{-}X_3\text{-}X_4\text{-}Arg_5\text{-}X_6\text{-}X_7\text{-}X_8\text{-}Arg_9\text{-}(LD_{10})_n\text{-}(XD_{11})_m;\text{ or} \quad (V)$$

$$(XD_{-2})_m\text{-}(LD_{-1})_n\text{-}Arg_1\text{-}X_2\text{-}X_3\text{-}X_4\text{-}Arg_5\text{-}X_6\text{-}X_7\text{-}X_8\text{-}Arg_9; \quad (VI)$$

having $Arg_1$, $Arg_5$ and $Arg_9$ as said L-arginines; having $X_3$ or $X_7$ as said L-lysine or L-arginine;

wherein in structure (V) or (VI), $X_4$ or $X_6$ is a D-amino acid.

2. The molecule or compound according to claim 1, wherein ($SP_A$) represents a chemical linker that separates the adjacent amino acid residues by 12.9±1.5 Å;

($SP_C$) represents a chemical linker that separates the adjacent amino acid residues by 7.5±1.5 Å;

and wherein ($SP_B$)-X-($SP_C$) or its reverse, ($SP_C$)-X-($SP_B$) represents a chemical linker that separates the adjacent amino acid residues $Arg_1$ and $Arg_5$ or $Arg_5$ and $Arg_9$ by 12.9±1.5 Å.

3. The molecule or compound of claim 1, wherein one or more of said chemical linkers is a beta-peptide, a sugar-amino acid based scaffold, a beta-hairpin peptidomimetic, a alpha-helical mimetic or a cyclotide.

4. The molecule or compound of claim 1, wherein ($SP_A$) represents a peptide chain consisting of three amino acid residues, each independently selected from any amino acid residue other than D-arginine, D-lysine, L-arginine or L-lysine; and wherein ($SP_B$) and ($SP_C$) each represent a single amino acid residue that may be independently selected from any amino acid residue other than D-arginine, D-lysine, L-arginine or L-lysine.

5. The molecule or compound according to claim 1, wherein ($SP_A$), ($SP_B$) and ($SP_C$) together contain no more than 3 alanine residues.

6. The molecule or compound according to claim 1, wherein ($SP_A$), ($SP_B$) and ($SP_C$) together contain no proline residues.

7. The molecule compound according to claim 1, wherein ($SP_A$), ($SP_B$) and ($SP_C$) together include one or more amino acids selected from Phe, Trp, Tyr, Val, Met, Ile, and Leu.

8. The molecule or compound according to claim 1, wherein ($SP_B$) represents a D-amino acid.

9. The molecule or compound according to claim 1, wherein $LD_{10}$ represents L- or D-histidine.

10. The molecule or compound according to claim 1, wherein $XD_{11}$ represents D-histidine.

11. The molecule or compound according to claim 1, wherein m has a value of 1, and/or n has a value of 0.

12. The molecule or compound according to claim 1, comprising a sequence selected from the group consisting of:

```
                          (SEQ ID NO: 1)
RSTqRYRVRh;

(SEQ ID NO: 2)
RYFvRIKYRh;

(SEQ ID NO: 3)
RYFvRIKARh;

(SEQ ID NO: 4)
RAAvRAKYRh;

(SEQ ID NO: 5)
RAAvRAKYRh;

(SEQ ID NO: 6)
RSTqRYRVRh;

(SEQ ID NO: 7)
RSTqRYKVRh;

(SEQ ID NO: 8)
RGGgRGKGRh;

(SEQ ID NO: 9)
RHHhRHKHRh;

(SEQ ID NO: 10)
RVVvRVKVRh;

(SEQ ID NO: 11)
RLLIRLKLRh;

(SEQ ID NO: 12)
RMMmRMKMRh;

(SEQ ID NO: 13)
RIIiRIKIRh;
```

-continued

```
                         (SEQ ID NO: 25)
RYFVRiKYRh;

(SEQ ID NO: 26)
RSTqRYRVR;

(SEQ ID NO: 15)
RYFvRIKYR;

(SEQ ID NO: 27)
RYFvRIKAR;

(SEQ ID NO: 28)
RAAvRAKYR;

(SEQ ID NO: 29)
RAAvRIKYR;

(SEQ ID NO: 30)
RSTqRYRVR;

(SEQ ID NO: 31)
RSTqRYKVR;

(SEQ ID NO: 32)
RGGgRGKGR;

(SEQ ID NO: 33)
RHHhRHKHR;

(SEQ ID NO: 34)
RVVvRVKVR;

(SEQ ID NO: 35)
RLLlRLKLR;

(SEQ ID NO: 36)
RMMmRMKMR;

(SEQ ID NO: 37)
RIIiRIKIR;
and (SEQ ID NO: 16)
RYFVRiKYR.
```

13. A conjugate of a biologically active moiety (BAM), and a consensus structure, wherein said BAM is conjugated to the terminus of said consensus structure and wherein said consensus structure is selected from one of the following consensus structures:

$$(BAM)\text{-}(LINK)\text{-}Arg_1\text{-}(SP_A)\text{-}Arg_5\text{-}(SP_B)\text{-}X\text{-}(SP_C)\text{-}Arg_9\text{-}(LD_{10})_n\text{-}(XD_{11})_m; \quad \text{(VII)}$$

$$((BAM))\text{-}(LINK)\text{-}Arg_1\text{-}(SP_C)\text{-}X\text{-}(SP_B)\text{-}Arg_5\text{-}(SP_A)\text{-}Arg_9\text{-}(LD_{10})_n\text{-}(XD_{11})_m; \quad \text{(VIII)}$$

$$(XD_{-2})_m\text{-}(LD_{-1})_n\text{-}Arg_1\text{-}(SP_A)Arg_5\text{-}(SP_B)\text{-}X\text{-}(SP_C)\text{-}Arg_9\text{-}(LINK)\text{-}(BAM);\text{ or} \quad \text{(IX)}$$

$$(XD_{-2})_m\text{-}(LD_{-1})_n\text{-}Arg_1\text{-}(SP_C)\text{-}X\text{-}(SP_B)\text{-}Arg_5\text{-}(SP_A)\text{-}Arg_9\text{-}(LINK)\text{-}((BAM)) \quad \text{(X)}$$

(a) wherein (BAM) represents a biologically active moiety;
(b) wherein (LINK) represents an optional linker group;
(c) wherein, $LD_{10}$ or $LD_{-1}$ represents any L- or D-amino acid other than D-arginine, D-lysine; L-arginine or L-lysine and n has a value of 0 to 10;
(d) wherein $XD_{11}$ or $XD_{-2}$ represents any D-amino acid other than D-arginine or D-lysine and m has a value of 0 or 1;
(e) wherein
  (i) $Arg_1$, $Arg_5$, and $Arg_9$ represent L-arginine; and X represents L-lysine or L-arginine, or (ii) $Arg_1$, $Arg_5$, and $Arg_9$ represent D-arginine; and X represents D-lysine or D-arginine;
(f) wherein ($SP_A$) represents a chemical linker that
  (i) consist of a peptide chain of 3 amino acid residues, wherein each residue may be independently selected from any amino acid residue other than D-arginine, D-lysine, L-arginine or L-lysine; or
  (ii) separates the adjacent amino acid residues by 12.9±1.5 Å;
(g) wherein ($SP_C$) represents a chemical linker that
  (i) consists of a single amino acid residue that may be any amino acid residue other than D-arginine, D-lysine, L-arginine or L-lysine; or
  (ii) separates the adjacent amino acid residues by 7.5±1.5 Å;
(h) wherein ($SP_B$)-X-($SP_C$) or its reverse, ($SP_C$)-X-($SP_B$) represents a chemical linker
  (i) wherein $SP_B$ and $SP_C$ each represent a single amino acid residue that may be independently selected from any amino acid residue other than D-arginine, D-lysine, L-arginine or L-lysine; or
  (ii) that separates the adjacent amino acid residues $Arg_1$ and $Arg_5$ or $Arg_5$ and $Arg_9$ by 12.9±1.5 Å
(i) and wherein where
  (i) $Arg_1$, $Arg_5$, and $Arg_9$ represent L-arginine; and X represents L-lysine or L-arginine;
  (ii) ($SP_A$) consists of a peptide chain of 3 amino acid residues; and
  (iii) ($SP_B$) and ($SP_C$) each represent a single amino acid residue;
the consensus structures (VII) to (X) is represented by $$(BAM)\text{-}(LINK)\text{-}Arg_1\text{-}X_2\text{-}X_3\text{-}X_4\text{-}Arg_5\text{-}X_6\text{-}X_7\text{-}X_8\text{-}Arg_9\text{-}(LD_{10})_n\text{-}(XD_{11})_m; \text{ or} \quad (XI)$$

$$(XD_{-2})_m\text{-}(LD_1)_n\text{-}Arg_1\text{-}X_2\text{-}X_3\text{-}X_4\text{-}Arg_5\text{-}X_6\text{-}X_7\text{-}X_8\text{-}Arg_9\text{-}(LINK)\text{-}(BAM); \quad (XII)$$

having $Arg_1$, $Arg_5$ and $Arg_9$ as said L-arginines; having $X_3$ or $X_7$ as said L-lysine or L-arginine;
wherein in structure (XI) or (XII), $X_4$ or $X_6$ is a D-amino acid.

14. The conjugate of claim 13, wherein the linker group (LINK) is L- or D-Glu.

15. The conjugate of claim 13, wherein the BAM is conjugated to the $Arg_1$ or $Arg_9$ by a covalent N-terminus amide- or C-terminus ester bond.

16. The conjugate of claim 13, wherein said BAM is conjugated to a amino acid residue and/or a chemical group within ($SP_A$), ($SP_B$) or ($SP_C$).

17. The conjugate of claim 14, wherein said conjugation is either direct conjugation to an internal residue of said peptide sequence or indirect via a linker group.

18. The conjugate according to claim 13, wherein the BAM is a mono- or poly saccharide, a cytotoxic agent, an antineoplastic agent, an anti-inflammatory agent, an antiviral agent, an anti-bacterial agent or an agent for the treatment of protozoan infections.

19. The conjugate according to claim 13, wherein the BAM is deoxyribose or ribose.

20. A pharmaceutical composition comprising the conjugate according to claim 13.

21. A method of modulating leukocytes or treating a disorder involving leukocyte modulation, comprising administering to an individual in need thereof a conjugate according to claim 13, wherein the conjugate targets CD68 and/or C4S expressing cells, thereby modulating said leukocytes.

22. The method according to claim 21, wherein the disorder is leishmaniasis.

* * * * *

SEQUENCE LISTING

```
<160> NUMBER OF SEQ ID NOS: 37

<210> SEQ ID NO 1
<211> LENGTH: 10
<212> TYPE: PRT
<213> ORGANISM: Artificial Sequence
<220> FEATURE:
<223> OTHER INFORMATION: Artificial C4S binding peptide
<220> FEATURE:
<221> NAME/KEY: VARIANT
<222> LOCATION: 4
<223> OTHER INFORMATION: Xaa in position 4 is D-Gln
<220> FEATURE:
<221> NAME/KEY: VARIANT
<222> LOCATION: 10
<223> OTHER INFORMATION: Xaa at position 10 is D-His

<400> SEQUENCE: 1

Arg Ser Thr Xaa Arg Tyr Arg Val Arg Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Artifical C4S binding peptide
<220> FEATURE:
<221> NAME/KEY: VARIANT
<222> LOCATION: 4
<223> OTHER INFORMATION: Xaa at position 4 is D-Val
<220> FEATURE:
```

```
<221> NAME/KEY: VARIANT
<222> LOCATION: 10
<223> OTHER INFORMATION: Xaa at position 10 is D-His

<400> SEQUENCE: 2

Arg Tyr Phe Xaa Arg Ile Lys Tyr Arg Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Artifical C4S binding peptide
<220> FEATURE:
<221> NAME/KEY: VARIANT
<222> LOCATION: 4
<223> OTHER INFORMATION: Xaa at position 4 is D-Val
<220> FEATURE:
<221> NAME/KEY: VARIANT
<222> LOCATION: 10
<223> OTHER INFORMATION: Xaa at position 10 is D-His

<400> SEQUENCE: 3

Arg Tyr Phe Xaa Arg Ile Lys Ala Arg Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Artifical C4S binding peptide
<220> FEATURE:
<221> NAME/KEY: VARIANT
<222> LOCATION: 4
<223> OTHER INFORMATION: Xaa at postition 4 is D-Val
<220> FEATURE:
<221> NAME/KEY: VARIANT
<222> LOCATION: 10
<223> OTHER INFORMATION: Xaa at position 10 is D-His

<400> SEQUENCE: 4

Arg Ala Ala Xaa Arg Ala Lys Tyr Arg Xaa
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 4
<223> OTHER INFORMATION: Xaa at position 4 is D-Val
<220> FEATURE:
<221> NAME/KEY: VARIANT
<222> LOCATION: 10
<223> OTHER INFORMATION: Xaa at position 10 is D-His

<400> SEQUENCE: 5

Arg Ala Ala Xaa Arg Ile Lys Tyr Arg Xaa
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Artificial C4S Binding Peptide
```

```
<220> FEATURE:
<221> NAME/KEY: VARIANT
<222> LOCATION: 4
<223> OTHER INFORMATION: Xaa at position 4 is D-Gln
<220> FEATURE:
<221> NAME/KEY: VARIANT
<222> LOCATION: 10
<223> OTHER INFORMATION: Xaa at position 10 is D-His

<400> SEQUENCE: 6

Arg Ser Thr Xaa Arg Tyr Arg Val Arg Xaa
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 4
<223> OTHER INFORMATION: Xaa at position 4 is D-Gln
<220> FEATURE:
<221> NAME/KEY: VARIANT
<222> LOCATION: 10
<223> OTHER INFORMATION: Xaa at position 10 is D-His

<400> SEQUENCE: 7

Arg Ser Thr Xaa Arg Tyr Lys Val Arg Xaa
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 4
<223> OTHER INFORMATION: Xaa at position 4 is D-Gln
<220> FEATURE:
<221> NAME/KEY: VARIANT
<222> LOCATION: 10
<223> OTHER INFORMATION: Xaa at position 10 is D-His

<400> SEQUENCE: 8

Arg Gly Gly Xaa Arg Gly Lys Gly Arg Xaa
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VAR_SEQ
<222> LOCATION: 4
<223> OTHER INFORMATION: Xaa at position 4 is D-His
<220> FEATURE:
<221> NAME/KEY: VARIANT
<222> LOCATION: 10
<223> OTHER INFORMATION: Xaa at position 10 is D-His

<400> SEQUENCE: 9

Arg His His Xaa Arg His Lys His Arg Xaa
1               5                   10

<210> SEQ ID NO 10
```

```
<211> LENGTH: 10
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 4
<223> OTHER INFORMATION: Xaa at position 4 is D-Val
<220> FEATURE:
<221> NAME/KEY: VARIANT
<222> LOCATION: 10
<223> OTHER INFORMATION: Xaa at position 10 is D-His

<400> SEQUENCE: 10

Arg Val Val Xaa Arg Val Lys Val Arg Xaa
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 4
<223> OTHER INFORMATION: Xaa at position 4 is a D-Leu
<220> FEATURE:
<221> NAME/KEY: VARIANT
<222> LOCATION: 10
<223> OTHER INFORMATION: Xaa at position 10 is a D-His

<400> SEQUENCE: 11

Arg Leu Leu Xaa Arg Leu Lys Leu Arg Xaa
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 4
<223> OTHER INFORMATION: Xaa at position 4 is a D-Met
<220> FEATURE:
<221> NAME/KEY: VARIANT
<222> LOCATION: 10
<223> OTHER INFORMATION: Xaa at position 10 is a D-His

<400> SEQUENCE: 12

Arg Met Met Xaa Arg Met Lys Met Arg Xaa
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 4
<223> OTHER INFORMATION: Xaa at position 4 is a D-Ile
<220> FEATURE:
<221> NAME/KEY: VARIANT
<222> LOCATION: 10
<223> OTHER INFORMATION: Xaa at position 10 is a D-His

<400> SEQUENCE: 13
```

```
Arg Ile Ile Xaa Arg Ile Lys Ile Arg Xaa
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Artificial C4S Binding Peptide

<400> SEQUENCE: 14

Arg Tyr Phe Val Arg Ile Lys Tyr Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 4
<223> OTHER INFORMATION: Xaa at position 4 is a D-Val

<400> SEQUENCE: 15

Arg Tyr Phe Xaa Arg Ile Lys Tyr Arg
1               5

<210> SEQ ID NO 16
<211> LENGTH: 9
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 6
<223> OTHER INFORMATION: Xaa at position 6 is a D-Ile

<400> SEQUENCE: 16

Arg Tyr Phe Val Arg Xaa Lys Tyr Arg
1               5

<210> SEQ ID NO 17
<211> LENGTH: 11
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 2
<223> OTHER INFORMATION: Xaa at position 2 is any L- or D- amino acid
      other than L-Lys, D-Lys, L-Arg or D-Arg
<220> FEATURE:
<221> NAME/KEY: VARIANT
<222> LOCATION: 3
<223> OTHER INFORMATION: Xaa at position 3 is any L- or D- amino acid
      other than L-Lys, D-Lys, L-Arg or D-Arg, subject to the proviso
      that Xaa at position 3 or Xaa at position 7, but not both, is
      L-Lys or L-Arg
<220> FEATURE:
<221> NAME/KEY: VARIANT
<222> LOCATION: 4
<223> OTHER INFORMATION: Xaa at position 4 is any L- or D- amino acid
      other than L-Lys, D-Lys, L-Arg or D-Arg
<220> FEATURE:
<221> NAME/KEY: VARIANT
<222> LOCATION: 6
<223> OTHER INFORMATION: Xaa at position 6 is any L- or D- amino acid
      other than L-Lys, D-Lys, L-Arg or D-Arg
```

```
-continued

<220> FEATURE:
<221> NAME/KEY: VARIANT
<222> LOCATION: 7
<223> OTHER INFORMATION: Xaa at position 7 is any L- or D- amino acid
      other than L-Lys, D-Lys, L-Arg or D-Arg, subject to the proviso
      that Xaa at position 3 or Xaa at position 7, but not both, is
      L-Lys or L-Arg
<220> FEATURE:
<221> NAME/KEY: VARIANT
<222> LOCATION: 8
<223> OTHER INFORMATION: Xaa at position 8 is any L- or D- amino acid
      other than L-Lys, D-Lys, L-Arg or D-Arg
<220> FEATURE:
<221> NAME/KEY: VARIANT
<222> LOCATION: 10
<223> OTHER INFORMATION: Xaa at position 10 represents from 0 to 10
      amino acids, each independently any L- or D- amino acid other that
      D-Arg, D-Lys, L-Arg or L-lys
<220> FEATURE:
<221> NAME/KEY: VARIANT
<222> LOCATION: 11
<223> OTHER INFORMATION: Xaa at position 11 represents from 0 to 1 amino
      acid, which may be any D-amino acid other that D-Arg or D-Lys

<400> SEQUENCE: 17

Arg Xaa Xaa Xaa Arg Xaa Xaa Xaa Arg Xaa Xaa
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 1
<223> OTHER INFORMATION: Xaa at position 1 represents from 0 to 1 amino
      acid, which may be any D-amino acid other than D-Arg or D-Lysi
<220> FEATURE:
<221> NAME/KEY: VARIANT
<222> LOCATION: 2
<223> OTHER INFORMATION: Xaa at position 2 represents from 0 to 10 amino
      acids, each independently any L- or D- amino acid other than
      D-Arg, D-Lys, L-Arg, or L-Lys
<220> FEATURE:
<221> NAME/KEY: VARIANT
<222> LOCATION: 4
<223> OTHER INFORMATION: Xaa at position 4 is any L- or D- amino acid
      other than L-Lys, D-Lys, L-Arg or D-Arg
<220> FEATURE:
<221> NAME/KEY: VARIANT
<222> LOCATION: 5
<223> OTHER INFORMATION: Xaa at position 5 is any L- or D- amino acid
      other than L-Lys, D-Lys, L-Arg, or D- Arg, subject to the proviso
      that Xaa at position 5 or Xaa at postion 9, but not both, is L-Lys
      or L-Arg
<220> FEATURE:
<221> NAME/KEY: VARIANT
<222> LOCATION: 6
<223> OTHER INFORMATION: Xaa at position 6 is any L- or D- amino acid
      other than L-Lys, D-Lys, L-Arg, or D- Arg
<220> FEATURE:
<221> NAME/KEY: VARIANT
<222> LOCATION: 8
<223> OTHER INFORMATION: Xaa at position 8 is any L- or D- amino acid
      other than L-Lys, D-Lys, L-Arg, or D-Arg
<220> FEATURE:
<221> NAME/KEY: VARIANT
<222> LOCATION: 9
<223> OTHER INFORMATION: Xaa at position 9 is any L- or D- amino acid
      other than L-Lys, D-Lys, L-Arg, or D- Arg, subject to the proviso
      that Xaa at position 5 or Xaa at postion 9, but not both, is L-Lys
      or L-Arg
<220> FEATURE:
<221> NAME/KEY: VARIANT
<222> LOCATION: 10
```

```
<223> OTHER INFORMATION: Xaa at position 10 is any L- or D- amino acid
      other than L-Lys, D-Lys, L-Arg, or D-Arg

<400> SEQUENCE: 18

Xaa Xaa Arg Xaa Xaa Xaa Arg Xaa Xaa Xaa Arg
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 2
<223> OTHER INFORMATION: Xaa at position 2 is any L- or D- amino acid
      other than L-Lys, D-Lys, L-Arg or D-Arg
<220> FEATURE:
<221> NAME/KEY: VARIANT
<222> LOCATION: 3
<223> OTHER INFORMATION: Xaa at position 3 is any L- or D- amino acid
      other than L-Lys, D-Lys, L-Arg or D-Arg, subject to the proviso
      that Xaa at position 3 or Xaa at position 7, but not both, is
      D-Lys or D-Arg
<220> FEATURE:
<221> NAME/KEY: VARIANT
<222> LOCATION: 4
<223> OTHER INFORMATION: Xaa at position 4 is any L- or D- amino acid
      other than L-Lys, D-Lys, L-Arg or D-Arg
<220> FEATURE:
<221> NAME/KEY: VARIANT
<222> LOCATION: 6
<223> OTHER INFORMATION: Xaa at position 6 is any L- or D- amino acid
      other than L-Lys, D-Lys, L-Arg or D-Arg
<220> FEATURE:
<221> NAME/KEY: VARIANT
<222> LOCATION: 7
<223> OTHER INFORMATION: Xaa at position 7 is any L- or D- amino acid
      other than L-Lys, D-Lys, L-Arg or D-Arg, subject to the proviso
      that Xaa at position 3 or Xaa at position 7, but not both, is
      D-Lys or D-Arg
<220> FEATURE:
<221> NAME/KEY: VARIANT
<222> LOCATION: 8
<223> OTHER INFORMATION: Xaa at position 8 is any L- or D- amino acid
      other than L-Lys, D-Lys, L-Arg or D-Arg
<220> FEATURE:
<221> NAME/KEY: VARIANT
<222> LOCATION: 10
<223> OTHER INFORMATION: Xaa at position 10 represents from 0 to 10
      amino acids, each independently any L- or D- amino acid other that
      D-Arg, D-Lys, L-Arg or L-lys
<220> FEATURE:
<221> NAME/KEY: VARIANT
<222> LOCATION: 11
<223> OTHER INFORMATION: Xaa at position 11 represents from 0 to 1 amino
      acid, which may be any D-amino acid other that D-Arg or D-Lys
<220> FEATURE:
<221> NAME/KEY: VARIANT
<222> LOCATION: 1
<223> OTHER INFORMATION: Xaa at position 1 is D-Arg
<220> FEATURE:
<221> NAME/KEY: VARIANT
<222> LOCATION: 5
<223> OTHER INFORMATION: Xaa at position 5 is D-Arg
<220> FEATURE:
<221> NAME/KEY: VARIANT
<222> LOCATION: 9
<223> OTHER INFORMATION: Xaa at position 9 is D-Arg

<400> SEQUENCE: 19

Xaa Xaa Xaa Xaa Xaa Xaa Xaa Xaa Xaa Xaa Xaa
1               5                   10
```

```
<210> SEQ ID NO 20
<211> LENGTH: 11
<212> TYPE: PRT
<213> ORGANISM: Artificial Sequence
<220> FEATURE:
<223> OTHER INFORMATION: Artificial C4S Binding Peptide
<220> FEATURE:
<221> NAME/KEY: VARIANT
<222> LOCATION: 1
<223> OTHER INFORMATION: Xaa at position 1 represents from 0 to 1 amino
      acid, which may be any D-amino acid other than D-Arg or D-Lysi
<220> FEATURE:
<221> NAME/KEY: VARIANT
<222> LOCATION: 2
<223> OTHER INFORMATION: Xaa at position 2 represents from 0 to 10 amino
      acids, each independently any L- or D- amino acid other than
      D-Arg, D-Lys, L-Arg, or L-Lys
<220> FEATURE:
<221> NAME/KEY: VARIANT
<222> LOCATION: 4
<223> OTHER INFORMATION: Xaa at position 4 is any L- or D- amino acid
      other than L-Lys, D-Lys, L-Arg or D-Arg
<220> FEATURE:
<221> NAME/KEY: VARIANT
<222> LOCATION: 5
<223> OTHER INFORMATION: Xaa at position 5 is any L- or D- amino acid
      other than L-Lys, D-Lys, L-Arg, or D- Arg, subject to the proviso
      that Xaa at position 5 or Xaa at postion 9, but not both, is D-Lys
      or D-Arg
<220> FEATURE:
<221> NAME/KEY: VARIANT
<222> LOCATION: 6
<223> OTHER INFORMATION: Xaa at position 6 is any L- or D- amino acid
      other than L-Lys, D-Lys, L-Arg, or D- Arg
<220> FEATURE:
<221> NAME/KEY: VARIANT
<222> LOCATION: 8
<223> OTHER INFORMATION: Xaa at position 8 is any L- or D- amino acid
      other than L-Lys, D-Lys, L-Arg, or D-Arg
<220> FEATURE:
<221> NAME/KEY: VARIANT
<222> LOCATION: 9
<223> OTHER INFORMATION: Xaa at position 9 is any L- or D- amino acid
      other than L-Lys, D-Lys, L-Arg, or D- Arg, subject to the proviso
      that Xaa at position 5 or Xaa at postion 9, but not both, is D-Lys
      or D-Arg
<220> FEATURE:
<221> NAME/KEY: VARIANT
<222> LOCATION: 10
<223> OTHER INFORMATION: Xaa at position 10 is any L- or D- amino acid
      other than L-Lys, D-Lys, L-Arg, or D-Arg
<220> FEATURE:
<221> NAME/KEY: VARIANT
<222> LOCATION: 3
<223> OTHER INFORMATION: Xaa at position 3 is D-Arg
<220> FEATURE:
<221> NAME/KEY: VARIANT
<222> LOCATION: 7
<223> OTHER INFORMATION: Xaa at position 7 is D-Arg
<220> FEATURE:
<221> NAME/KEY: VARIANT
<222> LOCATION: 11
<223> OTHER INFORMATION: Xaa at position 11 is D-Arg

<400> SEQUENCE: 20

Xaa Xaa Xaa Xaa Xaa Xaa Xaa Xaa Xaa Xaa Xaa
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Consensus Targeting Moiety of Sequences 17
      and 18
<220> FEATURE:
<221> NAME/KEY: VARIANT
```

```
<222> LOCATION: 2
<223> OTHER INFORMATION: Xaa at position 2 is any L- or D- amino acid
      other than L-Lys, D-Lys, L-Arg or D-Arg
<220> FEATURE:
<221> NAME/KEY: VARIANT
<222> LOCATION: 3
<223> OTHER INFORMATION: Xaa at position 3 is any L- or D- amino acid
      other than L-Lys, D-Lys, L-Arg or D-Arg, subject to the proviso
      that Xaa at position 3 or Xaa at position 7, but not both, is
      L-Lys or L-Arg
<220> FEATURE:
<221> NAME/KEY: VARIANT
<222> LOCATION: 4
<223> OTHER INFORMATION: Xaa at position 4 is any L- or D- amino acid
      other than L-Lys, D-Lys, L-Arg or D-Arg
<220> FEATURE:
<221> NAME/KEY: VARIANT
<222> LOCATION: 6
<223> OTHER INFORMATION: Xaa at position 6 is any L- or D- amino acid
      other than L-Lys,
 D-Lys, L-Arg or D-Arg
<220> FEATURE:
<221> NAME/KEY: VARIANT
<222> LOCATION: 7
<223> OTHER INFORMATION: Xaa at position 7 is any L- or D- amino acid
      other than L-Lys, D-Lys, L-Arg or D-Arg, subject to the proviso
      that Xaa at position 3 or Xaa at position 7, but not both, is
      L-Lys or L-Arg
<220> FEATURE:
<221> NAME/KEY: VARIANT
<222> LOCATION: 8
<223> OTHER INFORMATION: Xaa at position 8 is any L- or D- amino acid
      other than L-Lys, D-Lys, L-Arg or D-Arg

<400> SEQUENCE: 21

Arg Xaa Xaa Xaa Arg Xaa Xaa Xaa Arg
1               5

<210> SEQ ID NO 22
<211> LENGTH: 9
<212> TYPE: PRT
<213> ORGANISM: Artificial Sequence
<220> FEATURE:
<223> OTHER INFORMATION: Consensus Targeting Moiety of Sequneces 19 and
      20
<220> FEATURE:
<221> NAME/KEY: VARIANT
<222> LOCATION: 2
<223> OTHER INFORMATION: Xaa at position 2 is any L- or D- amino acid
      other than L-Lys, D-Lys, L-Arg or D-Arg
<220> FEATURE:
<221> NAME/KEY: VARIANT
<222> LOCATION: 3
<223> OTHER INFORMATION: Xaa at position 3 is any L- or D- amino acid
      other than L-Lys, D-Lys, L-Arg or D-Arg, subject to the proviso
      that Xaa at position 3 or Xaa at position 7, but not both, is
      D-Lys or D-Arg
<220> FEATURE:
<221> NAME/KEY: VARIANT
<222> LOCATION: 4
<223> OTHER INFORMATION: Xaa at position 4 is any L- or D- amino acid
      other than L-Lys, D-Lys, L-Arg or D-Arg
<220> FEATURE:
<221> NAME/KEY: VARIANT
<222> LOCATION: 6
<223> OTHER INFORMATION: Xaa at position 6 is any L- or D- amino acid
      other than L-Lys, D-Lys, L-Arg or D-Arg
<220> FEATURE:
<221> NAME/KEY: VARIANT
<222> LOCATION: 7
<223> OTHER INFORMATION: Xaa at position 7 is any L- or D- amino acid
      other than L-Lys, D-Lys, L-Arg or D-Arg, subject to the proviso
      that Xaa at position 3 or Xaa at position 7, but not both, is
      D-Lys or D-Arg
<220> FEATURE:
<221> NAME/KEY: VARIANT
<222> LOCATION: 8
```

<223> OTHER INFORMATION: Xaa at position 8 is any L- or D- amino acid
      other than L-Lys, D-Lys, L-Arg or D-Arg
<220> FEATURE:
<221> NAME/KEY: VARIANT
<222> LOCATION: 1
<223> OTHER INFORMATION: Xaa at position 1 is D-Arg
<220> FEATURE:
<221> NAME/KEY: VARIANT
<222> LOCATION: 5
<223> OTHER INFORMATION: Xaa at position 5 is D-Arg
<220> FEATURE:
<221> NAME/KEY: VARIANT
<222> LOCATION: 9
<223> OTHER INFORMATION: Xaa at position 9 is D-Arg

<400> SEQUENCE: 22

Xaa Xaa Xaa Xaa Xaa Xaa Xaa Xaa Xaa
1               5

<210> SEQ ID NO 23
<211> LENGTH: 5
<212> TYPE: PRT
<213> ORGANISM: Artificial Sequence
<220> FEATURE:
<223> OTHER INFORMATION: Artificial linker

<400> SEQUENCE: 23

Gly Gly Gly Gly Gly
1               5

<210> SEQ ID NO 24
<211> LENGTH: 4
<212> TYPE: PRT
<213> ORGANISM: Artificial Sequence
<220> FEATURE:
<223> OTHER INFORMATION: Artificial Linker

<400> SEQUENCE: 24

Gly Gly Gly Gly
1

<210> SEQ ID NO 25
<211> LENGTH: 10
<212> TYPE: PRT
<213> ORGANISM: Artificial Sequence
<220> FEATURE:
<223> OTHER INFORMATION: artificial C4S binding peptide
<220> FEATURE:
<221> NAME/KEY: VARIANT
<222> LOCATION: 6
<223> OTHER INFORMATION: Xaa at position 6 is D-Ile
<220> FEATURE:
<221> NAME/KEY: VARIANT
<222> LOCATION: 10
<223> OTHER INFORMATION: Xaa at position 10 is D-His

<400> SEQUENCE: 25

Arg Tyr Phe Val Arg Xaa Lys Tyr Arg Xaa
1               5                   10

<210> SEQ ID NO 26
<211> LENGTH: 9
<212> TYPE: PRT
<213> ORGANISM: Artificial Sequence
<220> FEATURE:
<223> OTHER INFORMATION: artificial C4S binding peptide
<220> FEATURE:
<221> NAME/KEY: VARIANT
<222> LOCATION: 4
<223> OTHER INFORMATION: Xaa at position 4 is D-Gln

```
<400> SEQUENCE: 26

Arg Ser Thr Xaa Arg Tyr Arg Val Arg
1               5

<210> SEQ ID NO 27
<211> LENGTH: 9
<212> TYPE: PRT
<213> ORGANISM: Artificial Sequence
<220> FEATURE:
<223> OTHER INFORMATION: artificial C4S binding peptide
<220> FEATURE:
<221> NAME/KEY: VARIANT
<222> LOCATION: 4
<223> OTHER INFORMATION: Xaa at position 4 is D-Val

<400> SEQUENCE: 27

Arg Tyr Phe Xaa Arg Ile Lys Ala Arg
1               5

<210> SEQ ID NO 28
<211> LENGTH: 9
<212> TYPE: PRT
<213> ORGANISM: Artificial Sequence
<220> FEATURE:
<223> OTHER INFORMATION: artificial C4S binding peptide
<220> FEATURE:
<221> NAME/KEY: VARIANT
<222> LOCATION: 4
<223> OTHER INFORMATION: Xaa at position 4 is D-Val

<400> SEQUENCE: 28

Arg Ala Ala Xaa Arg Ala Lys Tyr Arg
1               5

<210> SEQ ID NO 29
<211> LENGTH: 9
<212> TYPE: PRT
<213> ORGANISM: Artificial Sequence
<220> FEATURE:
<223> OTHER INFORMATION: artificial C4S binding peptide
<220> FEATURE:
<221> NAME/KEY: VARIANT
<222> LOCATION: 4
<223> OTHER INFORMATION: Xaa at position 4 is D-Val

<400> SEQUENCE: 29

Arg Ala Ala Xaa Arg Ile Lys Tyr Arg
1               5

<210> SEQ ID NO 30
<211> LENGTH: 9
<212> TYPE: PRT
<213> ORGANISM: Artificial Sequence
<220> FEATURE:
<223> OTHER INFORMATION: artificial C4S binding peptide
<220> FEATURE:
<221> NAME/KEY: VARIANT
<222> LOCATION: 4
<223> OTHER INFORMATION: Xaa at position 4 is D-Gln

<400> SEQUENCE: 30

Arg Ser Thr Xaa Arg Tyr Arg Val Arg
1               5

<210> SEQ ID NO 31
<211> LENGTH: 9
<212> TYPE: PRT
<213> ORGANISM: Artificial Sequence
<220> FEATURE:
```

```
<223> OTHER INFORMATION: artificial C4S binding peptide
<220> FEATURE:
<221> NAME/KEY: VARIANT
<222> LOCATION: 4
<223> OTHER INFORMATION: Xaa at position 4 is D-Gln

<400> SEQUENCE: 31

Arg Ser Thr Xaa Arg Tyr Lys Val Arg
1               5

<210> SEQ ID NO 32
<211> LENGTH: 9
<212> TYPE: PRT
<213> ORGANISM: Artificial Sequence
<220> FEATURE:
<223> OTHER INFORMATION: artificial C4S binding peptide
<220> FEATURE:
<221> NAME/KEY: VARIANT
<222> LOCATION: 4
<223> OTHER INFORMATION: Xaa at position 4 is D-Gly

<400> SEQUENCE: 32

Arg Gly Gly Xaa Arg Gly Lys Gly Arg
1               5

<210> SEQ ID NO 33
<211> LENGTH: 9
<212> TYPE: PRT
<213> ORGANISM: Artificial Sequence
<220> FEATURE:
<223> OTHER INFORMATION: artificial C4S binding peptide
<220> FEATURE:
<221> NAME/KEY: VARIANT
<222> LOCATION: 4
<223> OTHER INFORMATION: Xaa at position 4 is D-His

<400> SEQUENCE: 33

Arg His His Xaa Arg His Lys His Arg
1               5

<210> SEQ ID NO 34
<211> LENGTH: 9
<212> TYPE: PRT
<213> ORGANISM: Artificial Sequence
<220> FEATURE:
<223> OTHER INFORMATION: artificial C4S binding peptide
<220> FEATURE:
<221> NAME/KEY: VARIANT
<222> LOCATION: 4
<223> OTHER INFORMATION: Xaa at position 4 is D-Val

<400> SEQUENCE: 34

Arg Val Val Xaa Arg Val Lys Val Arg
1               5

<210> SEQ ID NO 35
<211> LENGTH: 9
<212> TYPE: PRT
<213> ORGANISM: Artificial Sequence
<220> FEATURE:
<223> OTHER INFORMATION: artificial C4S binding peptide
<220> FEATURE:
<221> NAME/KEY: VARIANT
<222> LOCATION: 4
<223> OTHER INFORMATION: Xaa at position 4 is D-Leu

<400> SEQUENCE: 35

Arg Leu Leu Xaa Arg Leu Lys Leu Arg
1               5
```

```
<210> SEQ ID NO 36
<211> LENGTH: 9
<212> TYPE: PRT
<213> ORGANISM: Artificial Sequence
<220> FEATURE:
<223> OTHER INFORMATION: artificial C4S binding peptide
<220> FEATURE:
<221> NAME/KEY: VARIANT
<222> LOCATION: 4
<223> OTHER INFORMATION: Xaa at position 4 is D-Met

<400> SEQUENCE: 36

Arg Met Met Xaa Arg Met Lys Met Arg
1               5

<210> SEQ ID NO 37
<211> LENGTH: 9
<212> TYPE: PRT
<213> ORGANISM: Artificial Sequence
<220> FEATURE:
<223> OTHER INFORMATION: artificial C4S binding peptide
<220> FEATURE:
<221> NAME/KEY: VARIANT
<222> LOCATION: 4
<223> OTHER INFORMATION: Xaa at position 4 is D-Ile

<400> SEQUENCE: 37

Arg Ile Ile Xaa Arg Ile Lys Ile Arg
1               5
```